US009789130B2

(12) United States Patent
Izquierdo Useros et al.

(10) Patent No.: US 9,789,130 B2
(45) Date of Patent: Oct. 17, 2017

(54) METHOD FOR BLOCKING HIV ENTRY INTO DENDRITIC CELLS BY INHIBITING SIALOADHESIN-SIALYLLACTOSE BINDING INTERACTIONS WITH GANGLIOSIDES

(71) Applicants: Nuria Izquierdo Useros, Barcelona (ES); Hans-Georg Krauesslich, Heidelberg (DE); Maier Lorizate, Portugalete (ES); Javier Martinez Picado, Vilassar del Mar (ES)

(72) Inventors: Nuria Izquierdo Useros, Barcelona (ES); Hans-Georg Krauesslich, Heidelberg (DE); Maier Lorizate, Portugalete (ES); Javier Martinez Picado, Vilassar del Mar (ES)

(73) Assignees: LABORATORIOS DEL DR. ESTEVE, S.A., Barcelona (ES); FUNDACIÓ PRIVADA INSTITUT DE RECERCA DE LA SIDA—CAIXA, Badalona (ES); INSTITUCIÓ CATALANA DE RECERCA I ESTUDIS AVANÇATS, Barcelona (ES); RUPRECHT-KARLS-UNIVERSITAET HEIDELBERG, Heidelberg (DE)

( * ) Notice: Subject to any disclaimer, the term of this patent is extended or adjusted under 35 U.S.C. 154(b) by 113 days.

(21) Appl. No.: 14/366,839

(22) PCT Filed: Dec. 17, 2012

(86) PCT No.: PCT/EP2012/075831
§ 371 (c)(1),
(2) Date: Jun. 19, 2014

(87) PCT Pub. No.: WO2013/092509
PCT Pub. Date: Jun. 27, 2013

(65) Prior Publication Data
US 2014/0370052 A1  Dec. 18, 2014

Related U.S. Application Data

(60) Provisional application No. 61/579,242, filed on Dec. 22, 2011.

(30) Foreign Application Priority Data

Dec. 22, 2011 (EP) ..................................... 11382392

(51) Int. Cl.
| | | |
|---|---|---|
| A61K 31/702 | (2006.01) | |
| A61K 31/7028 | (2006.01) | |
| A61K 31/7016 | (2006.01) | |
| G01N 33/569 | (2006.01) | |
| A61K 39/21 | (2006.01) | |
| A61K 8/14 | (2006.01) | |

(Continued)

(52) U.S. Cl.
CPC ...... *A61K 31/7028* (2013.01); *A61K 31/7016* (2013.01); *A61K 39/21* (2013.01); *G01N 33/56988* (2013.01); *A61K 8/14* (2013.01); *A61K 8/602* (2013.01); *A61K 8/68* (2013.01); *A61K 2039/5154* (2013.01); *C07K 16/2803* (2013.01); *C12N 2740/16034* (2013.01); *C12N 2740/16061* (2013.01); *G01N 2333/16* (2013.01)

(58) Field of Classification Search
CPC ........ A61K 31/7028; A61K 8/68; A61K 8/14; A61K 8/602; A61K 2039/5154; C07K 16/2803; C12N 2740/16061
See application file for complete search history.

(56) References Cited

U.S. PATENT DOCUMENTS

| | | | |
|---|---|---|---|
| 3,888,975 A | 6/1975 | Ramwell | |
| 3,916,898 A | 11/1975 | Robinson | |

(Continued)

FOREIGN PATENT DOCUMENTS

| | | |
|---|---|---|
| AU | 2010301762 A1 | 3/2012 |
| CA | 2050358 A1 | 3/1992 |

(Continued)

OTHER PUBLICATIONS

Berenson, C. S., et al., Sep. 1998, Gangliosides of monocyte-derived macrophages of adults with advanced HIV infection show reduced surface accessibility, J. Leukocyte Biol. 64:311-321.*
Seddiki, N., et al., Feb. 1994, A monoclonal antibody directed to sulfatide inhibits the binding of human immunodeficiency virus type 1 (HIV-1) envelope glycoprotein to macrophages but not their infection by the virus, Biochimica et biophysica acta, 1225(3):289-296 (abstract provided).*
Gait, M. J., and J. Karn, 1995, Progress in anti-HIV structure-based drug design, Tibtech 13:430-438.*
Hoenen, T., et al., May 2006, Ebola virus: unravelling pathogenesis to combat a deadly disease, Trends Mol. Med. 12(5):206-215.*
Lee, N., et al., "Expression of small interfering RNAs targeted against HIV-1 rev transcripts in human cells", "Nature Biotechnology", May 2002, pp. 500-505, vol. 20.
Li, M., et al., "Human immunodeficiency virus type 1 env clones from acute and early subtype B infections for standardized assessments of vaccine-elicited neutralizing antibodies", "Journal of Virology", Aug. 2005, pp. 10108-10125, vol. 79.
Lim, L., et al., "Vertebrate microRNA genes", "Science", Mar. 7, 2003, p. 1540, vol. 299.

(Continued)

*Primary Examiner* — Jeffrey Parkin
(74) *Attorney, Agent, or Firm* — Hultquist, PLLC; Steven J. Hultquist

(57) ABSTRACT

The present invention refers to methods and compositions to prevent viral entry into cells expressing the CD169/sialoadhesin surface receptor by inhibiting the coupling of the sialyllactose molecule contained in the viral membrane gangliosides to the CD 169/sialoadhesin receptor. The invention also pertains to vaccine compositions based on dendritic cells loaded with an antigen of interest whereby the vaccine is provided together with a composition capable of preventing viral entry into cells expressing the CD169/sialoadhesin. Moreover, the invention relates to diagnostic and therapeutic compositions that can be specifically delivered to enveloped virions wherein the diagnostic/therapeutic agent is coupled to CD169/sialoadhesin.

2 Claims, 19 Drawing Sheets

(51) Int. Cl.
  *C07K 16/28* (2006.01)
  *A61K 8/60* (2006.01)
  *A61K 8/68* (2006.01)
  *A61K 39/00* (2006.01)

(56) References Cited

U.S. PATENT DOCUMENTS

| | | | |
|---|---|---|---|
| 3,993,754 | A | 11/1976 | Rahman et al. |
| 4,016,043 | A | 4/1977 | Schuurs et al. |
| 4,145,410 | A | 3/1979 | Sears |
| 4,224,179 | A | 9/1980 | Schneider |
| 4,235,871 | A | 11/1980 | Papahadjopoulos et al. |
| 4,283,325 | A | 8/1981 | Berthet et al. |
| 4,313,734 | A | 2/1982 | Leuvering |
| 4,360,013 | A | 11/1982 | Barrows |
| 4,368,186 | A | 1/1983 | Vickery et al. |
| 4,371,518 | A | 2/1983 | Gazzani |
| 4,373,932 | A | 2/1983 | Gribnau et al. |
| 4,389,330 | A | 6/1983 | Tice et al. |
| 4,415,585 | A | 11/1983 | Joyce et al. |
| 4,499,154 | A | 2/1985 | James et al. |
| 4,522,803 | A | 6/1985 | Lenk et al. |
| 4,551,148 | A | 11/1985 | Riley, Jr. et al. |
| 4,557,934 | A | 12/1985 | Cooper |
| 4,588,578 | A | 5/1986 | Fountain et al. |
| 4,954,487 | A | 9/1990 | Cooper et al. |
| 4,961,931 | A | 10/1990 | Wong |
| 5,143,731 | A | 9/1992 | Viegas et al. |
| 5,185,155 | A | 2/1993 | Behan et al. |
| 5,208,031 | A | 5/1993 | Kelly |
| 5,231,112 | A | 7/1993 | Janoff et al. |
| 5,248,700 | A | 9/1993 | Lance |
| 5,286,634 | A | 2/1994 | Stadler et al. |
| 5,304,375 | A | 4/1994 | Marquardt et al. |
| 5,354,855 | A | 10/1994 | Cech et al. |
| 5,501,985 | A | 3/1996 | Baugher et al. |
| 5,554,372 | A | 9/1996 | Hunter |
| 5,698,411 | A | 12/1997 | Lucas et al. |
| 5,759,781 | A | 6/1998 | Ward et al. |
| 5,876,935 | A | 3/1999 | Pankratz et al. |
| 5,976,822 | A | 11/1999 | Landrum et al. |
| 6,809,186 | B1 | 10/2004 | Morseman et al. |
| 2003/0092091 | A1 | 5/2003 | Abrahamson et al. |
| 2005/0255042 | A1 | 11/2005 | Lam et al. |
| 2006/0034837 | A1 | 2/2006 | Bergmann |

FOREIGN PATENT DOCUMENTS

| | | |
|---|---|---|
| EP | 0316882 A2 | 5/1989 |
| EP | 0457127 A2 | 11/1991 |
| EP | 0475664 A1 | 3/1992 |
| EP | 1168924 A1 | 1/2002 |
| EP | 2060257 A1 | 5/2009 |
| FR | 2666587 A1 | 3/1992 |
| JP | 201256904 A | 3/2012 |
| WO | 9320185 A1 | 10/1993 |
| WO | 9321948 A1 | 11/1993 |
| WO | 9728816 A1 | 8/1997 |
| WO | 9833572 A1 | 8/1998 |
| WO | 0057705 A1 | 10/2000 |
| WO | 0248167 A1 | 6/2002 |
| WO | 2004054622 A1 | 7/2004 |
| WO | 2005026322 A2 | 3/2005 |
| WO | 2006107617 A2 | 10/2006 |
| WO | 2007046893 A2 | 4/2007 |
| WO | 2007112193 A2 | 10/2007 |
| WO | 2011040361 A1 | 4/2011 |

OTHER PUBLICATIONS

Lim, L., et al., "The microRNAs of Caenorhabditis elegans", "Genes & Development", Apr. 2, 2003, pp. 991-1008, vol. 17.
Lingwood, D., et al., "Cholesterol modulates glycolipid conformation and receptor activity", "Nature Chemical Biology", Apr. 3, 2011, pp. 260-262, vol. 7.
Loewe, S., et al., "Ueber Kombinationswirkungen", "Naunyn-Schmiedebergs Archiv fuer experimentelle Pathologie und Pharmakologie", Jul. 1926, pp. 313-326, vol. 114, No. 5-6.
Loewe, S., et al., "Ueber Kombinationswirkungen", "Naunyn-Schmiedebergs Archiv fuer experimentelle Pathologie und Pharmakologie", Jul. 1926, pp. 313-326 (English Abstract), vol. 114, No. 5-6.
Lorizate, M., et al., "Probing HIV-1 membrane liquid order by Laurdan staining reveals producer cell-dependent differences", "J. Biol. Chem.", Jun. 24, 2009, pp. 22238-22247, vol. 284, No. 33.
Mannering, S., et al., "A sensitive method for detecting proliferation of rare autoantigen-specific human T cells", "J. Immunol. Methods", Dec. 2003, pp. 173-183, vol. 283.
Mannino, Raphael J., et al., "Liposome Mediated Gene Transfer", "BioTechniques", Jul./Aug. 1988, pp. 682-690, vol. 6, No. 7.
May, A., et al., "Crystal structure of the N-terminal domain of sialoadhesin in complex with 3' sialyllactose at 1.85 A resolution", "Mol Cell", Apr. 1998, pp. 719-728, vol. 1.
Mayer, L., et al., "Vesicles of variable sizes produced by a rapid extrusion procedure", "Biochim. Biophys. Acta", Jun. 13, 1986, pp. 161-168, vol. 858.
Mellman, I., et al., "Dendritic cells: specialized and regulated antigen processing machines", "Cell", Aug. 10, 2001, pp. 255-258, vol. 106.
Nakane, P., et al., "Peroxidase-labeled antibody. A new method of conjugation.", "The Journal of Histochemistry and Cytochemistry", Dec. 1974, pp. 1084-1091, vol. 22, No. 12.
Needleman, S., et al., "A general method applicable to the search for similarities in the amino acid sequence of two proteins", "J. Mol. Biol.", Mar. 1970, pp. 443-453, vol. 48.
Nicolau, C., et al., "Liposomes as carriers of DNA", "Crit. Rev. Ther. Drug. Carrier Syst.", 1989, pp. 239-271, vol. 6, No. 3.
Novak, E., et al., "MHC class II tetramers identify peptide-specific human CD4+ T cells proliferating in response to influenza A antigen", "J. Clin. Invest.", Dec. 15, 1999, pp. R63-R67, vol. 104.
O'Doherty, U., et al., "Dendritic cells freshly isolated from human blood express CD4 and mature into typical immunostimulatory dendritic cells after culture in monocyte-conditioned medium", "J. Exp. Med.", Sep. 1, 1993, pp. 1067-1076, vol. 178.
Paglia, P., et al., "Immortalized dendritic cell line fully competent in antigen presentation initiates primary T cell responses in vivo", "J. Exp. Med.", Dec. 1, 1993, pp. 1893-1901, vol. 178.
Pearson, W., et al., "Improved tools for biological sequence comparison", "Proc Natl Acad Sci USA", Apr. 1988, pp. 2444-2448, vol. 85.
Pfister, G., et al., "Release Characteristics of Herbicides From Ca Alginate Gel Formulations", "Journal of Controlled Release", 1986, pp. 229-233, vol. 3.
Platt, C., et al., "Mature dendritic cells use endocytic receptors to capture and present antigens", "Proc. Natl. Acad. Sci. USA", Feb. 8, 2010, pp. 4287-4292, vol. 107.
Rempel, H., et al., "Sialoadhesin binds HIV-1 and is elevated in monocytes from subjects with high viral load", "7th International Symposium on NeuroVirology", May 31-Jun. 3, 2006, pp. 69-70, No. P163.
Romani, N., et al., "Proliferating dendritic cell progenitors in human blood", "J. Exp. Med.", Jul. 1, 1994, pp. 83-93, vol. 180.
Sallusto, F., et al., "Efficient presentation of soluble antigen by cultured human dendritic cells is maintained by granulocyte/macrophage colony-stimulating factor plus interleukin 4 and downregulated by tumor necrosis factor alpha", "J. Exp. Med.", Apr. 1, 1994, pp. 1109-1118, vol. 179.
Saville, B., et al., "A site-specific self-cleavage reaction performed by a novel RNA in neurospora mitochondria", "Cell", May 19, 1990, pp. 685-696, vol. 61, No. 4.
Saville, B., et al., "RNA-mediated ligation of self-cleavage products of a Neurospora mitochondrial plasmid transcript", "Proc. Natl. Acad. Sci. USA", Oct. 1, 1991, pp. 8826-8830, vol. 88.
Sessa, G., et al., "Incorporation of Lysozyme into Liposomes", "The Journal of Biological Chemistry", Jul. 10, 1970, pp. 3295-3301, vol. 245, No. 13.

(56) References Cited

OTHER PUBLICATIONS

Shugars, D., et al., "Analysis of human immunodeficiency virus type 1 nef gene sequences present in vivo", "Journal of Virology", Aug. 1993, pp. 4639-4650, vol. 67.
Simons, K., et al., "Membrane organization and lipid rafts", "Cold Spring Harb Perspect Biol", Oct. 1, 2011, pp. 117, vol. 3, No. a004697.
Smith, T., et al., "Comparison of biosequences", "Advances in Applied Mathematice ", Dec. 1981, pp. 482-489, vol. 2, No. 4.
Symons, R., "Small catalytic RNAs", "Annu. Rev. Biochem.", 1992, pp. 641-671, vol. 61.
Tatusova, T., et al., "BLAST 2 Sequences, a new tool for comparing protein and nucleotide sequences", "FEMS Microbiology Letters", May 15, 1999, pp. 247-250, vol. 174.
Taylor, B., et al., "The Challenge of HIV-1 Subtype Diversity", "N Engl J Med.", Apr. 10, 2008, pp. 1590-1602, vol. 358, No. 15.
Taylor, B., et al., "The Challenge of HIV-1 Subtype Diversity (Correction)", "N Engl J Med.", Oct. 30, 2008, pp. 1965-1966, vol. 359.
Tran, N., et al., "Expressing functional siRNAs in mammalian cells using convergent transcription", "BMC Biotechnol.", Nov. 6, 2003, pp. 19, vol. 3.
Uhlenbeck, O., "A small catalytic oligoribonucleotide", "Nature", Aug. 13, 1987, pp. 596-600, vol. 328.
Vinson, M., et al., "Characterization of the sialic acid-binding site in sialoadhesin by site-directed mutagenesis", "J. Biol. Chem.", Apr. 19, 1996, pp. 9267-9272, vol. 271.
Von Seggern, C., et al., "Study of peptide-sugar non-covalent complexes by infrared atmospheric pressure matrix-assisted laser desorption/ionization", "Jouranl of Mass Spectrometry", Jul. 2004, pp. 736-742, vol. 39.
Wagner, R., et al., "Antisense gene inhibition by oligonucleotides containing C-5 propyne pyrimidines", "Science", Jun. 4, 1993, pp. 1510-1513, vol. 260.
Wang, J., et al., "Stable and controllable RNA interference: Investigating the physiological function of glutathionylated actin", "Proc. Natl. Acad. Sci. USA", Apr. 15, 2003, pp. 5103-5106, vol. 100, No. 9.
Woo, J., et al., "Isolation, phenotype, and allostimulatory activity of mouse liver dendritic cells", "Transplantation", Aug. 27, 1994, pp. 484-491, vol. 58, No. 4.
Zeng, Y., et al., "Sequence requirements for micro RNA processing and function in human cells", "RNA", Jan. 9, 2003, pp. 112-113, vol. 9.
Zheng, L., et al., "An approach to genomewide screens of expressed small interfering RNAs in mammalian cells", "Proc. Natl. Acad. Sci. USA", Jan. 6, 2004, pp. 135-140, vol. 101, No. 1.
Lee, R., et al., "An extensive class of small RNAs in Caenorhabditis elegans", "Science", Oct. 26, 2001, pp. 862-864, vol. 294.
Adler, M., "Range and Natural History of Infection", "British Medical Journal", May 2, 1987, pp. 71145-1147, vol. 294.
Arshady, R., "Styrene Based Polymer Supports Developed by Suspension Polymerization", "La Chimica e L'Industria", Sep. 1988, pp. 70-75, vol. 70, No. 9.
Bartel, D., "MicroRNAs: genomics, biogenesis, mechanism, and function", "Cell", Jan. 23, 2004, pp. 281-297, vol. 116.
Betts, M., et al., "Sensitive and viable identification of antigen-specific CD8+ T cells by a flow cytometric assay for degranulation", "J. Immunol Methods", Oct. 1, 2003, pp. 65-78, vol. 281.
Boettcher, C., et al., "Analytica Chimica Acta", 1961, pp. 203-204, vol. 24.
Brenchley, J., et al., "Microbial translocation is a cause of systemic immune activation in chronic HIV infection", "Nature Medicine", Nov. 19, 2006, pp. 1364-1371, vol. 12, No. 12.
Chan, R., et al., "Retroviruses Human Immunodeficiency Virus and Murine Leukemia Virus are Enriched in Phosphoinositides", "Journal of Virology", Nov. 2008, pp. 11228-11238, vol. 82, No. 22.
Chattopadhyay, P., et al., "A live-cell assay to detect antigen-specific CD4+ T cells with diverse cytokine profiles", "Nature Medicine", Oct. 2005, pp. 1113-1117, vol. 11, No. 10.

Chou, T., et al., "Quantitative analysis of dose-effect relationships: the combined effects of multiple drugs or enzyme inhibitors", "Adv Enzyme Regul.", 1984, pp. 27-55, vol. 22.
Clouet-D'Orval, B., et al., "Kinetic characterization of two I/II format hammerhead ribozymes", "RNA", May 1996, pp. 483-491, vol. 2.
Collins, R., et al., "Reaction conditions and kinetics of self-cleavage of a ribozyme derived from Neurospora VS RNA", "Biochemistry", Mar. 23, 1993, pp. 2795-2799, vol. 32.
Delputte, P., et al., "Porcine arterivirus infection of alveolar macrophages is mediated by sialic acid on the virus", "Journal of Virology", Aug. 2004, pp. 8094-8101, vol. 78, No. 15.
Delputte, P., et al., "Porcine Sialoadhesin (CD169/Siglec-1) Is an Endocytic Receptor that Allows Targeted Delivery of Toxins and Antigens to Macrophages", "PloS One", Feb. 16, 2011, pp. e16827, vol. 6, No. 2.
Delrue, I., et al., "Susceptible cell lines for the production of porcine reproductive and respiratory syndrome virus by stable transfection of sialoadhesin and CD163", "BMC Biotechnology ", Jun. 29, 2010, p. 48, vol. 10.
Drutman, S., et al., "Dendritic cells continue to capture and present antigens after maturation in vivo", "J. Immunol.", Aug. 15, 2010, pp. 2140-2146, vol. 185, No. 4.
Frentsch, M., et al., "Direct access to CD4+ T cells specific for defined antigens according to CD154 expression", "Nature Medicine", Oct. 2005, pp. 1118-1124, vol. 11, No. 10.
Gomez, C., et al., "Generation and immunogenicity of novel HIV/AIDS vaccine candidates targeting HIV-1 Env/Gag-Pol-Nef antigens of Glade C", "Vaccine", Dec. 6, 2006, pp. 1969-1992, vol. 25.
Goujon, C., et al., "With a little help from a friend: increasing HIV transduction of monocyte-derived dendritic cells with virion-like particles of SIV(MAC)", "Gene herapy", Mar. 9, 2006, pp. 991-994, vol. 13.
Hartnell, A., et al., "Characterization of human sialoadhesin, a sialic acid binding receptor expressed by resident and inflammatory macrophage populations", Jan. 1, 2001, pp. 288-296, vol. 97, No. 1.
Haseloff, J., et al., "Simple RNA enzymes with new and highly specific endoribonuclease activities", "Nature", Aug. 18, 1988, pp. 585-591, vol. 334.
Hjerten, S., "The Preparation of Agarose Spheres for Chromatography of Molecules and Particles", "Biochim. Biophys. Acta", Mar. 30, 1964, pp. 393-398, vol. 79.
Holford, N., et al., "Understanding the dose-effect relationship: clinical application of pharmacokinetic-pharmacodynamic models", "Clinical Pharmacokinetics", Nov.-Dec. 1981, pp. 429-453, vol. 6.
Inaba, K., et al., "Isolation of dendritic cells", "Current Protocols in Immunology", May 2001, Chapter 3, Unit 3.7.
Ishikawa, E., "Enzyme-labeling of antibodies and their fragments for enzyme immunoassay and immunohistochemical staining", "Journal of Immunoassay", 1983, pp. 209-327, vol. 4, No. 3.
Izquierdo-Useros, N., et al., "Maturation of Blood-Derived Dendritic Cells Enhances Human Immunodeficiency Virus Type 1 Capture and Transmission", "Journal of Virology", Jul. 2007, pp. 7559-7570, vol. 81, No. 14.
Izquierdo-Useros, N., et al., "Capture and transfer of HIV-1 particles by mature dendritic cells converges with the exosome-dissemination pathway", "Blood", Mar. 19, 2009, pp. 2732-2741, vol. 113, No. 12.
Izquierdo-Useros, N., et al., "Sialyllactose in viral membrane gangliosides is a novel molecular recognition pattern for mature dendritic cell capture of HIV-1", "PLoS Biology", Apr. 24, 2012, pp. e1001315, vol. 10, No. 4.
Jeffries, A., et al., "A catalytic 13-mer ribozyme", "Nucleic Acids Res.", Feb. 25, 1989, pp. 1371-1377, vol. 17, No. 4.
Kalvodova, L., et al., "The lipidomes of vesicular stomatitis virus, semliki forest virus, and the host plasma membrane analyzed by quantitative shotgun mass spectrometry", "Journal of Virology", May 27, 2009, pp. 7996-8003, vol. 83, No. 16.
Kaykas, A., et al., "A plasmid-based system for expressing small interfering RNA libraries in mammalian cells", "BMC Cell Biology", Apr. 2004, pp. 111, vol. 5:16.

(56) References Cited

OTHER PUBLICATIONS

Lagos-Quintana, M., et al., "Identification of novel genes coding for small expressed RNAs", "Science", Oct. 26, 2001, pp. 853-858, vol. 294.

Lagos-Quintana, M., et al., "Identification of Tissue-Specific MicroRNAs from Mouse", "Current Biology", Apr. 30, 2002, pp. 735-739, vol. 12.

Lagos-Quintana, M., et al., "New microRNAs from mouse and human", "RNA", Feb. 2003, pp. 175-179, vol. 9.

Lampe, M., et al., "Double-labelled HIV-1 particles for study of virus-cell interaction", "Virology", Nov. 9, 2006, pp. 92-104, vol. 360.

Lau, N., et al., "An abundant class of tiny RNAs with probable regulatory roles in Caenorhabditis elegans", "Science", Oct. 2001, pp. 858-862, vol. 294.

DeMarco, M., et al., "Atomic-resolution conformational analysis of the Gm3 ganglioside in a lipod bilayer and its implications fpr ganglioside-protein recognition at membrane surfaces", "Glycobiology", Dec. 4, 2008, pp. 344-355 (2009), vol. 19, No. 4, Publisher: Oxford University Press.

Ramolho-Santos, J., et al., "The Role of Target Membrane Sialic Acid Residues in the Fusion Activity of the Influenza Virus: The Effect of Two Types of Ganglioside on the Kinetics of Membrane Merging", "Cellular & Molecular Biology Letters", 2004, pp. 337-351, vol. 9.

Sinibaldi, G., et al., "Gangliosides in Early Interactions between Vesicular Stomatitis Virus and CER Celles", "Microbiologica", 1985, pp. 355-365, vol. 8, No. 4.

Yanagihara, K., et al., "Activation of human T lymphocytes by ganglioside-containing liposomes", "Glycoconjugate Journal", 1999, pp. 59-65, vol. 16, Publisher: Kluwer Academic Publishers.

Fantini, J., et al., "Role of glycosphingolipid microdomains in CD4-dependent HIV-1 fusion", "Glycoconjugate Journal", Mar. 1, 2000, pp. 199-204, vol. 17.

Okada, N., et al., "Human IgM Monoclonal Antibody to Ganglioside GM2 and Complement Suppress Virus Propagation in Ex Vivo Cultures of Lymphocytes from HIV-1 Infected Patients", "Microbiology and Immunology", Jan. 1, 1999, pp. 723-727, vol. 43, No. 7.

Rawat, S. S., et al., "Elevated Expression of GM3 in Receptor-Bearing Targets Confers Resistance to Human Immunodeficiency Virus Type 1 Fusion", "Journal of Virology", Jul. 2004, pp. 7360-7368, vol. 78, No. 14.

Wu, X., et al., "The IgM Antibody Level against Ganglioside GM2 Correlates to the Disease Status of HIV-1-Infected Patients", "Microbiology and Immunology", Jan. 1, 2000, pp. 405-410, vol. 44, No. 5.

* cited by examiner

METHOD FOR BLOCKING HIV ENTRY INTO DENDRITIC CELLS BY INHIBITING SIALOADHESIN-SIALYLLACTOSE BINDING INTERACTIONS WITH GANGLIOSIDES

CROSS-REFERENCE TO RELATED APPLICATIONS

This application is a U.S. national phase under the provisions of 35 U.S.C. §371 of International Patent Application No. PCT/EP12/75831 filed Dec. 17, 2012, which in turn claims priority of European Patent Application No. EP11382392.6 filed Dec. 22, 2011 and U.S. Provisional Patent Application No. 61/579,242 filed Dec. 22, 2011. The disclosures of such international patent application and European and U.S. priority patent applications are hereby incorporated herein by reference in their respective entireties, for all purposes.

FIELD OF THE INVENTION

The present invention refers to method for preventing viral entry into cells expressing the CD169 cell surface receptor by inhibiting the coupling of sialyllactose molecules in the viral membrane gangliosides to the CD169 receptor. The invention also relates to inhibitors of this coupling, as well as pharmaceutical compositions containing the inhibitors of the invention, their methods of preparation and diagnostic applications.

BACKGROUND OF THE INVENTION

Dendritic cells (DCs) capture pathogens in the mucosa and then migrate to the secondary lymphoid tissue, where they acquire the mature phenotype required to induce efficiently adaptive immune responses. The potential role of mature DCs (mDCs) uptake for antigen presentation implies efficient antigen capture and transfer into the antigen presentation pathway. Down regulation of endocytosis is considered a hallmark of DC maturation, but there is increasing evidence that under inflammatory conditions mDCs capture, process, and present antigens without exclusively relying on prior pathogen exposure. See Mellman I, et al., Cell 2001; 106:255-258, Platt C, et al., Proc. Natl. Acad. Sci. USA 2010; 107:4287-4292 and Drutman S, et al., J. Immunol. 2010; 185:2140-2146. This scenario might be particularly relevant in chronic infections, such as the one caused by HIV-1, where increased translocation of bacteria from the intestinal lumen could stimulate DCs systemically and contribute to sustained antiviral immune responses. See Brenchley J, et al., Nat. Med. 2006; 12:1365-1371.

Paradoxically, HIV-1 capture into mDCs appears to also critically enhance viral dissemination in lymphoid tissue by efficient presentation of infectious virus to T-cells in the DC-T-cell synapse, thus promoting pathogenesis and disease progression through trans-infection. In vitro studies have shown that, when HIV is incubated at low MOI with T cells, inclusion of DC results in much more efficient infection of the T cells. The mechanism for trans-infection has been a subject of some controversy. An HIV-1 gp120-independent mechanism of viral binding and uptake that is upregulated upon DC maturation has been previously identified in the art. See Izquierdo-Useros N, J. Virol. 2007; 81: 7559-7570. In addition, HIV-1 Gag eGFP-expressing fluorescent virus-like particles ($VLP_{HIV\text{-}Gag\text{-}eGFP}$) follow the same trafficking route as wild type HIV-1 in mDCs, and hence share a common molecular pattern that governs entry into mDCs. See Izquierdo-Useros N, et al., Blood 2009; 113:2732-2741. However, the precise mechanism through which HIV-1 is internalized and accumulated into mDCs was unknown until now.

Accordingly, the identification of the mechanism by which uptake of HIV by DCs takes place would allow the development of tools useful for preventing said uptake, thus reducing the trans-infection of CD4+ T cells by DCs.

SUMMARY OF THE INVENTION

In a first aspect, the invention relates to an inhibitor of the interaction between sialoadhesin and sialyllactose for use in the treatment or prevention of a disease associated with an infection caused by an enveloped virus.

In another aspect, the invention relates to a composition or kit-of-parts comprising an antigen-loaded antigen-presenting cell and an inhibitor of the interaction between sialoadhesin and sialyllactose.

In a further aspect, the invention relates to a method for detecting or isolating an enveloped virus in a sample comprising:
(i) contacting said sample with sialoadhesin or a functionally equivalent variant thereof substantially preserving its ability to bind sialyllactose, and
(ii) detecting or isolating the virus bound to said sialoadhesin or a functionally equivalent variant thereof.

In a further aspect, the invention relates to a kit comprising immobilized sialoadhesin or a functionally equivalent variant thereof substantially preserving its ability to bind sialyllactose.

In another aspect, the invention relates to a conjugate comprising sialoadhesin or a functionally equivalent variant thereof substantially preserving its ability to bind sialyllactose and a therapeutic or diagnostic agent.

In yet another aspect, the invention relates to an in vitro method for delivering a compound of interest to an antigen-presenting cell which comprises contacting said antigen-presenting cell with a lipid microparticle comprising said compound of interest wherein said lipid particle comprises at least a molecule containing a sialyllactose moiety.

DETAILED DESCRIPTION OF THE INVENTION

Figure 1A:
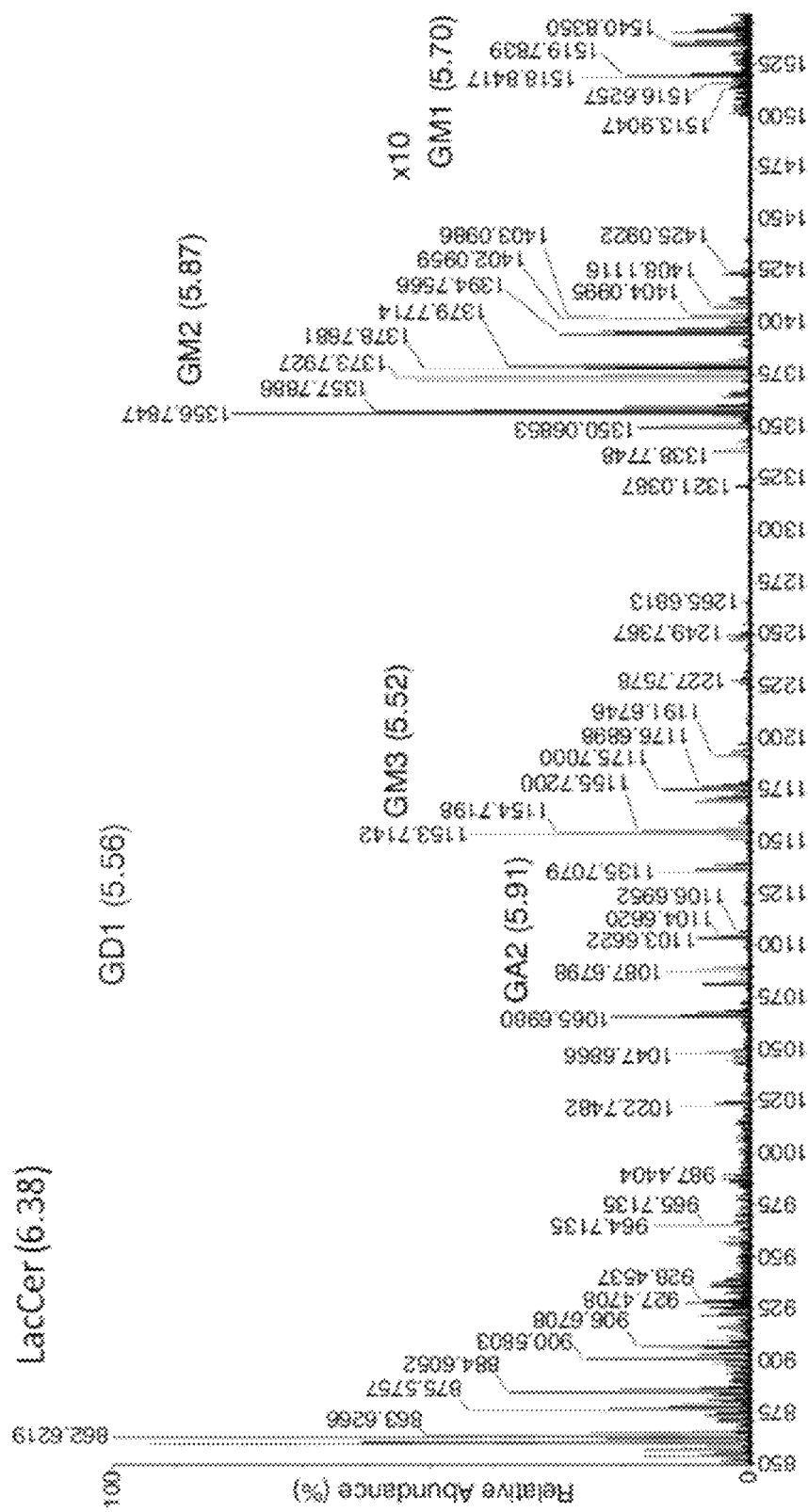
FIG. 1. Gangliosides are required for viral capture mediated by mDC. Ganglioside detection in lipid extracts from MT4 derived $HIV_{NL4.3}$. (A) Partial mass spectra (from 850 to 1550 amu) corresponding to the 5.3 and 6.5 min range of a chromatogram representative of three different viral isolations obtained by UPLC/TOF ESI(+) analysis. For each compound of interest identified, its [M+H]+ and [M+Na]+ ions are indicated. The retention time of each compound is given next to its abbreviation. The selected time range corresponds to the N hexadecanoyl (N-C16) species. (B) Exact mass ion cluster obtained at 5.56 min for GD1. (C) Exact mass ion cluster corresponding to the formula C82H144N4O39 with a charge state of 2. The N-C22, N-C24 and N-C24:1 species were also observed. (D) Comparative mDC capture of $VLP_{HIV\text{-}Gag\text{-}eGFP}$ and distinct fluorescent $LUV_{HIV\text{-}tRed}$ containing Cer, GM3, GM2, GM1 or PS. A total of 2×10⁵ DCs were pulsed for 4 h at 37° C. with 100 µM of LUV or 75 ng of $VLP_{HIV\text{-}Gag\text{-}eGFP}$ Gag in 0.2 ml, washed with PBS and asses by FACS to obtain the percentage of tRed or eGFP positive cells. Data show mean values and SEM from five independent experiments including cells from at least six donors. Mature DCs capture significantly higher amounts of GM3-containing $LUV_{HIV\text{-}tRed}$ than Cer or Ø LUV$_{HIV-tRed}$ (P<0.0001, paired t test). Mature DCs capture significantly higher amounts of GM1-containing LUV$_{HIV-tRed}$ than negatively charged PS-LUV$_{HIV-tRed}$ (P=0.0081, paired t test). (E) Capture competition between 75 ng of VLP$_{HIV-Gag-eGFP}$ Gag and decreasing amounts (μM) of GM2-containing LUV$_{HIV-tRed}$. As controls, we used the maximum concentration of LUV$_{HIV-tRed}$ (100 μM) with or without Cer. Cells were incubated for 4 hours at 37° C., washed and analyzed by FACS to establish the percentage of eGFP- and tRed-positive cells. Data show mean values and SEM from three independent experiments including cells from at least four donors. mDCs capture fewer VLP$_{HIV-Gag}$-eGFP in the presence of higher amounts of GM2-containing LUV$_{HIV-tRed}$ (P<0.0001, paired t test).
Figure 1:
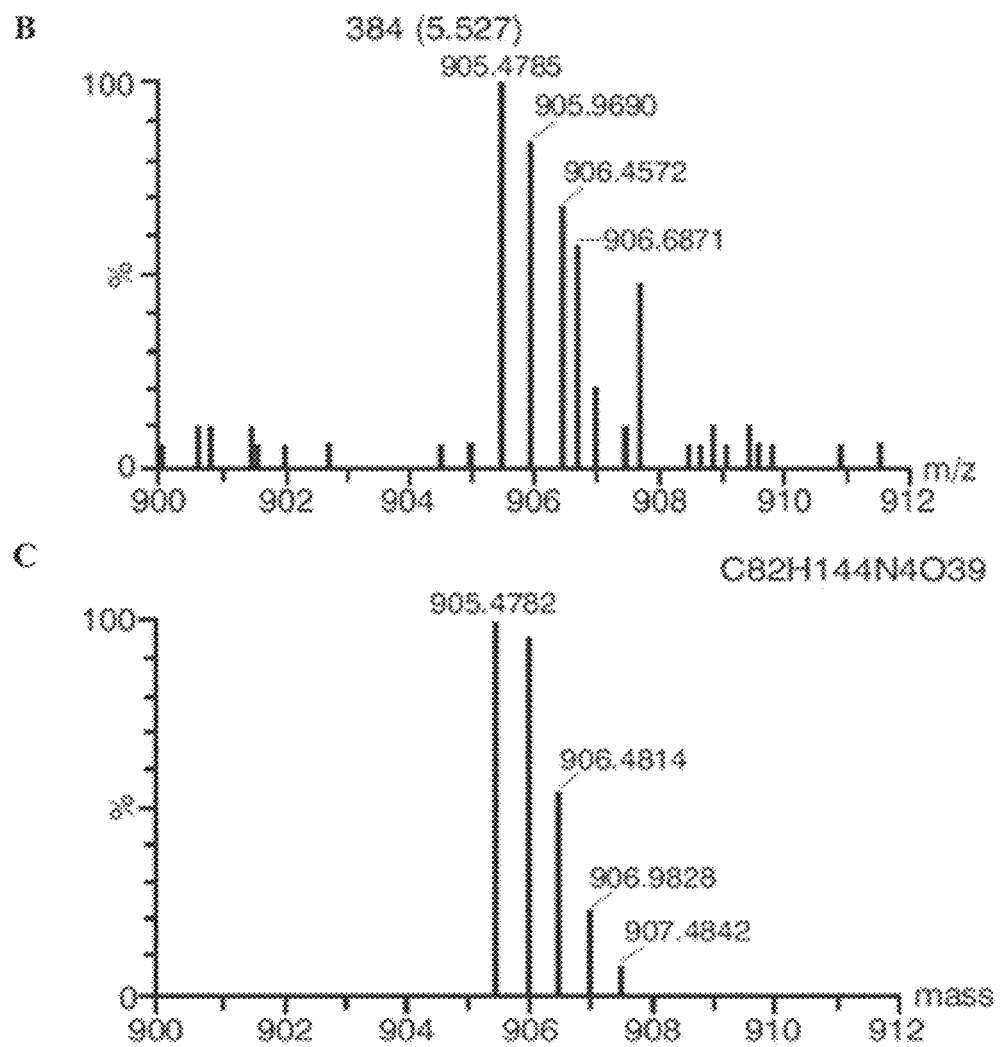
Figure 1:
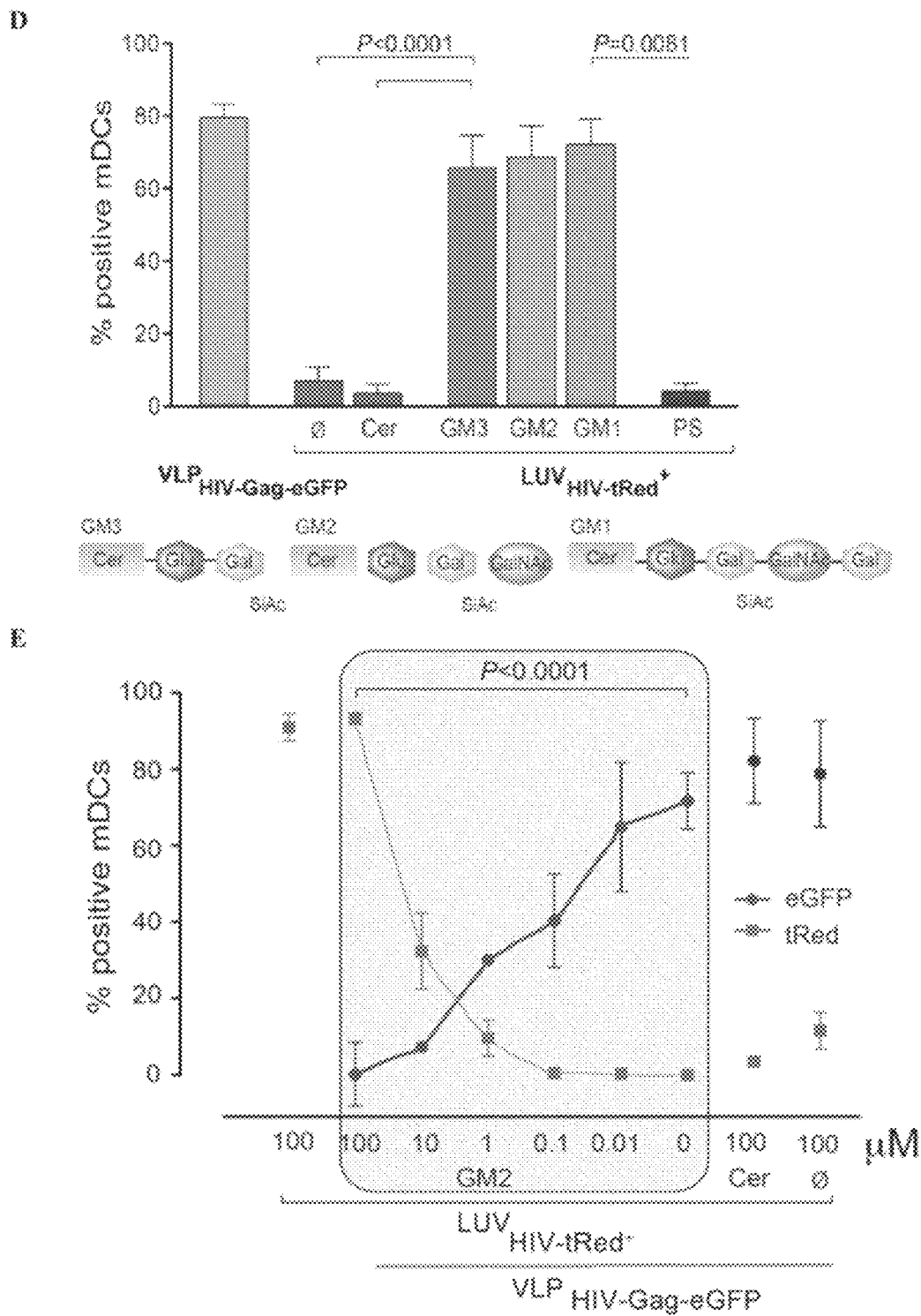

The present invention identifies clearly a novel role for sialylated gangliosides in the membrane of viruses or vesicles as determinants for specific capture by mDCs. This capture is dependent on an exposed sialyllactose moiety, which is identified herein for the first time as a novel pathogen-associated molecular pattern. Gangliosides are a significant component of the plasma membrane lipidome suggesting that all enveloped viruses, which bud from the plasma membrane of infected cells, may be captured into mDCs by the reported mechanism unless they exclude sialyllactose containing gangliosides.

The efficient capture of ganglioside-carrying vesicles or virions support a model such as the one disclosed in the present invention, where a specific receptor present on the cell surface of mDCs (and possibly other cells), such as the CD169 cell surface receptor, recognizes the sialyllactose moiety on the virion or vesicle membranes. Specific recognition of vesicular gangliosides would then trigger uptake into an intracellular compartment. Subsequently, internalized material may either be recycled to the surface (as in HIV-1 transmission to T-cells) or could be fed into the antigen presentation pathway.

1. Definitions of General Terms and Expressions

The term "AIDS", as used herein, refers to the symptomatic phase of HIV infection, and includes both Acquired Immune Deficiency Syndrome (commonly known as AIDS) and "ARC," or AIDS-Related Complex. See Adler M, et al., Brit. Med. J. 1987; 294: 1145-1147. The immuno logical and clinical manifestations of AIDS are well known in the art and include, for example, opportunistic infections and cancers resulting from immune deficiency.

The term "antibody", as used herein, refers to a protein consisting of one or more proteins substantially encoded by all or part of the recognized immunoglobulin genes, including but not limited to polyclonal antibodies, monoclonal antibodies, and antigen-binding fragments thereof such as, for instance, $F(ab')_2$ and Fab fragments, and single chain antibodies. The term antibody includes any type of known antibody, such as, for example, polyclonal antibodies, monoclonal antibodies and genetically engineered antibodies, such as chimeric antibodies, humanized antibodies, primatized antibodies, human antibodies and bispecific antibodies.

The term "anti-HIV agent", "HIV-inhibiting agent" and "HIV antiviral agent", as used herein, refers to any compound or a pharmaceutically acceptable salt thereof which is capable of inhibiting the replication of HIV in a cell, such as a cell in a mammal or which is effective in treating, preventing, or delaying the onset or progression of HIV infection or AIDS or diseases or conditions arising therefrom or associated therewith. Suitable anti-HIV agents for use according to the present invention include, without limitation, HIV protease inhibitors, a HIV reverse transcriptase inhibitor, HIV entry inhibitors and HIV immunogens.

The term "antigen-binding region" of an antibody, as used herein, includes also a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins") and minimal recognition units consisting of the amino acid residues that mimic the hypervariable region.

The term "antigen loading", as used herein, refers to a method of delivering antigens to dendritic cells by incubating dendritic cells or progenitor cells with the peptide, polypeptide, lipopeptide, DNA (naked or within a plasmid vector) or RNA; or with antigen-expressing recombinant bacterium or viruses (e.g. vaccinia, adenovirus or lentivirus) such that the antigenic epitopes thereof are loaded and expressed on the cell surface by MHC.

The term "antigen-presenting cell (APC)", as used herein, refers to any cell capable of processing and presenting an antigen via an MHC molecule (MHC class I or MHC class II molecules). The APC could be capable of processing and presenting an antigen via MHC class I and MHC class II molecules. In particular, antigen presenting cells comprise dendritic cells, macrophages, B cells, epithelial cells, fibroblasts, glial cells and additional cells identifiable by a skilled person. Preferably, APV are dendritic cells.

The term "antiretroviral agent", as used herein, includes any pharmacological, biological or cellular agent that has demonstrated the ability to a retrovirus.

The term "antisense nucleic acid" is intended to refer to the oligonucleotides complementary to the base sequences of oncogene-encoding DNA and RNA. Antisense nucleic acid, when expressed in a target cell, specifically bind to their target nucleic acid and interfere with transcription, RNA processing, transport and/or translation. Targeting double-stranded (ds) DNA with polynucleotides leads to triple-helix formation; targeting RNA will lead to double) helix formation.

The term "autologous", as used herein, refers to any material derived from a donor subject that is later reintroduced to the same individual.

The term "composition", as used herein, refers to a material composition that comprises at least two components, as well as any product resulting, directly or indirectly, from the combination of the different components in any quantity thereof. Those skilled in the art will observe that the composition may be formulated as a single formulation or may be presented as separate formulations of each of the components, which may be combined for joint use as a combined preparation. The composition may be a kit-of-parts wherein each of the components is individually formulated and packaged.

The term "comprising" or "comprises", as used herein, discloses also "consisting of" according to the generally accepted patent practice.

The term "conjugate", as used herein, refers to two or more compounds which are covalently linked together so that the function of each compound is retained in the conjugate.

The term "dendritic cell" (DC), as used herein, is an antigen-presenting cell existing in vivo, in vitro, ex vivo, or in a host or subject, or which can be derived from a hematopoietic stem cell or a monocyte. Dendritic cells and their precursors can be isolated from a variety of lymphoid organs (e.g. spleen, lymph nodes), as well as from bone marrow and peripheral blood. The DC has a characteristic morphology with thin sheets (lamellipodia) extending in multiple directions away from the dendritic cell body. Typically, dendritic cells express high levels of MHC and costimulatory (e.g. B7-1 and B7-2) molecules. Dendritic cells can induce antigen specific differentiation of T cells in vitro, and are able to initiate primary T cell responses in vitro and in vivo. The term "dendritic cells" includes differentiated dendritic cells, whether immature and mature dendritic cells. These cells can be characterized by expression of certain cells surface markers (e.g. CD11c, MHC class II, and at least low levels of CD80 and CD86). In addition, dendritic cells can be characterized functionally by their capacity to stimulate alloresponses and mixed lymphocyte reactions (MLR). The expression "dendritic cell preparation" refers to a composition that contains dendritic cells obtained from a subject in a media suitable for the pulsing of said cells.

The expression "disease associated with a HIV infection", as used herein, includes a state in which the subject has developed AIDS as well as a state in which the subject infected with HIV has not shown any sign or symptom of the disease. Thus, the compositions of the invention when administered to a subject that has no clinical signs of the infection can have a preventive activity, since they can prevent the onset of the disease. The compositions are capable of preventing or slowing the infection and destruction of healthy CD4+ T cells in such a subject. It also refers to the prevention and slowing the onset of symptoms of the acquired immunodeficiency disease such as extreme low CD4+ T cell count and repeated infections by opportunistic pathogens such as *Mycobacteria* spp., *Pneumocystis carinii*, and *Pneumocystis cryptococcus*. Beneficial or desired clinical results include, but are not limited to, an increase in absolute naïve CD4+ T-cell count (range 10-3520), an increase in the percentage of CD4+ T-cell over total circulating immune cells (range 1-50 percent), and/or an increase in CD4+ T-cell count as a percentage of normal CD4+ T-cell count in an uninfected subject (range 1-161 percent). "Treatment" can also mean prolonging survival of the infected subject as compared to expected survival if the subject did not receive any HIV targeted treatment.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The expression "disease associated with an infection caused by an enveloped virus", as used herein, includes without limitation:

1) Diseases caused by enveloped viruses belonging to the filoviridae family including, without limitation, Marburg virus disease (Marburg hemorrhagic fever or MHF), caused by Marburgvirus and Ebola virus disease (Ebola Hemorrhagic Fever or EHF), caused by Ebola virus, and 2) Diseases caused by an enveloped virus belonging to the retroviridae family. Other diseases caused by an enveloped virus infection include, without limitation, Dengue fever, Dengue hemorrhagic fever (DHF), yellow fever, dengue fever, acute and chronic hepatitis C, Venezuelan hemorrhagic fever, Brazilian hemorrhagic fever, Bolivian hemorrhagic fever, lymphocytic choriomeningitis, Lassa fever, hantavirus pulmonary syndrome (HPS), meningitis and influenza.

The term "enveloped virus", as used herein, refers to any animal virus which possesses an outer membrane or envelope, which is a lipid bilayer containing viral proteins, surrounding the virus capsid. Exemplary enveloped viruses include, but are not limited to, members of the poxyiridae, hepadnaviridae, togaviridae, arenaviridae, flaviviridae, orthomyxoviridae, paramyxoviridae, bunyaviridae, rhabdoviridae, filoviridae, coronaviridae, retroviridae and bornaviridae virus families.

The term "epitope", as used herein, refers to any protein determinant capable of specific binding to an immunoglobulin or of being presented by a Major Histocompatibility Complex (MHC) protein (e.g. Class I or Class II) to a T-cell receptor. Epitopic determinants are generally short peptides 5-30 amino acids long that fit within the groove of the MHC molecule that presents certain amino acid side groups toward the T cell receptor and has certain other residues in the groove (e.g. due to specific charge characteristics of the groove), the peptide side groups and the T cell receptor.

The term "ganglioside" or "sialogangliosides", as used herein, refers to glycosphingolipids which contain several monosaccharide units per molecule. Examples of suitable monosaccharide units which can be contained in the gangliosides or ganglioside derivatives are D-galactose, N-acetyl D-galactosamine, glucose and N-acetylneuraminic acid. Particular preference is given to gangliosides which are derivatives of sphingosine (2-amino-4-octadecene-1,3-diol, sphing-4-enine), with, in particular, sugar residues being bonded on by way of the oxygen on the C-1 and a short (in particular $C_2$-$C_{18}$) fatty acid, which can be saturated or unsaturated, being bonded by way of the nitrogen on the C-2. Preference is furthermore given to the gangliosides which comprise:

(i) N-acylsphingosine (ceramide), which has the general structure:

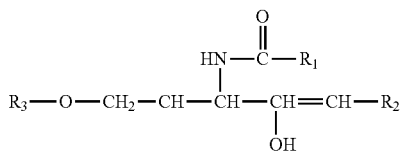

wherein $R_1$ is a long-chain fatty acid residue, in particular a $C_6$-$C_{30}$, more preferably a $C_8$-$C_{24}$, fatty acid residue, $R_2$ is a long-chain alkyl residue, in particular a $C_6$-$C_{30}$, more preferably a $C_8$-$C_{24}$ alkyl residue, and $R_3$ is H, and (ii) an oligosaccharide chain bearing one or more N-acetylneuraminic acid (e.g. N-acetylneuraminic acid, NANA, sialic acid) linked to the terminal primary hydroxyl group of the ceramide. The N-acetylneuraminic acid residue or residues may be coupled to the oligosaccharide by any possible position in the sialic acid and to any possible position in the oligosaccharide molecule. In a preferred embodiment, the N-acetylneuraminic acid is linked to the oligosaccharide by the hydroxyl group at position 2 of the sialic acid (the numbering of the sialic acid structure begins at the carboxylate carbon and continues around the chain). In another preferred embodiment, the sialic acid is linked to the oligosaccharide by the hydroxyl groups at positions 3 or 6 in the galactose residue which forms part of the oligosaccharide. In preferred embodiments, the "N-acetylneuraminic acid" forms α2,3-sialyl- or α2,6-sialyl-oligosaccharides.

The term "HIV", as used herein, include HIV-1 and HIV-2 and SIV. "HIV-1" means the human immunodeficiency virus type-1. HIV-1 includes but is not limited to extracellular virus particles and the forms of HIV-1 associated with HIV-1 infected cells. The HIV-1 virus may represent any of the known major subtypes (Classes A, B, C, D E, F, G and H) or outlying subtype (Group 0) including laboratory strains and primary isolates. "HIV-2" means the human immunodeficiency virus type-2. HIV-2 includes but is not limited to extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes but is not limited to extracellular virus particles and the forms of SIV associated with SIV infected cells.

The term "HIV immunogen", as used herein, refers to a protein or peptide antigen derived from HIV that is capable of generating an immune response in a subject. HIV immunogens for use according to the present invention may be selected from any HIV isolate (e.g. any primary or cultured HIV-1, HIV-2, or HIV-3 isolate, strain, or clade).

The term "HIV infection", as used herein, refers to the verified presence of an HIV antibody, HIV antigen, or HIV nucleic acid in a subject as demonstrated by the detection of the presence of virus using HIV tests known to those skilled in the art (e.g. HIV EIA, Western blot, PCR tests).

The term "immunogen", as used herein, refers to a substance or material (including antigens) that is able to induce an immune response alone or in conjunction with an adjuvant. As it will be understood, the immune response generated by the vaccine may be a humoral or a cellular immune response. The expression "humoral immune response", is used herein to describe an immune response against foreign antigen(s) that is mediated by T-cells and their secretion products. The "cellular immune response", is used herein to describe an immune response against foreign antigen(s) that is mediated by antibodies produced by B-cells. The vaccine is systemically or locally administered. The vaccine can be administered by means of a single administration, or with a boost by means of multiple administrations as has been previously described for the administration of the compositions of the invention. The terms "prevent," "preventing," and "prevention", as used herein, refer to a decrease in the occurrence of pathological cells in an animal. The prevention may be complete (e.g. the total absence of pathological cells in a subject). The prevention may also be partial, such that for example the occurrence of pathological cells in a subject is less than that which would have occurred without the present invention. Prevention also refers to reduced susceptibility to a clinical condition.

The expression "inhibitor of the interaction between sialoadhesin and sialyllactose", as used herein, refers to any molecule or compound which is capable of inhibiting the binding between sialoadhesin and sialyllactose or any other compound comprising sialyllactose. Inhibitors are capable of specifically binding to either of sialoadhesin and sialyllactose with an affinity that is higher than the affinity of the binding between sialoadhesin and sialyllactose. As used in the present invention, the expression "specific binding" refers to the capacity of a first molecule to bind specifically to a second molecule by means of the existence of complementarity between the three-dimensional structures of the two molecules with a substantially higher affinity for non-specific binding such that the binding between said first and second molecule preferably takes place before the binding of any of said molecules with respect to the other molecules present in the reaction mixture. It is understood that there is high affinity in the binding of two molecules when the complex resulting from said binding has a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

The term "interfering RNA", as used herein refers to a means of selective post-transcriptional gene silencing by destruction of specific mRNA by molecules that bind and inhibit the processing of mRNA, for example inhibit mRNA translation or result in mRNA degradation. Suitanble interfering RNA include, without limitation, siRNA, shRNA, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

The term "isolation", as used herein, refers to partial or complete removal of viral particles from the media in which they are produced.

The term "lectin", as used herein, refers to any protein different from an antibody and which is capable of binding to a carbohydrate or to a structure modified by a carbohydrate, including glycoproteins and glycosylated nanostructures.

The term "lipidic microvesicle" or "liposome", as used herein, refers to a microscopic vesicle comprising an outer lipid layer. The outer lipid layer could be a lipid monolayer or bilayer. When the outer lipid layer is a lipid monolayer, the liposomes are also referred to as micelles. Liposomes may have one or more lipid membranes. The invention contemplates both single-layered liposomes, which are referred to as unilamellar, and multi-layered liposomes, which are referred to as multilamellar.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes and Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. The term "molecule comprising a sialyllactose moiety", as used herein, refers to any molecule which contains within its structure a $\beta$-D-galactopyranosyl-($1\rightarrow 4$)-D-glucose moiety bound to a sialic acid moiety. In a preferred embodiment, the $\beta$-D-galactopyranosyl-($1\rightarrow 4$)-D-glucose moiety forms part of an oligosaccharide wherein the galactopyranosyl-($1\rightarrow 4$)-D-glucose moiety may form the terminal two monosaccharide residues in the chain or may be linked to further monosaccharide residues on both sides. The oligosaccharide containing the galactopyranosyl-($1\rightarrow 4$)-D-glucose moiety may contain at least 3, 4, 5, 6, 7, 8, 9, 10 or more monosaccharides residues. The oligosaccharide can be provided as such or form part of a ganglioside.

The term "% sequence identity", as used herein, is determined by comparing two optimally aligned sequences over a comparison window, where the fragment of the polypeptide or polynucleotide sequence in the comparison window may comprise additions or deletions (e.g. gaps or overhangs) as compared to the reference sequence (which does not comprise additions or deletions) for optimal alignment of the two sequences. The percentage is calculated by determining the number of positions at which the identical amino acid residue or nucleic acid residue occurs in both sequences to yield the number of matched positions, dividing the number of matched positions by the total number of positions in the comparison window and multiplying the result by 100 to provide the percentage of sequence identity. Algorithms to align sequences are known in the art. Optimal alignment of sequences for comparison can be conducted, for instance, by the Smith-Waterman local homology algorithm, by the Needleman-Wunsch homology alignment algorithm, by the Pearson-Lipman similarity search method, by computerized implementations of these algorithms or by manual alignment and visual inspection. See Smith T, Waterman M, Adv. Appl. Math. 1981; 2:482-489; Needleman S, Wunsch C, J. Mol. Biol. 1970; 48:443-453; Pearson W, Lipman D, Proc. Natl. Acad. Sci. USA 1988; 85:2444-2448; Tatusova T, Madden T, FEMS Microbiol. Lett. 1999; 174:247-250; the GAP, BESTFIT, FASTA and TFASTA programs, Wisconsin Genetics Software Package, Genetics Computer Group, Madison, Wis., US; Ausubel F, et al., Eds., "Short Protocols in Molecular Biology", 4th Ed. (John Wiley and Sons, Inc., New York, N.Y., US, 1997).

The terms "pharmaceutically acceptable carrier," "pharmaceutically acceptable diluent", "pharmaceutically acceptable excipient", or "pharmaceutically acceptable vehicle", used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed, and is compatible with other ingredients of the formulation. For example, the carrier for a formulation containing polypeptides would not normally include oxidizing agents and other compounds that are known to be deleterious to polypeptides.

The term "phospholipid", as used herein, refers to a lipid that contains one or more phosphate groups. Phospholipids are amphipathic in nature; that is, each molecule consists of a hydrophilic portion and a hydrophobic portion. Herein, the term "phospholipid" includes pharmaceutically acceptable salts and ester derivatives of such compounds. Phospholipids can be classified according to the type of alcohol in phosphoglycerides (or glycerophospholipids) when they carry a glycerol backbone and sphingolipids wherein the lipids contain sphingosine. Both classes are present in the biological membrane. Phosphoglycerides are the most abundant class of phospholipids found in nature and include, without limitation, phosphatidylcholine (e.g. lecithin), phosphatidylethanolamine, phosphatidylserine, phosphatidylinositol, phosphatidylglycerol, and cardiolipin. The structural diversity within each type of phosphoglyceride is due to the variability of the chain length and degree of saturation of the fatty acid ester groups.

The term "protease inhibitor", as used herein, refers to HIV-1 protease, an enzyme required for the proteolytic cleavage of viral polyprotein precursors (e.g. viral GAG and GAG Pol polyproteins), into the individual functional proteins found in infectious HIV-1.

The term "retrovirus", as used herein, refers to virus belonging to the Retroviridae family, which are characterized by being an RNA virus that is replicated in a host cell via the enzyme reverse transcriptase to produce DNA from its RNA genome.

The term "reverse transcriptase inhibitors", as used herein, refers to any compound which inhibits the activity of HIV-1 reverse transcriptase, the enzyme which catalyzes the conversion of viral genomic HIV-1 RNA into proviral HIV-1 DNA.

The term "ribozyme" refers to an RNA-based enzyme capable of targeting and cleaving particular base sequences in DNA or, more typically, RNA.

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

As used herein an "siRNA" refers to a nucleic acid that forms a double stranded

RNA, which double stranded RNA has the ability to reduce or inhibit expression of a gene or target gene when the siRNA is present or expressed in the same cell as the target gene, sEH. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length). The terms "sialoadhesin", "sialic acid binding Ig-like lectin 1", "siglec-1", CD169 are used herein interchangeably to refer to I-type lectin, composed of 17 immunoglobulin (Ig) domains, that binds to sialic acids forming a salt bridge between a highly conserved arginine residue and the carboxylate group of the sialic acid. See May A, et al., Mol. Cell. 1998; 1:719-728. Suitable sialoadhesin variants for use according to the present invention include the human sialoadhesin (described in the UniProt database under accession number Q9BZZ2), porcine sialoadhesin (described in the UniProt database under accession number A7LCJ3) and mouse sialoadhesin (described in the UniProt database under accession number Q62230.

The term "sialoadhesin inhibitor", as used herein, refers to any molecule which results in a decrease of the levels and/or activity of sialoadhesin. Inhibitors include, without limitation, molecules which lead to a reduction in the amount of sialoadhesin protein and molecules which result in a reduction in the amount of the mRNA encoding sialoadhesin.

The term "sialyllactose", as used herein, refers to a molecule comprising a lactose moiety (β-D-galactopyranosyl-(1→4)-D-glucose) bound to a sialic acid moiety. The sialic acid may be coupled to the lactose by any possible position in the sialic acid and to any possible position in the lactose molecule. In a preferred embodiment, the sialic acid is linked to the lactose by the hydroxyl group at position 2 of the sialic acid (the numbering of the sialic acid structure begins at the carboxylate carbon and continues around the chain). In another preferred embodiment, the sialic acid is linked to the lactose by the hydroxyl groups at positions 3 or 6 in the lactose molecule. In preferred embodiments, the "sialyllactose" is α2,3-sialyl-lactose or α2,6-sialyl-lactose. Sialyllactose, may be of eukaryotic or prokaryotic origin. Preferably, sialyllactose is of eukaryotic origin. The eukaryotic or prokaryotic cell may be pathogenic or non-pathogenic.

The term "subject", as used herein, is meant to include all animals shown to or expected to have antigen presenting cells. In particular embodiments, the subject is a mammal, a human or nonhuman primate, a dog, a cat, a horse, a cow, other farm animals, or a rodent (e.g. mice, rats, guinea pig). The term "subject" and "individual" are used interchangeably herein.

The term "treatment", as used herein, refers to any type of therapy, which aims at terminating, preventing, ameliorating or reducing the susceptibility to a clinical condition as described herein. In a preferred embodiment, the term treatment relates to prophylactic treatment (i.e. a therapy to reduce the susceptibility of a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

The term "vaccine" and "vaccine composition", as used herein, refers to a formulation which contains a conjugate or a composition according to the present invention in a suitable form for administration to a vertebrate and induce a protective immune response. The conjugate or a composition is sufficient to induce immunity to prevent or ameliorate an infection or to reduce at least one symptom of an infection or to enhance the efficacy of another dose of conjugate or composition of the invention.

The term "vaginal cream", as used herein, refers to a semi-solid preparation suitable for application to the vaginal tract. Various classes of excipients or vehicles known in the art can be used in its preparation. The excipients comprise materials of naturally occurring or synthetic origin that do not adversely affect the components of the formulation. Suitable carriers for use herein include but are not limited to purified water, white soft paraffin, mucoadhesive polymers, liquid paraffin, polysorbate 60, sorbitan stearate silicone, waxes, petroleum, jelly, polyethylene glycol, and a variety of other materials, depending on the specific type of formulation used.

The term "expression vector", as used herein, refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

The term "viral entry inhibitor", as used herein, refers to any compound capable of interfering with the entry of viruses into cells.

The term "viral immunogens", as used herein, refers to the whole HIV inactivated virions obtained by the inactivation process of the invention.

2. Therapeutic Methods of the Invention Using Inhibitors of the Interaction Between Sialoadhesin and Sialyllactose The present invention discloses that gangliosides in the HIV-1 membrane are necessary for its uptake by mature dendritic cells (mDCs). In particular, the sialyllactose molecule present in specific viral gangliosides was identified as the determinant moiety for mDC uptake. In addition, the present invention discloses also that sialoadhesin (CD169, siglec-1) a cell adhesion protein located on the surface of several immune system cells, such as DCs, attaches to the sialyllactose molecule in the HIV-1 surface to enable viral intake by mDCs. Therefore, the interaction of sialodhesin and sialyllactose is what allows HIV-1 to gain entry into mDCs. In consequence, the inhibition of this interaction can be used for preventing the spread of HIV by blocking trans-infection of CD4+ T cells by mDCs. Enveloped viruses acquire their envelope from the budding from the membrane of the infected cell and therefore, the composition of the viral envelope will reflect the composition of the cells from which the virus has budded. Since biological membranes contain gangliosides, viral envelopes are predicted to contain gangliosides. Moreover, the ganglioside GM3 was previously detected in the membrane of HIV-1 and several other viruses (e.g. SFV, VSV, MuLV). See Chan R, et al., J. Virol. 2008; 82:11228-11238 and Kalvodova L, et al., J. Virol. 2009; 83: 7996-8003. Therefore, the mechanism for HIV uptake by mDCs identified in the present invention may be relevant for uptake of any enveloped viruses and thus, the use of inhibitors of the interaction between sialoadhesin and sialyllactose may be useful for preventing infection by any enveloped virus. Thus, in a first aspect, the invention relates to an inhibitor of the interaction between sialoadhesin and sialyllactose for use in the treatment or prevention of a disease associated with an infection caused by an enveloped virus.

In another embodiment, the invention relates to the use of an inhibitor of the interaction between sialoadhesin and sialyllactose for the preparation of a medicament for the treatment of a disease associated with an infection caused by an enveloped virus.

In another aspect, the invention relates to a method for treatment or prevention of a disease associated with an infection caused by an enveloped virus in a subject in need thereof which comprises the administration to said subject of a an inhibitor of the interaction between sialoadhesin and sialyllactose.

Inhibitors suitable for use in the present invention can be identified using any known assay for detecting interactions between sialoadhesin and sialyllactose or any other compound comprising sialyllactose. For instance, inhibitors for use according to the present invention can be identified using the assay described in example 5 of the present invention based on the determination of the capability of the inhibitor to reduce the capture by mature dendritic cells of large unilamelar vesicles comprising lipids containing sialyllactose within their structure. Lipids containing sialyllactose within their structure and which can be incorporated into the large unilamelar vesicles include mono-, di- and trisialylgangliosides containing a sialyllactose moiety such as, without limitation, GM1, GM2, GM3, GD1b and GT1b.

Suitable inhibitors for use according to the present invention include, without limitation, sialyllactose, a molecule comprising a sialyllactose moiety, an anti-sialoadhesin antibody, anti-sialyllactose antibody and a vesicle comprising a molecule comprising a sialyllactose moiety.

In a preferred embodiment, the inhibitor for use according to the present invention is sialyllactose.

In a preferred embodiment, the molecule comprising a sialyllactose moiety is a ganglioside having less than four sialic acids.

Gangliosides suitable for use as inhibitors of the interaction between sialoadhesin and sialyllactoseare depicted in Table 1.

TABLE 1

Gangliosides containing sialyllactose residues which inhibit the interaction between sialadhesin and sialyllactose.

| | |
|---|---|
| GM3 | aNeu5Ac(2-3)bDGalp(1-4)bDGlcp(1-1)Cer |
| GM2 | bDGalpNAc(1-4)[aNeu5Ac(2-3)]bDGalp(1-4)bDGlcp(1-1)Cer |
| GM2a | aNeu5Ac(2-8)aNeu5Ac(2-3)bDGalp(1-4)bDGlcp(1-1)Cer |
| GM1/GM1a | bDGalp(1-3)bDGalNAc[aNeu5Ac(2-3)]bDGalp(1-4)bDGlcp(1-1)Cer |
| GM1b | aNeu5Ac(2-3)bDGalp(1-3)bDGalNAc(1-4)bDGalp(1-4)bDGlcp(1-1)Cer |
| GD3 | aNeu5Ac(2-8)aNeu5Ac(2-3)bDGalp(1-4)bDGlcp(1-1)Cer |
| GD2 | bDGalpNAc(1-4)[aNeu5Ac(2-8)aNeu5Ac(2-3)]bDGalp(1-4)bDGlcp(1-1)Cer |
| GD1a | aNeu5Ac(2-3)bDGalp(1-3)bDGalNAc(1-4)[aNeu5Ac(2-3)]bDGalp(1-4)bDGlcp(1-1)Cer |
| GD1alpha | aNeu5Ac(2-3)bDGalp(1-3)bDGalNAc(1-4)[aNeu5Ac(2-6)]bDGalp(1-4)bDGlcp(1-1)Cer |
| GD1b | bDGalp(1-3)bDGalNAc(1-4)[aNeu5Ac(2-8)aNeu5Ac(2-3)]DGalp(1-4)bDGlcp(1-1)Cer |
| GT1a | aNeu5Ac(2-8)aNeu5Ac(2-3)bDGalp(1-3)bDGalNAc(1-4)[aNeu5Ac(2-3)]bDGalp(1-4)bDGlcp(1-1)Cer |
| GT1, GT1b | aNeu5Ac(2-3)bDGalp(1-3)bDGalNAc(1-4)[aNeu5Ac(2-8)aNeu5Ac(2-3)]bDGalp(1-4)bDGlcp(1-1)Cer |
| OAc-GT1b | aNeu5Ac(2-3)bDGalp(1-3)bDGalNAc(1-4)aXNeu5Ac9Ac(2-8)aNeu5Ac(2-3)]bDGalp(1-4)bDGlcp(1-1)Cer |
| GT1c | bDGalp(1-3)bDGalNAc(1-4)[aNeu5Ac(2-8)aNeu5Ac(2-8)aNeu5Ac(2-3)]bDGalp(1-4)bDGlcp(1-1)Cer |
| GT3 | aNeu5Ac(2-8)aNeu5Ac(2-8)aNeu5Ac(2-3)bDGal(1-4)bDGlc(1-1)Cer | aNeu5Ac = 5-acetyl-alpha-neuraminic acid;
aNeu5Ac9Ac = 5,9-diacetyl-alpha-neuraminic acid;
bDGalp = beta-D-galactopyranose;
bDGalpNAc = N-acetyl-beta-D-galactopyranose;
bDGlcp = beta-D-glucopyranose and
Cer = ceramide (general N-acylated sphingoid).

The invention also contemplates the use of ganglioside derivatives wherein one or more of the following functional groups are substituted or added to the backbone chain, in particular the ceramide backbone chain:

1) a halide atom, bonded to an alkyl, alkenyl, alkynyl or aryl radical,
2) an alcohol group (primary, secondary or tertiary),
3) an ether group,
4) a carbonyl function (e.g. aldehyde or ketone),
5) a carboxylic acid group,
6) a carboxylic anhydride group,
7) a carbamoyl group,
8) a haloformyl group, 9) a cyano group, an ester group, including a lactone group, 10) a benzyl, phenyl, tosyl. tolyl or sulfonyl group, 11) an amino group (primary, secondary or tertiary), 12) an isocyanate, a cyanate, a thioisocyanate, a thiocyanate, a carbamate, or 13) an azide or a diazo group.

In another embodiment, the "inhibitor of the interaction between sialoadhesin and sialyllactose" is an antibody specific for sialoadhesin or sialyllactose.

The invention also comprises the use of fragments of the different types of antibodies mentioned above which substantially preserve the ability to bind sialoadhesin and preventing its interaction with molecules containing sialyllactose. The term "antibody fragment" includes antibody fragments such as Fab, F(ab')$_2$, Fab', single chain Fv fragments (scFv), diabodies and nanobodies.

In another embodiment, the inhibitor of the interaction between sialoadhesin and sialyllactose is the anti-sialiadhesin specific antibody 7D2 (available from Abcam, Catalog Number: ab18619) or a fragment thereof. In another embodiment, the inhibitor of the interaction between sialoadhesin and sialyllactose is the anti-sialiadhesin specific antibody 7-239 (available from eBioscience, Catalog Number: 12-1699-41) or a fragment thereof.

In another embodiment, the inhibitor of the interaction between sialoadhesin and sialyllactose is a sialyllactose-binding molecule. This type of molecules are capable of binding the sialyllactose found in the surface of the enveloped viruses and prevent their interaction with sialoadhesin. Suitable sialylactose-binding molecules include, without limitation, sialyllactose-binding lectins and anti-sialyllactose antibodies. Suitable sialyllactose-binding lectins include, without limitation, sialoadhesin or the extracellular domain thereof, the *Sambucus nigra* (elderberry) bark lectin (specific for sialyllactose having a α2,6-linkage), the *Maackia amurensis* lectin (specific for sialyllactose having a α2,3-sialyl bond) and the *Vibrio cholerae* neuraminidase or a lectin-like domain thereof.

In another embodiment, the inhibitor of the interaction between sialoadhesin and sialyllactose is a vesicle which comprises a molecule which comprises a sialyllactose moiety.

In one embodiment, the vesicle is a liposomes, a lipoplex or a lipid nanoparticle. In one embodiment, the vesicle is a liposome. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations. In a preferred embodiment, the vesicle is a large unilamellar vesicle.

MLVs can be prepared by solvent injection, lipid hydration, reverse evaporation, freeze drying or by repeated freezing and thawing. SUVs or LUVs may be prepared e.g. by sonication, by extrusion through polycarbonate filters having a defined pore size, by using a French pressure cell, i.e., by passing MLV through small orifice under high pressure, or by solvent injection methods, with solvents such as ethers or alcohols. Other types of vesicles which may be formed include unilamellar vesicle (ULV), large unilamellar vesicles (LUV); stable plurilamellar vesicles (SPLV), oligo-lamellar vesicles (OLV) whether prepared by detergent removal using dialysis, column chromatography, bio-beads SM-2, by reverse phase evaporation (REV); intermediate sized unilamellar vesicles formed by high pressure extrusions or giant multivesicular vesicles (MW or GMW, U.S. Pat. No. 6,162,462) liposomes, at least 1 microns in diameter, prepared by vortexing a lipid film with an aqueous solution of a suitable salt (e.g. ammonium sulfate), homogenizing the resulting suspension to form a suspension of small unilamellar vesicles (SUV), and repeatedly freeze-thawing said suspension of SUV in liquid nitrogen followed by water to form the MW. All these and other methods of liposome preparation, known in the art.

Suitable vesicles according to the present invention comprise one or more membranes consisting of at least one phospholipid selected from the group consisting of dioleoyl-phosphatidylethanolamine (hereafter referred to as "DOPE"), palmitoyloleoylglycerophosphocholine (hereafter referred to as "POPC"), cholesterol (hereafter referred to as "CHOL"), O,O'-ditetradecanoyl-N-α-trimethylammonio-acetyl)diethanolaminechloride (hereafter referred to as "DC-6-14"), hydrogenated purified yolk phosphatidylcholine, hydrogenated purified soybean phosphatidylcholine, dipalmitoyl phosphatidylcholine, distearoyl phosphatidyl-choline, and 1-palmitoyl-2-oleoyl phosphatidylcholine. Preferably, the liposome is a LUV comprising POPC, DPPC, CHOL and sphingomyelin (SM). The content ratio (molar ratio) of POPC, DPPC, CHOL, SM and the sialyllactose-containing moiety in the LUV according to the invention is POPC:DPPC:CHOL:SM:sialyllactose-containing moiety=25:16:10:45:4. Suitable molecule which comprises a sialyllactose moiety that can be incorporated in the vesicles for use in the present invention include any of the molecules mentioned above, including any of the gangliosides mentioned in Table 1 as well as derivatives thereof. In some embodiments, the molecule containing sialyllactose within its structure and which can be incorporated into the LUV include mono-, di- and trisialylgangliosides containing a sialyllactose moiety such as, without limitation, GM1, GM2, GM3, GD1b and GT1b.

In an embodiment, the disease associated with an infection caused by an enveloped virus is a disease caused by a type I filoviridae virus. Type I filoviridae virus which has a single-stranded, unsegmented (−) sense RNA genome and which causes severe hemorrhagic fever in humans and non-human primates. In some aspects, the filoviridae virus is an Ebola virus, such as a Cote d'lvoire (CI), Sudan (S), Zaire (Z) or Reston (R) species of Ebola virus. In further aspects, the filoviridae virus is a Marburg virus.

In another embodiment, the disease associated with an infection caused by an enveloped virus is a disease caused by an orthomyxoviridae virus, such as an influenza virus, Thogotovirus, Dhori virus, or infectious salmon anemia virus. For example, in some aspects, methods provided herein are used to treat or prevent infection of a human subject with an influenza type A virus, an influenza type B virus, or an influenza type C virus. In some aspects, the influenza type A virus is of subtype H1N1, H2N2, H3N2 or H5N1.

In another embodiment, the disease associated with an infection caused by an enveloped virus is a disease caused by a paramyxoviridae virus, such as human parainfluenza virus, human respiratory syncytial virus (RSV), Sendai virus, Newcastle disease virus, mumps virus, rubella (measles) virus, Hendra virus, Nipah virus, avian pneumo virus, or canine distemper virus.

In another embodiment, the disease associated with an infection caused by an enveloped virus is a disease caused by a rhabdoviridae virus, such as rabies virus, vesicular stomatitis virus (VSV), Mokola virus, Duvenhage virus, European bat virus, salmon infectious hematopoietic necrosis virus, viral hemorrhagic septicaemia virus, spring viremia of carp virus, or snakehead rhabdovirus.

In another embodiment, the disease associated with an infection caused by an enveloped virus is a disease caused by a bornaviridae virus, such as Borna disease virus.

In another embodiment, the disease associated with an infection caused by an enveloped virus is a disease caused by a bunyaviridae virus, such as Bunyamwera virus, Hantaan virus, Crimean Congo virus, California encephalitis virus, Rift Valley fever virus, or sandfly fever virus.

In another embodiment, the disease associated with an infection caused by an enveloped virus is a disease caused by is an arenaviridae virus, such as Old World Arenaviruses, Lassa fever virus, Ippy virus, Lymphocytic choriomeningitis virus (LCMV), Mobala virus, Mopeia virus, or a New World Arenavirus, such as Junin virus (Argentine hemorrhagic fever), Sabia (Brazilian hemorrhagic fever), Amapari virus, Flexal virus, Guanarito virus (Venezuela hemorrhagic fever), Machupo virus (Bolivian hemorrhagic fever), Latino virus, Boliveros virus, Parana virus, Pichinde virus, Pirital virus, Tacaribe virus, Tamiami virus, or Whitewater Arroyo virus. In some aspects, the Arenaviridae virus is Lymphocytic choriomeningitis virus, Lassa virus, Junin Virus, Machupo Virus, Sabia virus, or Guanarito virus.

In another embodiment, the disease associated with an infection caused by an enveloped virus is a disease caused by an arbovirus. Arboviruses comprise a large group of more than 400 enveloped RNA viruses that are transmitted primarily by arthropod vectors (e.g. mosquitoes, sand-flies, fleas, ticks, lice). In some aspects, the arbovirus is a togaviridae virus, such as an Alphavirus (e.g. Venezuela equine encephalitis virus or Sindbis virus) or a Rubivirus (e.g. Rubella virus). For example, in some aspects, a compound provided herein is administered to a pregnant subject to treat or prevent congenital rubella syndrome (CRS) and symptoms related thereto, such as low birth weight, deafness, and abortion.

In another embodiment, the disease associated with an infection caused by an enveloped virus is a disease caused by is a flaviviridae virus, such as a Flavivirus, a Pestivirus, a Hepadvirus, yellow fever virus, dengue fever virus, or Japanese encaphilitis (JE) virus.

In another embodiment, the disease associated with an infection caused by an enveloped virus is a disease caused by a hepacivirus, such as a hepatitis C virus or a hepatitis C-like virus.

In another embodiment, the disease associated with an infection caused by an enveloped virus is a disease caused by a henipavirus, such as Hendra virus or Nipah virus.

In another embodiment, the disease associated with an infection caused by an enveloped virus is a disease caused by a bunyaviridae (−)-sense RNA virus, such as an Orthobunyavirus, a Hantavirus, a Phlebovirus, or a Nairovirus.

In another embodiment, the disease associated with an infection caused by an enveloped virus is a disease caused by an arenavirus virus, such as Lymphocytic choriomeningitis virus (LCMV), Lassa virus, Junin virus, Machupo virus, or Guanarito virus.

In some aspects, the disease associated with an infection caused by an enveloped virus is a disease caused by a Japanese encephalitis virus, such as Alfuy virus, Japanese encephalitis virus, Kokobera virus, Koutango virus, Kunjin virus, Murray Valley encephalitis virus, St. Louis encephalitis virus, Stratford virus, Usutu virus, or West Nile virus.

In a preferred embodiment, the disease associated with an infection caused by an enveloped virus is a disease caused by a virus belonging to the retroviridae family. In a more preferred embodiment, the enveloped virus is a virus belonging to the orthoretrovirinae subfamily. In a still more preferred embodiment, the enveloped virus belongs to the lentivirus genus. In a more preferred embodiment, the enveloped virus is a primate lentivirus and, in particular, human immunodeficiency virus (HIV) or Simian immunodeficiency virus (SIV).

In some aspects, the disease associated with an infection caused by an enveloped virus is a disease caused by a Japanese encephalitis virus, such as Alfuy virus, Japanese encephalitis virus, Kokobera virus, Koutango virus, Kunjin virus, Murray Valley encephalitis virus, St. Louis encephalitis virus, Stratford virus, Usutu virus, or West Nile virus.

In a preferred embodiment, the disease associated with an infection caused by an enveloped virus is a disease caused by a virus belonging to the retroviridae family. In a more preferred embodiment, the enveloped virus is a virus belonging to the orthoretrovirinae subfamily. In a still more preferred embodiment, the enveloped virus belongs to the lentivirus genus. In a more preferred embodiment, the enveloped virus is a primate lentivirus and, in particular, human immunodeficiency virus (HIV) or Simian immunodeficiency virus (SIV).

Examples of retroviruses include but are not limited to the following virus genera: alpharetrovirus (e.g. avian leukosis virus (ALV) and rous sarcoma virus (RSV)), betaretrovirus (e.g. mouse mammary tumour virus (MMTV), SRV, HERV-K and JRSV), gammaretrovirus (e.g. murine leukemia virus (MLV), feline leukemia virus (FeLV), GALV, PERV, and HERV-W), deltaretrovirus (e.g. bovine leukemia virus (BLV), and cancer-causing human T-lymphotropic virus (HTLV-1 and HTLV-ll)), epsilonretroviriis (e.g. Walleye dermal sarcoma virus (WDSV) and SnRV), lentivirus (e.g. human immunodeficiency virus 1 (HIV-1), human immunodeficiency virus 2 (HIV-2), simian immunodeficiency virus (SIVmac and SIV), feline immunodeficiency virus (FlV), EIAV and MVV) and spumavirus (e.g. simian foamy virus (SFVcpz and SFVagm), FFV and BFV).

In a preferred embodiment, the enveloped virus is a virus wherein at least some of the lipids within the envelope of said enveloped virus comprise sialyllactose. In a more preferred embodiment, the enveloped virus comprises gangliosides in the viral envelope wherein the gangliosides contain at least one sialyllactose moiety. In a still more preferred embodiment, the gangliosides contain less than four sialyllactose molecules. In yet another embodiment, the virus contains in its envelope one or more of the gangliosides shown in Table 1.

In a preferred embodiment, the "disease associated with an infection caused by an enveloped virus" is a disease associated with an HIV virus.

The present invention further relates to preventing or reducing symptoms associated with HIV infection. These include symptoms associated with the minor symptomatic phase of HIV infection, including, for example, shingles, skin rash and nail infections, mouth sores, recurrent nose and throat infection and weight loss. In addition, further symptoms associated with the major symptomatic phase of HIV infection, include, for instance, oral and vaginal thrush (*Candida*), persistent diarrhea, weight loss, persistent cough and reactivated tuberculosis or recurrent herpes infections, such as cold sores (herpes simplex). Other symptoms of full-blown AIDS which can be treated in accordance with the present invention include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii* pneumonia (PCP), herpes zoster (or shingles), nervous system problems, such as pains, numbness or "pins and needles" in the hands and feet, neurological abnormalities, Kaposi's sarcoma, lymphoma, tuberculosis or other similar opportunistic infections.

Beneficial effects of the inhibitors of the invention include, for example, preventing or delaying initial infection of an individual exposed to HIV, reducing viral burden in an individual infected with HIV, prolonging the asymptomatic phase of HIV infection, maintaining low viral loads in HIV infected patients whose virus levels have been lowered via anti-retroviral therapy (ART), increasing levels of CD4 T cells or lessening the decrease in CD4 T cells, both HIV-1 specific and non-specific, in drug naïve patients and in patients treated with ART, increasing overall health or quality of life in an individual with AIDS and prolonging life expectancy of an individual with AIDS. A clinician can compare the effect of immunization with the patient's condition prior to treatment, or with the expected condition of an untreated patient, or in a clinical trial of individuals treated and untreated with the vaccine to determine whether the treatment is effective in inhibiting AIDS.

The compounds of the present invention may be useful in the methods of present invention in combination with one or more additional anti-HIV agent or agent. These additional compounds may comprise compounds of the present invention or compounds, e.g., commercially available compounds, known to treat, prevent, or reduce the symptoms of HIV infections.

In non-limiting examples, the compounds of the invention may be used in combination with one or more of the following anti-HIV drugs:

1) Combination drugs: efavirenz, emtricitabine or tenofovir disoproxil fumarate (Atripla®/BMS, Gilead); lamivudine or zidovudine (Combivir®/GSK); abacavir or lamivudine (Epzicom®/GSK); abacavir, lamivudine or zidovudine (Trizivir®/GSK); emtricitabine, tenofovir disoproxil fumarate (Truvada®/Gilead).

2) Entry and fusion inhibitors: maraviroc (Celsentri®, Selzentry®/Pfizer); pentafuside or enfuvirtide (Fuzeon®/Roche, Trimeris). In some embodiments, the viral entry inhibitor is a fusion inhibitor, a CD4 receptor binding inhibitor, is a CD4 mimic or a gp120 mimic. In some further embodiments, the viral entry inhibitor is a gp41 antagonist, a CD4 monoclonal antibody or a CCR5 antagonist, including CCR5 antagonist subclasses such as, for example, zinc finger inhibitors. In yet another embodiment, the viral entry inhibitor is a CXCR4 co-receptor antagonist.

3) Integrase inhibitors: raltegravir or MK-0518 (Isentress®/Merck).

4) Reverse transcriptase inhibitors: Suitable reverse transcriptase inhibitors for use in the compositions according to the present invention is one or more compounds selected from the group consisting of emtricitabine, capravirine, tenofovir, lamivudine, zalcitabine, delavirdine, nevirapine, didanosine, stavudine, abacavir, alovudine, zidovudine, racemic emtricitabine, apricitabine, emivirine, elvucitabine, TMC-278, DPC-083, amdoxovir, (−)-beta-D-2,6-diamino-purine dioxolane, MIV-210 (FLG), DFC (dexelvucitabine), dioxolane thymidine, Calanolide A, etravirine (TMC-125), L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I$^2$-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, and L697639, where the compounds are present in amounts effective for treatment of HIV when used in a combination therapy.

5) Protease inhibitors: Suitable protease inhibitors that can be combined with the miRNAs or polynucleotides encoding miRNAs according to the invention is selected from the group consisting of ritonavir, lopinavir, saquinavir, amprenavir, fosamprenavir, nelfinavir, tipranavir, indinavir, atazanavir, TMC-126, darunavir, mozenavir (DMP-450), JE-2147 (AG1776), L-756423, KNI-272, DPC-681, DPC-684, telinavir (SC-52151), BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, and brecanavir (GW640385). Preferred protease inhibitors for use in combination with a compound of the present invention include saquinavir, ritonavir, indinavir, nelfinavir, amprenavir, lopinavir, atazanavir, darunavir, brecanavir, fosamprenavir, and tipranavir. Particularly useful such combinations include, for example, AZT+3TC; TDF+3TC; TDF+FTC; ABC+3TC; and Abacavir+3TC.

Additionally, the compositions according to the present invention may further comprise an antiretroviral agent selected from the group consisting of vaccines, gene therapy treatments, cytokines, TAT inhibitors, and immunomodulators in amounts effective for treatment of HIV when used in a combination therapy.

Additionally, the compositions according to the present invention may further comprise an antiinfective agent selected from the group consisting of antifungals, antibacterials, anti-neoplasties, anti-protozoals, DNA polymerase inhibitors, DNA synthesis inhibitors, anti-HIV antibodies, HIV antisense drugs, IL-2 agonists, α-glucosidase inhibitors, purine nucleoside phosphorylase inhibitors, apoptosis agonists, apoptosis inhibitors, and cholinesterase inhibitors, where the compounds are present in amounts effective for treatment of HIV when used in a combination therapy.

Additionally, the compositions according to the present invention may further comprise an immunomodulator, which is selected from the group consisting of pentamidine isethionate, autologous CD8+ infusion, γ-interferon immunoglobulins, thymic peptides, IGF-I, anti-Leu3A, auto vaccination, biostimulation, extracorporeal photophoresis, cyclosporin, rapamycin, FK-565, FK-506, GCSF, GM-CSF, hyperthermia, isopinosine, rVIG, HIVIG, passive immunotherapy and polio vaccine hyperimmunization, where the compounds are present in amounts effective for treatment of HIV when used in a combination therapy.

The combinations of the inhibitors according to the invention and the anti-HIV agents may result in a synergistic effect in terms of its anti-HIV activity. A synergistic effect may be calculated, for example, using suitable methods such as, for example, the Sigmoid-Emax, Loewe, and median-effect equations. See Holford K, Scheiner L, Clin. Pharmacokinet 1981; 6:429-453, Loewe S, Muischnek H, Arch. Exp. Pathol Pharmacol. 1926; 114:313-326 and Chou T, Talalay C, Adv. Enzyme Regul. 1984; 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The inhibitors according to the invention may further comprise a pharmaceutically acceptable carrier. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation. Adjuvants could for example be selected from the group consisting of: AlK(SO4)2, AlNa(SO4)2, AlNH4 (SO4), silica, alum, $Al(OH)_3$, $Ca_3(PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1 '2'-dipalmitoyl-sn-glycero-3-hydroxphosphoryloxy)-ethylamine (CGP 19835A, also referred to as MTP-PE), RIBI (MPL+TDM+CWS) in a 2 percent squalene/Tween-80®emulsion, lipopolysaccharides and its various derivatives, including lipid A, Freund's Complete Adjuvant (FCA), Freund's Incomplete Adjuvants, Merck Adjuvant 65, polynucleotides (e.g. poly IC and poly AU acids), wax D from *Mycobacterium*, tuberculosis, substances found in *Corynebacterium parvum, Bordetella pertussis*, and members of the genus *Brucella*, Titermax, ISCOMS, Quil A, ALUN, Lipid A derivatives, choleratoxin derivatives, HSP derivatives, LPS derivatives, synthetic peptide matrixes or GMDP, interleukin 1, interleukin 2, Montanide ISA-51 and QS-21, CpG oligonucleotide, poly I:C and GM-CSF. See Hunter R, U.S. Pat. No. 5,554,372, and Jager E, Knuth A, WO1997028816.

The inhibitors according to the invention can be administered by any means known to one skilled in the art, such as by intramuscular, subcutaneous or intravenous injection, and oral, nasal, or anal administration. See Banga A, Parenteral controlled delivery of therapeutic peptides and proteins, "Therapeutic Peptides and Proteins" (Technomic Publishing Co., Inc., Lancaster, Pa., US, 1995). To extend the time during which the inhibitor is available to exert its effect, the inhibitor can be provided as an implant, an oily injection, or as a particulate system. The particulate system can be a microparticle, a microcapsule, a microsphere, a nanocapsule, or similar particle. See Banga, 1995, supra. A particulate carrier based on a synthetic polymer has been shown to act as an adjuvant to enhance the immune response, in addition to providing a controlled release. Aluminum salts can also be used as adjuvants to produce an immune response.

The inhibitors according to the invention may be formulated as microbicide compositions. Microbicide compositions can be formulated in unit dosage form, suitable for individual administration of precise dosages. In pulse doses, a bolus administration of an immunogenic composition that includes a disclosed immunogen is provided, followed by a time-period wherein no disclosed immunogen is administered to the subject, followed by a second bolus administration. A therapeutically effective amount of an inhibitor can be administered in a single dose, or in multiple doses, for example daily, during a course of treatment. In specific, non-limiting examples, pulse doses of an immunogenic composition that include a disclosed immunogen are administered during the course of a day, during the course of a week, or during the course of a month. Microbicide compositions can be administered whenever the effect (such as decreased signs, symptom, or laboratory results of HIV-1 infection) is desired. Generally, the dose is sufficient to treat or ameliorate symptoms or signs of disease without producing unacceptable toxicity to the subject. Systemic or local administration can be utilized.

Amounts effective for therapeutic use can depend on the severity of the disease and the age, weight, general state of the patient, and other clinical factors. Thus, the final determination of the appropriate treatment regimen will be made by the attending clinician. Typically, dosages used in vitro can provide useful guidance in the amounts useful for in situ administration of the pharmaceutical composition, and animal models may be used to determine effective dosages for treatment of particular disorders. See Gilman R, et al., Eds., "Goodman and Gilman's: The Pharmacological Basis of Therapeutics", 8th Ed. (Pergamon Press, New York, N.Y., US, 1990), and Gennaro A, Ed., "Remington's Pharmaceutical Sciences", 18th Ed. (Mack Publishing Co., Easton, Pa., US, 1990). Typically, the dose range for an inhibitor is from about 0.1 µg/kg body weight to about 100 mg/kg body weight. Other suitable ranges include doses of from about 1 µg/kg to 10 mg/kg body weight. In one example, the dose is about 1.0 µg to about 50 mg, for example, 1 µg to 1 mg, such as 1 mg peptide per subject. The dosing schedule can vary from daily to as seldom as once a year, depending on clinical factors, such as the subject's sensitivity to the peptide and tempo of their disease. Therefore, a subject can receive a first dose of a disclosed therapeutic molecule, and then receive a second dose (or even more doses) at some later time(s), such as at least one day later, such as at least one week later.

The pharmaceutical compositions disclosed herein can be prepared and administered in dose units. Solid dose units include tablets, capsules, transdermal delivery systems, and suppositories. The administration of a therapeutic amount can be carried out both by single administration in the form of an individual dose unit or else several smaller dose units and also by multiple administrations of subdivided doses at specific intervals. Suitable single or divided doses include, but are not limited to about 0.01, 0.1, 0.5, 1, 3, 5, 10, 15, 30, or 50 µg protein/kg/day.

In therapeutic applications, a therapeutically effective amount of the inhibitor is administered to a subject prior to or following exposure to or infection by HIV. When administered prior to exposure, the therapeutic application can be referred to as a prophylactic administration (such as in the form of a vaccine). Single or multiple administrations of the compositions are administered depending on the dosage and frequency as required and tolerated by the subject. In one embodiment, the dosage is administered once as a bolus, but in another embodiment can be applied periodically until a therapeutic result, such as a protective immune response, is achieved. Generally, the dose is sufficient to treat or ameliorate symptoms or signs of disease without producing unacceptable toxicity to the subject. Systemic or local administration can be utilized.

It may be advantageous to administer the microbicide compositions disclosed herein with other agents such as proteins, peptides, antibodies, and other anti-HIV agents.

Examples of such anti-HIV therapeutic agents include nucleoside reverse transcriptase inhibitors, such as abacavir, AZT, didanosine, emtricitabine, lamivudine, stavudine, tenofovir, zalcitabine, or zidovudine; non-nucleoside reverse transcriptase inhibitors, such as delavirdine, efavirenz, or nevirapine; protease inhibitors, such as amprenavir, atazanavir, indinavir, lopinavir, nelfinavir osamprenavir, ritonavir, saquinavir, or tipranavir; or fusion protein inhibitors, such as enfuvirtide. In certain embodiments, the inhibitors are administered concurrently with other anti-HIV therapeutic agents. In certain embodiments, the immunogenic compositions are administered sequentially with other anti-HIV therapeutic agents, such as before or after the other agent. One of ordinary skill in the art would know that sequential administration can mean immediately following or after an appropriate period of time, such as hours days, weeks, months, or even years later.

The pharmaceutical composition of the invention may be applied to the vagina in a number of forms including aerosols, foams, sprays, pastes, gels, jellies, creams, suppositories, tablets, pessaries, tampons, or devices such as vaginal rings. They can be in the form of immediate release or controlled release. Foams, creams and gels are preferred forms. Compositions suitable for vaginal application and their methods of preparation are known in the art. See Vickery B, et al., U.S. Pat. No. 4,368,186, Gazzani G, U.S. Pat. No. 4,371,518, Tice T, et al., U.S. Pat. No. 4,389,330, Joyce C, et al., U.S. Pat. No. 4,415,585, and Riley T, et al., U.S. Pat. No. 4,551,148.

In a particularly preferred embodiment, the pharmaceutical composition is topically applied to the vagina. Typically, the topical application is carried out prior to the beginning of vaginal intercourse, suitably 0 to 60 minutes, preferably 0 to 5 minutes, prior to the beginning of vaginal intercourse. The application may be carried out into and around the vagina and vaginal area (e.g. the individual anatomical parts, such as, labia majora, labia minora, clitoris) of a female.

Pharmaceutical creams, as known in the art, are viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

For example, suitable vehicle bases include, but are not limited to, hydrocarbon bases or oleaginous bases, absorption bases, water-removable bases and water-soluble bases. In some embodiments, the vehicle base is non-irritating, non-staining, stable, non-pH dependent and/or compatible with the inhibitors according to the invention.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active ingredient with the softened or melted carrier(s) followed by chilling and shaping in moulds.

In another embodiment, the present invention involves topical administration of the composition to the anus. The composition administered to the anus is suitably a foam, cream, or jelly such as those described above regarding vaginal application. In the case of anal application, it may be preferred to use an applicator which distributes the composition substantially evenly throughout the anus. For example, a suitable applicator is a tube 2.5 to 25 cm, preferably 5 to 10 cm, in length having holes distributed regularly along its length.

In another embodiment, the present method may be carried out by applying the pharmaceutical composition orally. Oral application is suitably carried out by applying a composition which is in the form of a mouthwash or gargle. Oral application is especially preferred to prevent infection during dental procedures. Suitably, the composition is applied just prior to the beginning of the dental procedure and periodically throughout the procedure. Formulations suitable for topical administration in the mouth include lozenges comprising the active ingredient in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

It is noted that when the composition is in the form of a suppository (including vaginal suppositories), the suppository will usually be 1 to 5 grams, preferably about 3 grams, and the entire suppository will be applied. A vaginal tablet will suitably be 1 to 5 grams, preferably about 2 grams, and the entire tablet will be applied. When the composition is vaginal cream, suitably 0.1 to 2 grams, preferably about 0.5 grams of the cream will be applied. When the composition is a water-soluble vaginal cream, suitably 0.1 to 2 grams, preferably about 0.6 grams, are applied. When the composition is a vaginal spray-foam, suitably 0.1 to 2 grams, preferably about 0.5 grams, of the spray-foam are applied. When the composition is an anal cream, suitably 0.1 to 2 grams, preferably about 0.5 grams of the cream is applied. When the composition is an anal spray-foam, suitably 0.1 to 2 grams, preferably about 0.5 grams of the spray-foam are applied. When the composition is a mouthwash or gargle, suitably 1 to 10 ml, preferably about 5 ml are applied.

The present compositions may also be in the form of a time-release composition. In this embodiment, the inhibitor is incorporated in a composition which will release the active ingredient at a rate which will result in an effective vaginal or anal concentration of said inhibitor. See Lew D, Ed., "Controlled Release of Pesticides and Pharmaceuticals" (Plenum Press, New York, N.Y., US 1981), Pfister J, et al., J. Contr. Rel. 1986; 3:229-233, Lance W, U.S. Pat. No. 5,248,700, Behan J, et al., U.S. Pat. No. 5,185,155, and Viegas T, et al., U.S. Pat. No. 5,143,731.

The present compositions may also be in the form which releases the inhibitor of the invention in response to some event such as vaginal or anal intercourse. For example, the composition may contain the inhibitor in vesicles or liposomes, which are disrupted by the mechanical action of intercourse. Compositions comprising liposomes are known in the art. See Deamer D, Uster P, Liposome preparation: methods and mechanisms, Ostro M, Ed., "Liposomes" (Marcel Dekker Inc., New York, N.Y., US, 1983, pp. 27-51), Breimer D, Speiser P, Eds., "Topics in Pharmaceutical Sciences" Elsevier Science Publishers B.V., New York, N.Y., US, 1985, pp. 345-358), Sessa J, et al., J. Biol. Chem. 1970; 245:3295-3300, and Janoff A, et al., U.S. Pat. No. 5,231,112

It should also be realized that the present compositions may be associated with an article, such as an intrauterine device (IUD), vaginal diaphragm, vaginal ring, vaginal sponge, pessary, or condom. In the case of an IUD or diaphragm, time-release or mechanical-release compositions may be preferred, while in the case of condoms, mechanical-release compositions are preferred.

In another embodiment, the present invention provides novel devices, which are useful for the prevention of HIV infection. In particular, the present devices are those which release the inhibitor when placed on an appropriate body part or in an appropriate body cavity. Thus, the present invention provides IUDs, vaginal diaphragms, vaginal sponges, pessaries, or condoms which contain or are associated with an inhibitor.

Thus, a device according to the present invention may be an IUD which contains one or more inhibitors. See Ramwell P, U.S. Pat. No. 3,888,975 and Berthet J, et al., U.S. Pat. No. 4,283,325. This device may be an intravaginal sponge which comprises the inhibiting compound and releases it in a time-controlled fashion. See Robinson T, U.S. Pat. No. 3,916,898 and Barrows T, U.S. Pat. No. 4,360,013. The device may also be a vaginal dispenser, which releases the inhibitor. See Wong P, U.S. Pat. No. 4,961,931.

The present device may also be a condom which is coated with an inhibitor. In a preferred embodiment, the condom is coated with a lubricant or penetration enhancing agent which comprises an inhibitor and a spermicide, which is optionally selected from benzalkonium chloride, benzethonium chloride, cetyl pyridinium chloride, methylbenzethonium chloride, tetra-decyltrimethyl ammonium bromide, benzalkonium bromide, monylphenyl ethers, lauryl ethers, and octoxynols. However, it is recommended that use of a condom should be associated with use of an appropriate lubricating agent (i.e. one that does not degrade the mechanical strength properties of the condom and that does not increase its porosity due to the latex being attacked). For example, EP-A-0 457 127 describes a lubricant based on silicone oil for treating the latex of condoms, EP-A-0 475 664 describes a lubricating composition and use thereof with condoms, and FR-A-2 666 587 describes a lubricant comprising polydimethylsiloxane. The composition and preparation of other lubricants and penetration enhancing agents are known in the art. See Copper E, U.S. Pat. No. 4,557,934, Cooper E, U.S. Pat. No. 4,954,487; James M, et al., U.S. Pat. No. 4,499,154, and Kelly P, U.S. Pat. No. 5,208,031.

3. Therapeutic Methods of the Invention Using Inhibitors of Sialoadhesin

The present invention discloses that sialoadhesin (CD169, siglec-1), a cell adhesion protein located on the surface of several immune system cells, such as DCs, attaches to the sialyllactose molecule in the HIV-1 surface to enable viral intake by mDCs. Therefore, by decreasing the expression of sialodhesin in the cell can be used for preventing entry HIV-1 in the cell and, consequently, preventing the spread of HIV by blocking trans-infection of CD4+ T cells by mDCs. This is shown for instance in Example 7 of the present invention, wherein it is shown that silencing sialoadhesin expression in DC using sialoadhesin-specific shRNA leads to a drastic decrease in the expression of sialoadhesin and to a loss of capture of VLPs containing sialyllactose-containing gangliosides by said cells. Accordingly, in another aspect, the invention relates to a sialoadhesin inhibitor for use in the treatment or prevention of a disease associated with an infection caused by an enveloped virus. In another aspect, the invention relates to the use of a sialoadhesin inhibitor for the preparation of a medicament for the treatment of a disease associated with an infection caused by an enveloped virus. In another aspect, the invention relates to a method for treatment or prevention of a disease associated with an infection caused by an enveloped virus in a subject in need thereof which comprises the administration to said subject of a sialoadhesin inhibitor.

In some embodiments, the sialoadhesin inhibitor is an interfering RNA specific for sialoadhesin or a vector comprising a polynucleotide encoding such an interfering RNA.

In some embodiments, the sialoadhesin inhibitor is a sialoadhsein-specific siRNA. The siRNA can be chemically synthesised or can be obtained through in vitro transcription. siRNAs typically consist of a double RNA strand with a length between 15 and 40 nucleotides and can contain a 3' and/or 5' overhanging region with 1 to 6 nucleotides. The length of the overhanging region is independent of the total length of the siRNA molecule. The siRNAs of the invention are substantially homologous with a pre-selected region of the sialoadhesin mRNA. The siRNAs suitable for causing said interference include siRNAs formed by RNA, as well as siRNAs containing different chemical modifications such as:

siRNAs in which the bonds between the nucleotides are different from those that occur in nature, such as phosphorothioate bonds, conjugates of the siRNA strand with a functional reagent, such as a fluorophore, Modifications of the ends of the siRNA strands, particularly the 3' end by means of the modification with different functional groups of the hydroxyl in position 2', Nucleotides with modified sugars such as O-alkylated moieties in position 2' such as 2'-O-methylribose p 2'-O-fluororibose, Nucleotides with modified bases like halogenated bases (for example 5-bromouracil and 5-iodouracil), alkylated bases (for example 7-methylguanosine).

The siRNAs of the invention can be obtained using a series of techniques well-known to a person skilled in the art. For example, the siRNA can be chemically synthesised starting from ribonucleosides protected with phosphoramidite groups in a conventional DNA/RNA synthesizer.

In another embodiment, the sialoadhesin inhibitor is shRNA (short hairpin RNA). The shRNAs typically comprise a short antisense sequence (with 19 to 25 nucleotides), followed by a loop of 5 to 9 nucleotides followed by the sense strand. shRNAs can be chemically synthesized from ribonucleosides protected with phosphoramidite groups in a conventional DNA/RNA synthesizer or they can be obtained from a polynucleotide by means of in vitro transcription. shRNAs are processed inside the cell by the RNase Dicer that eliminates the hairpin region giving rise to siRNAs as has been previously described. shRNAs can also contain distinct chemical modifications as has been previously described in the case of siRNAs.

In another embodiment, the sialoadhesin inhibitor is miRNA. The miRNAs suitable for their use in the present invention consist of 19 to about 24 nucleotides, preferably 21 or 22 nucleotides. The miRNAs can be designed such that they hybridize to an RNA transcript with a high degree of specificity. The miRNA is preferably designed such that it shows a 100% identity or which shows a substantial identity (i.e. allowing at least 1, at least 2, at least 3 or more mismatches) with the target mRNA given that only one non-complementary nucleotide can, depending on its position in the miRNA strand, reduce the inhibition levels. The miRNAs can be designed such that they target the non-translated 5' region, the encoding region or the 3' region of the target mRNA.

The efficient processing and functioning of the miRNA is typically only possible when said miRNA has certain structural requirements, such as those described by Zeng et al. (RNA, 2003, 9:112-123). The miRNAs of the invention are preferably based on the mirR-30 structure in which the stem region has been replaced with target sequences of preselected mRNAs. The presence of miR-30 in the loop region, although desirable, is not absolutely necessary since it can tolerate certain variations such that the loop region has more than 70%, preferably more than 79%, even more preferably more than 86%, and even more preferably, more than 93% identity with respect to the loop sequence that appears in miR-30. Determination of the percent identity can be determined using any of the methods mentioned above.

In another embodiment, the sialoadhesin inhibitor is a polynucleotides encoding sialoadhesin-specific siRNA, shRNA or miRNA. In the case of polynucleotides encoding a shRNA or a miRNA, they comprise a sequence comprising the sense and antisense strands of the shRNAs and miRNAs connected by a hairpin or by a stem-loop region. In the case of polynucleotides encoding a siRNAs, these comprise two transcriptional units, each formed by a promoter regulating the transcription of one of the strands formed in siRNA (sense and antisense). The polynucleotides encoding siRNAs can contain convergent or divergent transcriptional units. In the divergent transcription polynucleotides, the transcriptional units encoding each of the DNA strands forming the siRNA are located in tandem in the polynucleotide such that the transcription of each DNA strand depends on its own promoter, which can be the same or different (Wang, J. et al., 2003, Proc. Natl. Acad. Sci. USA, 100: 5103-5106 and Lee, N. S., et al., 2002, Nat. Biotechnol., 20:500-505). In the convergent transcription polynucleotides, the DNA regions giving rise to the siRNAs form the sense and antisense strands of a DNA region that is flanked by two inverted promoters. After the transcription of the sense and antisense RNA strands, they will form the hybrid corresponding to the functional siRNA.

In principle, any promoter can be used for the expression of the shRNAs, miRNAs and siRNAs provided that said promoters are compatible with the cells in which the siRNAs are to be expressed. In a preferred embodiment, the polynucleotide encoding sialoadhesin-specific siRNA, shRNA or miRNA comprises a promoter specific for dendritic cells, such as the CD11c promoter, the DC-STAMP promoter and the fascin promoter. Other promoter combinations suitable for the polynucleotides comprising inverted transcriptional units include 2 U6 promoters (Tran, N. et al., 2003, BMC Biotechnol., 3:21), a mouse U6 promoter and a human H1 promoter (Zheng, L., et al., 2004, Proc. Natl. Acad. Sci. USA, 101:135-140 and WO2005026322) and a human U6 promoter and a mouse H1 promoter (Kaykas, A. & Moon, R., 2004, BMC Cell Biol., 5:16). In a preferred embodiment, the sense and antisense siRNA strands are regulated by different promoters. In an even more preferred embodiment, both transcriptional units are oriented in a convergent manner.

In some embodiments, the sialoadhesin inhibitor is an antisense oligonucleotide specific for sialoadhesin.

Antisense constructs may be designed to bind to the promoter and other control regions, exons, introns or even exon-intron boundaries of the sialoadhesin gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., Science, 260:1510-1513, 1993, herein incorporated by reference).

In some embodiments, the sialoadhesin inhibitor is a targeted ribozymes specific for sialoadhesin. In a preferred embodiment of the invention, the ribozyme is a hammerhead ribozyme, a small RNA molecule derived from plant viroids (Symons, Ann. Rev. Biochem. 61: 641-671, 1992; Clouet-D'Orval and Uhlenbeck, RNA, 2:483-491, 1996; Haseloff and Gerlach, Nature 334:585-591, 1988; Jeffries and Symons, Nucleic Acids Res. 17: 1371-1377, 1989; Uhlenbeck, Nature 328:596-600, 1987; all herein incorporated by reference). In other embodiments, the ribozyme may be a group I intron, a hairpin ribozyme, VS RNA, a hepatitis Delta virus ribozyme or an Rnase P-RNA ribozyme (in association with an RNA guide sequence). Examples of hairpin motifs are described by Hampel et al., Nucleic Acids Res. 18:299, 1990 and Hampel and Tritz, Biochemistry 28:4929, 1989; an example of the hepatitis delta virus motif is described by Perrotta and Been, Biochemistry 31:16, 1992; an example of the RNAseP motif (associated with an external guide sequence) is described by Yuan et al., U.S. Pat. No. 5,624,824; a Neurospora VS RNA ribozyme motif is described in Saville and Collins, Cell 61: 685-696, 1990, Saville and Collins, Proc. Natl. Acad. Sci. USA 88: 8826-8830, 1991, Collins and Olive, Biochemistry 32: 2795-2799, 1993; the group I intron is described in Cech et al., U.S. Pat. No. 5,354,855. The above-mentioned motifs should not be considered limiting with respect to the present invention and those skilled in the art will recognize that ribozymes that may be utilized herein comprise a specific substrate binding site which is complementary to a target mRNA. Such ribozymes also comprise an enzymatic portion which imparts RNA cleaving activity to the molecule. The enzymatic portion resides within or surrounds the substrate binding site.

Diseases associated with an infection caused by an enveloped virus that can be treated and/or prevented according to the present invention using sialoadhesin inhibitors include any of the diseases mentioned above in the context of the methods using inhibitors of the interaction between sialoadhesin and sialyllactose.

In some embodiments, the disease associated with an infection caused by an enveloped virus is a disease caused by a type I filoviridae virus, by an orthomyxoviridae virus, by a paramyxoviridae virus, by a rhabdoviridae virus, by a bornaviridae virus, by a bunyaviridae virus, by is an arenaviridae virus, by an arbovirus, by flaviviridae virus, by a hepacivirus, by a henipavirus, by a virus belonging to the retroviridae. In a more preferred embodiment, the enveloped virus is a virus belonging to the orthoretrovirinae subfamily. In a still more preferred embodiment, the enveloped virus belongs to the lentivirus genus. In a more preferred embodiment, the enveloped virus is a primate lentivirus and, in particular, human immunodeficiency virus (HIV) or Simian immunodeficiency virus (SIV).

In some embodiments, the sialoadhesin inhibitor may be used in combination with one or more additional anti-HIV agent or agents. These additional compounds may comprise compounds of the present invention or compounds, e.g., commercially available compounds, known to treat, prevent, or reduce the symptoms of HIV infections. Suitable anti-HIV agent are those described in the context of the methods using inhibitors of the interaction between sialoadhesin and sialyllactose.

In some embodiments, the sialoadhesin inhibitor may be used in combination with an antiinfective agent. In some embodiments, the sialoadhesin inhibitor may be used in combination with an immunomodulator.

Suitable pharmaceutical carriers, administration routes, formulations and dosage regimes have been described in detail in the context of the methods using inhibitors of the interaction between sialoadhesin and sialyllactose and are equally applicable to the present methods.

4. Compositions of the Invention and Therapeutic Uses Thereof

The present invention refers to the uptake of HIV by dendritic cells. This uptake has been found to require the interaction of gangliosides found in the viral envelope and CD169 present in the surface of the dendritic cells. The internalized virus can be processed and presented on the surface of the dendritic cells, thus inducing adaptive immune responses or can be transferred to CD4+ T cells. Thus, by providing a composition comprising dendritic cells loaded with an antigen of interest and an inhibitor of the interaction of CD169 and gangliosides on the viral envelope, it would be possible to allow dendritic cells to contribute to the generation of the adaptive immune response while blocking their ability to internalize HIV and promoting trans-infection of the CD4+ T cells. Thus, in another aspect, the invention relates to a composition or kit-of-parts comprising an antigen-loaded antigen-presenting cell and an inhibitor of the interaction between sialoadhesin and sialyllactose.

Dendritic cells suitable for this invention can be of different types such as, without limitation, myeloid DCs (myDCs), plasmacytoid DCs (pDCs), Langerhans cells and insterstitial DCs. The most potent of the professional APCs are DCs of myeloid origin. Thus, in a preferred embodiment DCs are myeloid DCs.

To obtain starting cell populations which comprise dendritic cell precursors and/or dendritic cells, samples of cells, tissues, or organs comprising dendritic cell precursors or dendritic cells are isolated from one or more subjects using methods known in the art. Such starting cell populations may be obtained from one subject or may be pooled from more than one donor.

In one embodiment, a starting population which comprises dendritic cells or dendritic cell precursors is derived from splenic tissue. In one embodiment, a starting cell population which comprises dendritic cells or dendritic cell precursors is derived from thymic tissue. In one embodiment, a starting cell population which comprises dendritic cells or dendritic cell precursors is derived from bone marrow. In one embodiment, a starting cell population which comprises dendritic cells or dendritic cell precursors is derived from peripheral blood (e.g. from whole blood) or by using leukophoresis. In one embodiment, a starting cell population of cells comprises dendritic cell precursors. In one embodiment, a population of cells comprising dendritic cell precursors can be harvested from the peripheral blood using standard mononuclear cell leukopheresis, a technique that is well known in the art. Dendritic cell precursors can then be collected (e.g. using sequential buoyant density centrifugation steps). For example, the leukopheresis product can be layered over a buoyant density solution (specific gravity=1.077 g/mL) and centrifuged at 1,000 g for 20 minutes to deplete erythrocytes and granulocytes. The interface cells are collected, washed, layered over a second buoyant density solution (specific gravity=1.065 g/mL), and centrifuged at 805 g for 30 minutes to deplete platelets and low-density monocytes and lymphocytes. The resulting cell pellet is enriched for dendritic cell precursors.

In another embodiment, a starting population of cells comprising dendritic cells can be obtained using methods known in the art. Such a population may comprise myeloid dendritic cells, plasmacytoid dendritic cells, or dendritic cells generated in culture from monocytes (e.g. MO-DCs, MDDCs). In one embodiment, the dendritic cells or dendritic cell precursors can also be derived from a mixed cell population containing such cells (e.g. from the circulation or from tissue or an organ). In certain embodiments, the mixed cell population containing DCs or dendritic cell precursors is enriched such that DCs or dendritic cell precursors make up greater than 50% (e.g. 50%, 55%, 60%, 65%, 70%, 75%, 80%, 85%, 90%, 95%, 98%, 99%, 99.5%, 99.9% or more) of the cell population. In some embodiments, the dendritic cells described herein are purified by separation from some or all non-dendritic cells in a cell population. In exemplary embodiments, cells can be purified such that a starting population comprising dendritic cells or dendritic cell precursors contains at least 50% or more dendritic cells or dendritic cell precursors (e.g. a purity of 50%, 55%, 60%, 65%, 70%, 75%, 80%, 85%, 90%, 95%, 98%, 99%, 99.5%, 99.9% or more).

In one embodiment, dendritic cells can be isolated using the techniques known in the art. See Inaba K, et al., Curr. Protoc. Immunol. 2009; 86:3.7.1-3.7.19 and Woo J, et al., Transplantation 1994; 58:484-4914. Those skilled in the art are able to implement modifications to the foregoing methods of isolating cells comprising dendritic cells or dendritic cell precursors without the exercise of undue experimentation. In one embodiment, dendritic cells can be purified using fluorescence-activated cell sorting for antigens present on their surface (e.g. CD11c in the case of certain dendritic cells). In one embodiment, DCs present in a starting population of cells express CD11c. In another embodiment, DCs or dendritic cell precursors present in a starting population of cells express class II molecules. A starting population of cells may be monitored for expression of various cell surface markers (e.g. including CD11c) using techniques known in the art.

In another embodiment, a population of cells comprising dendritic cells and/or dendritic cell precursors can be obtained from pluripotential cells present in blood as PBMCs. Although most easily obtainable from blood, the pluripotential cells may also be obtained from any tissue in which they reside, including bone marrow and spleen tissue. These pluripotential cells typically express CD14, CD32, CD68 and CD115 monocyte markers with little or no expression of CD83, p55 or accessory molecules such as CD40 and CD86.

In one embodiment, dendritic cell precursors can be differentiated into dendritic cells using methods known in the art prior to, during, or after treatment with at least one agent in a protocol to prepare induced tolerogenic or induced immunogenic dendritic cells. For example, when cultured in the presence of cytokines such as a combination of GM-CSF and IL-4 or IL-13, the pluripotential cells give rise to the immature dendritic cells. In another embodiment, FLT3 Ligand can be used for this purpose. For example, in one embodiment, a starting population of cells comprising dendritic cells or dendritic cell precursors can be cultured ex vivo in the presence of one or more agents which promote differentiation of DCs. In one embodiment, one or more of GM-CSF or IL-4 is used to promote the development of DCs ex vivo (e.g. by culture for 1-15 days, 2-10 days, 3-9 days, 4-8 days, or 5-6 days or such other time to obtain sufficient differentiation). In one embodiment, induced dendritic cells are fully differentiated (either prior to, during, or after induction to produce induced tolerogenic dendritic cells or induced immunogenic dendritic cells.)

In another embodiment, a starting population of cells comprising DCs or DC precursors can be obtained from PBMCs. Methods of obtaining PBMCs from blood, using methods such as differential sedimentation through an appropriate medium (e.g. Ficoll-Hypaque™, Pharmacia Biotech, Uppsala, SE), are well known and suitable for use in this invention. In a preferred embodiment of the invention, the pluripotential cells are obtained by depleting populations of PBMCs of platelets, and T and B lymphocytes. Various methods may be used to accomplish the depletion of the non-pluripotential cells. According to one method, immunomagnetic beads labeled with antibodies specific for cells to be removed (e.g. T or B lymphocytes) may be used to remove the T and B cells, either directly or indirectly, from the PBMC population. T cells may also be depleted from the PBMC population by rosetting with neuramimidase treated red blood cells. See O'Doherty U, et al., J. Exp. Med. 1993; 178:1067-1078.

As set forth above, cultures of immature dendritic cells may be obtained by culturing the pluripotential cells in the presence of cytokines which promote their differentiation for a time sufficient to achieve the desired level of differentiation (e.g. from 1-10 days, from 2-9 days, from 3-8 days, or from 4-7 days). As an example, a combination of GM-CSF and IL-4 at a concentration of each at between about 200 to about 2000 U/ml, between about 500 and 1000 U/ml, or about 800 U/ml (GM-CSF) and 1000 U/ml (IL-4) produces significant quantities of the immature dendritic cells. A combination of GM-CSF (10-200 ng/ml) and IL-4 (5-50 ng/ml) can also be used. It may also be desirable to vary the concentration of cytokines at different stages of the culture such that freshly cultured cells are cultured in the presence of higher concentrations of IL-4 (1000 U/ml) than established cultures (500 U/ml IL-4 after 2 days in culture). Other cytokines such as IL-13 may be found to substitute for IL-4.

In another embodiment, FLT3 ligand can be used for this purpose. Other protocols for this purpose are known in the art.

Methods for obtaining these immature dendritic cells from adherent blood mononuclear fractions are known in the art. See Romani N, et al., J. Exp. Med. 1994; 180(1):83-93 and Sallusto F, Lanzavecchia A, J. Exp. Med. 1994; 179: 1109-1118. Briefly, lymphocyte depleted PBMCs are plated in tissue culture plates at a density of about 1 million cells/cm in complete culture medium containing cytokines such as GM-CSF and IL-4 at concentrations of each at between about 800 to 1000 U/ml and IL-4 is present at about 1000 U/ml. Another source of immature dendritic cells is cultures of proliferating dendritic cell precursors. See Steinman R, et al., WO1993020185. Since the dendritic cells prepared from the CD34$^+$ proliferating precursors mature to dendritic cells expressing mature characteristics it is likely that they also pass through a development stage where they are pluripotential.

In one embodiment, a starting population of cells comprising dendritic cells can be enriched for the presence of mature dendritic cells by contacting the immature dendritic cells with a dendritic cell maturation factor. As referred to herein, the dendritic cell maturation factor may actually be one or more specific substances which act alone or with another agent to cause the maturation of the immature dendritic cells, for example, with one or more of an adjuvant, a TLR agonist, a CD40 agonist, an inflammasome activator, an inflammatory cytokine, or combinations thereof.

Dendritic cells can be generated in vitro from peripheral blood mononuclear cells (PBMCs) using a protocol which would basically consist of seeding PBMCs in a culture bottle such that the adhesion of said cells is allowed. After that the cells would be treated with interleukin 4 (IL4) and granulocyte-macrophage colony-stimulating factor (GM-CSF) leading to the differentiation of the cells into immature dendritic cells (iDCs) in approximately one week. Optionally, the cells can be maturated treating them with tumor necrosis factor alpha (TNFα).

Dendritic cells can be obtained using standard methods from many suitable sources. These sources for the isolation of dendritic cells include peripheral blood, spinal cord, tumor-infiltrating cells, peritumor tissue-infiltrating cells, biopsies of lymph nodes, thymus, spleen, skin, umbilical cord blood, monocytes obtained from peripheral blood, CD34- or CD14-positive cells obtained from peripheral blood, as well as any other suitable tissue or fluid.

Optionally, stable cell cultures of dendritic cells can be used. For instance, dendritic-like cell/tumor cell hybridomas and pluralities of dendritic-like cell/tumor cell hybrids may be utilized. See Falo L, et al., EP 1168924. These hybrids and hybridomas are generated from the fusion of tumor cells with dendritic-like cells. For example, immortal tumor cells from an autologous tumor cell line can be fused with autologous HLA-matched allogenic dendritic-like cells. The autologous tumor cell lines can be obtained from primary tumors and from their metastases. Alternatively, immortal dendritic-like cells of an autologous or allogenic HLA-matched dendritic-like cell line can be fused with autologous tumor cells. See Fitzpatrick D, et al., WO2002048167. Another cell line that can be used is CB1. See Paglia P, et al., J. Exp. Med. 1993; 178:1893-1901.

The antigen-loaded dendritic cells of the compositions according to the invention are prepared by contacting a dendritic cell preparation with an immunogenic composition comprising the desired antigen under conditions adequate for the pulsing of said cells with the viral immunogen.

As contemplated herein, the present invention may include use of any antigen suitable for loading into an APC to elicit an immune response. In one embodiment, microbial antigens may be used. The antigenic molecule can be, for example, but is not limited to, a viral antigen, a bacterial antigen, a fungal antigen, a protozoal antigen, an allergen or environmental antigen, a differentiation antigen, a tumor antigen, an embryonic antigen, an antigen of oncogenes and mutated tumor-suppressor genes, a unique tumor antigen resulting from chromosomal translocations or derivatives thereof. It is also possible that the antigenic polypeptide is an immunogenic fragment of a viral antigen, bacterial antigen, a fungal antigen, a protozoal antigen, an allergen or environmental antigen, a differentiation antigen or a tumor antigen. Examples of suitable antigens, include but are not limited to:

1) Viral antigens: viral antigens which are capable of eliciting an immune response against the virus include animal and human retro- and lentiviral antigens such as those of HIV-1, namely HIV-1 antigens (e.g. tat, nef, gp120 or gp160, gp40, p24, gag, env, vif, vpr, vpu, rev) or Immediate Early protein (e.g. ICP27, ICP47, ICP4, ICP36 from HSV1 or HSV2), hepatitis B virus (e.g. hepatitis B surface antigen or hepatitis core antigen), hepatitis C virus (e.g. core, E1, NS3 or NS5 antigens), from paramyxoviruses (e.g. Respiratory Syncytial virus, such as F and G proteins or derivatives thereof), from parainfluenza virus, from rubella virus (e.g. proteins E1 and E2), measles virus, mumps virus, human papilloma viruses (e.g. HPV6, 11, 16, 18, eg L1, L2, E1, E2, E3, E4, E5, E6, E7), flaviviruses (e.g. Yellow Fever Virus, Dengue Virus, Tick-borne encephalitis virus, Japanese Encephalitis Virus) or Influenza virus cells (e.g. HA, NP, NA, or M proteins, or combinations thereof), rotavirus antigens (e.g. VP7sc and other rotaviral components), and similar viruses. See Fields B, Knipe D. Eds., "Fundamental Virology", $2^{nd}$ Edition (Raven Press, New York, N.Y., 1991).

2) Bacterial antigens: bacterial antigens such as antigens from *Neisseria* spp., including *N. gonorrhea* and *N. meningitidis* (e.g. transferrin-binding proteins, lactoferrin binding proteins, PiIC and adhesins); antigens from *Streptococcus pyogenes* (e.g. M proteins or fragments thereof and C5A protease); antigens from *Streptococcus agalactiae, Streptococcus mutans; Haemophilus ducreyi; Moraxella* spp., including *M. catarrhalis*, also known as *Branhamella catarrhalis* (e.g. high and low molecular weight adhesins and invasins); antigens from *Bordetella* spp., including *B. pertussis, B. parapertussis* and *B. bronchiseptica* (e.g. pertactin, pertussis toxin or derivatives thereof, filamenteous hemagglutinin, adenylate cyclase, fimbriae); antigens from *Mycobacterium* spp., including *M. tuberculosis, M. bovis, M. leprae, M. avium, M. paratuberculosis, M. smegmatis; Legionella* spp., including *L. pneumophila*; (e.g. ESAT6, Antigen 85A, -B or -C, MPT 44, MPT59, MPT45, HSPIO, HSP65, HSP70, HSP 75, HSP90, PPD 19 kDa [Rv3763], PPD 38 kDa [Rv0934]); antigens from *Escherichia* spp., including enterotoxic *E. coli* (e.g. colonization factors, heat-labile toxin or derivatives thereof, heat-stable toxin or derivatives thereof), antigens from enterohemorragic *E. coli* and enteropathogenic *E. coli* (e.g. shiga toxin-like toxin or derivatives thereof); antigens from *Vibrio* spp., including *V. cholera* (e.g. cholera toxin or derivatives thereof); antigens from *Shigella* spp., including *S. sonnei, S. dysenteriae, S. flexnerii; Yersinia* spp., including *Y. enterocolitica* (e.g. Yop protein); antigens from *Y. pestis, Y. pseudotuberculosis; Campylobacter* spp., including *C. jejuni* (e.g. toxins, adhesins and invasins); antigens from *Salmonella* spp., including *S. typhi, S. enterica* and *S. bongori; Listeria* spp., including *L. monocytogenes; Helicobacter* spp., including *H. pylori* (e.g. urease, catalase, vacuolating toxin); antigens from *Pseudomonas* spp., including *P. aeruginosa; Staphylococcus* spp., including *S. aureus, S. epidermidis; Enterococcus* spp., including *E. faecalis, E. faecium; Clostridium* spp., including *C. tetani* (e.g. tetanus toxin and derivative thereof); antigens from *C. botulinum* (e.g. botulinum toxin and derivative thereof), antigens from *C. difficile* (e.g. *clostridium* toxins A or B and derivatives thereof); antigens from *Bacillus* spp., including *B. anthracis* (e.g. anthrax toxin and derivatives thereof); *Corynebacterium* spp., including *C. diphtheriae* (e.g. diphtheria toxin and derivatives thereof); antigens from *Borrelia* spp., including *B. burgdorferi* (e.g. OspA, OspC, DbpA, DbpB); antigens from *B. garinii* (e.g. OspA, OspC, DbpA, DbpB), *B. afzelii* (e.g. OspA, OspC, DbpA, DbpB), antigens from *B. andersonfi* (e.g. OspA, OspC, DbpA, DbpB and antigens from *B. hermsii*; antigens from *Ehrlichia* spp., including *E. equi* and the agent of the human granulocytic ehrlichiosis; *Rickettsia* spp., including *R. rickettsii; Chlamydia* spp., including *C. trachomatis* (e.g. MOMP, heparin-binding proteins); antigens from *Chlamydia pneumoniae* (e.g. MOMP, heparin-binding proteins), antigens from *C. psittaci; Leptospira* spp., including *L. interrogans; Treponema* spp., including *T. pallidum* (e.g. rare outer membrane proteins), antigens from *T. denticola, T. hyodysenteriae*, antigens from *M. tuberculosis* (e.g. Rv2557, Rv2558, RPFs: Rv0837c, Rv1884c, Rv2389c, Rv2450, Rv1009, aceA (Rv0467), PstS1, (Rv0932), SodA (Rv3846), Rv2031c 16 kDal., Tb Ra12, Tb H9, Tb Ra35, Tb38-1, Erd 14, DPV, MTI, MSL, mTTC2 and hTCC1); antigens from *Chlamydia* (e.g. High Molecular Weight Protein (HWMP), ORF3 (EP 366 412), and putative membrane proteins (Pmps); antigens from *Streptococcus* spp., including *S. pneumoniae* (PsaA, PspA, streptolysin, choline-binding proteins, the protein antigen pneumolysin, and mutant detoxified derivatives thereof); antigens derived from *Haemophilus* spp., including *H. influenzae* type B (e.g. PRP and conjugates thereof); antigens from non-typified *H. influenzae* (e.g. OMP26, high molecular weight adhesins, P5, P6, protein D and lipoprotein D, and fimbrin and fimbrin derived peptides, or multiple copy variants or fusion proteins thereof).

3) Fungal antigens: fungal antigens such as antigens from *Candida* spp., including *C. albicans; histoplasma* fungal antigens (e.g. heat shock protein 60 (HSP60) and other *histoplasma* fungal antigen components); antigens from *Cryptococcus* spp., including *C. neoformans* (e.g. capsular polysaccharides and other cryptococcal fungal antigen components); *coccidiodes* fungal antigens (e.g. spherule antigens and other *coccidiodes* fungal antigen components); and tinea fungal antigens (e.g. trichophytin and other *coccidiodes* fungal antigen components).

4) Prootozoal antigens: protozoal antigens such as antigens from *Plasmodium* spp., including *P. falciparum* (e.g. merozoite surface antigens, sporozoite surface antigens, circumsporozoite antigens, gametocyte/gamete surface antigens, blood-stage antigen pf, 55/RESA) and other plasmodial antigen components (e.g. RTS.S, TRAP, MSP1, AMA1, MSP3, EBA, GLURP, RAPT, RAP2, Sequestrin, PfEMP1, Pf332, LSAT, LSA3, STARP, SALSA, PfEXP1, Pfs25, Pfs28, PFS27/25, Pfs16, Pfs48/45, Pfs230 and their analogues in *Plasmodium* spp.); antigens from *Toxoplasma* spp. and *T. gondii* (e.g. SAG2, SAGS, Tg34, p30 and other toxoplasmal antigen components); schistosomae antigens (e.g. glutathione-S-transferase, paramyosin, and other schistosomal antigen components); leishmania major and other leishmaniae antigens (e.g. gp63, lipophosphoglycan and its associated protein and other leishmanial antigen components); and *Trypanosoma cruzi* antigens (e.g. the 75-77 kDa antigen, the 56 kDa antigen and other trypanosomal antigen components), antigens from *Entamoeba* spp., including *E. histolytica*; *Babesia* spp., including *B. microti*; *Trypanosoma* spp., including *T. cruzi*; *Giardia* spp., including *G. lamblia*; *leishmania* spp., including *L. major*; *Pneumocystis* spp., including *P. carinii*; *Trichomonas* spp., including *T. vaginalis*; *Schisostoma* spp., including *S. mansoni*.

5) Allergen or environmental antigens: allergen or environmental antigens such as naturally occurring allergens like as pollen allergens (e.g. tree-, herb, weed-, and grass pollen allergens), insect allergens (e.g. inhalant, saliva and venom allergens), animal hair and dandruff allergens, and food allergens. Important pollen allergens from trees, grasses and herbs originated from the taxonomic orders of Fagales, Oleales, Pinoles and platanaceae including La birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including (e.g. grasses of the genera *Lolium, Phleum, Poa, Cynodon, Dactylis, Holcus, Phalaris, Secale*, and *Sorghum*), the orders of Asterales and Urticales (e.g. herbs of the genera *Ambrosia, Artemisia*, and *Parietaria*). Other allergen antigens that may be used include allergens from house dust mites of the genus *Dermatophagoides* and *Euroglyphus*, storage mite (e.g. *Lepidoglyphys, Glycyphagus* and *Tyrophagus*), those from cockroaches, midges and fleas (e.g. *Blatella, Periplaneta, Chironomus* and *Ctenocepphalides*), those from mammals (e.g. cat, dog and horse), birds, venom allergens including such originating from stinging or biting insects (e.g. from the taxonomic order of Hymenoptera including bees (superfamily Apidae), wasps and ants (superfamily Formicoidae)). Still other allergen antigens that may be used include inhalation allergens from fungi (e.g. from the genus *Alternaria* and *Cladosporium*).

6) Tumoral antigens: tumoral antigens such as MAGE, MART-1/Melan-A, gp100, Dipeptidyl peptidase IV (DPPIV), adenosine deaminase-binding protein (AD-Abp), cyclophilin b, Colorectal associated antigen (CRC)-0017-1A/GA733, Carcinoembryonic Antigen (CEA) and its antigenic epitopes CAP-1 and CAP-2, etv6, aml1, Prostate Specific Antigen (PSA) and its antigenic epitopes PSA-1, PSA-2, and PSA-3, prostate-specific membrane antigen (PSMA), T-cell receptor/CD3-ç; chain, MAGE-family of tumor antigens (e.g. MAGE-A1, MAGE-A2, MAGE-A3, MAGEA4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g. GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p2lras, RCAS1, α-fetoprotein, E-cadherin, α-catenin, 13-catenin, γ-catenin, p12Octn, gp100$^{Pme1117}$, PRAME, NY-ESO-1, cdc27, adenomatous polyposis coli protein (APC), fodrin, Connexin 37, Immunoglobuline-idiotype (Ig-idiotype), p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL40), SSX-3, SSX-4, SSX-5, SCP-1 and CT-7, and c-erbB-2, acute lymphoblastic leukemia (etv6, amll, cyclophilin b), B cell lymphoma (Ig-idiotype), glioma (E-cadherin, a-catenin, 13-catenin, 7-catenin, p120ctn), bladder cancer (p2lras), biliary cancer (p2lras), breast cancer (MUC family, HER2/neu, c-erbB-2), cervical carcinoma (p53, p2lras), colon carcinoma (p2lras, HER2/neu, c-erbB-2, MUC family), colorectal cancer (Colorectal associated antigen (CRC)-0017-1A/GA733, APC), choriocarcinoma (CEA), epithelial cell cancer (cyclophilin b), gastric cancer (HER2/neu, c-erbB-2, ga733 glycoprotein), hepatocellular cancer, Hodgkins lymphoma (lmp-1, EBNA-1), lung cancer (CEA, MAGE-3, NY-ESO-1), lymphoid cell-derived leukemia (cyclophilin b), melanoma (p15 protein, gp75, oncofetal antigen, GM2 and GD2 gangliosides, MelanA/MART-1, cdc27, MAGE-3, p2lras, gp100$^{Pme1117}$), myeloma (MUC family, p2lras), non-small cell lung carcinoma (HER2/neu, c-erbB-2), nasopharyngeal cancer (lmp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ES0-1), and T cell leukemia (HTLV-1 epitopes).

In a preferred embodiment, the antigen used to obtain the antigen-loaded dendritic cells of the invention is a viral antigen. In a more preferred embodiment, the viral antigen is a HIV antigen.

As disclosed previously, HIV isolates are classified into discrete genetic subtypes. HIV-1 is known to comprise at least ten subtypes (A1, A2, A3, A4, B, C, D, E, PL F2, G, H, j and K). See Taylor B, et al., N. Engl. J. Med. 2008; 359(18):1965-1966. HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India, and China, areas where the incidence of new HIV infections is high, HIV-1 subtype B accounts for only a small minority of infections, and subtype HIV-1 C appears to be the most common infecting subtype. Thus, in certain embodiments, it may be preferable to select immunogens from particular subtypes (e.g. HIV-1 subtypes B or C). It may be desirable to include immunogens from multiple HIV subtypes (e.g. HIV-1 subtypes B and C HIV-2 subtypes A and B, or a combination of HIV-1, HIV-2, or HIV-3 subtypes) in a single immuno logical composition.

Suitable HIV immunogens include HIV envelope (env; e.g. NCBI Ref. Seq. NPJ357856), gag (e.g. p6, p7, p17, p24, GenBank AAD39400J), the protease encoded by pol (e.g. UniProt P03366), nef (e.g. fenBank-CAA4I 585J, Shugars D, et al., J. Virol. 1993; 67(8):4639-4650), as well as variants, derivatives, and fusion proteins thereof. See Gómez C, et al., Vaccine 2007; 25:1969-1992. Suitable strains and combinations may be selected by the skilled artisan as desired.

The antigen-loaded dendritic cell, otherwise known as a "pulsed dendritic cell" of the invention, is produced by exposure of the dendritic cell to an antigen either in vitro or in vivo. In the case where the dendritic cell is pulsed in vitro, the dendritic cell can be plated on a culture dish and exposed to an antigen in a sufficient amount and for a sufficient period of time to allow the antigen to bind to the dendritic cell. The amount and time necessary to achieve binding of the antigen to the dendritic cell may be determined by using methods known in the art or otherwise disclosed herein. Other methods known to those of skill in the art, for example immunoassays or binding assays, may be used to detect the presence of antigen on the dendritic cell following exposure to the antigen.

In a further embodiment of the invention, the dendritic cell may be transfected with a vector which allows for the expression of a specific protein by the dendritic cell. The protein which is expressed by the dendritic cell may then be processed and presented on the cell surface. The transfected dendritic cell may then be used as an immunogenic composition to produce an immune response to the protein encoded by the vector. Vectors may be prepared to include a specific polynucleotide which encodes and expresses a protein to which an immunogenic response is desired. Preferably, retroviral vectors are used to infect the cells. More preferably, adenoviral vectors are used to infect the cells.

In another embodiment, a vector may be targeted to an dendritic cell by modifying the viral vector to encode a protein or portions thereof that is recognized by a receptor on the dendritic cell, whereby occupation of the dendritic cell receptor by the vector will initiate endocytosis of the vector, allowing for processing and presentation of the antigen encoded by the nucleic acid of the viral vector. The nucleic acid which is delivered by the virus may be native to the virus, which when expressed on the dendritic cell encodes viral proteins which are then processed and presented on the MHC receptor of the dendritic cell.

As contemplated herein, various methods can be used for transfecting a polynucleotide into a host cell. The methods include, but are not limited to, calcium phosphate precipitation, lipofection, particle bombardment, microinjection, electroporation, colloidal dispersion systems (i.e. macromolecule complexes, nanocapsules, microspheres, beads, and lipid-based systems including oil-in-water emulsions, micelles, mixed micelles, and liposomes). These methods are understood in the art and are described in published literature so as to enable one skilled in the art to perform these methods.

In another embodiment, a polynucleotide encoding an antigen can be cloned into an expression vector and the vector can be introduced into a dendritic cell to otherwise generate a loaded dendritic cell. Various types of vectors and methods of introducing nucleic acids into a cell are discussed in the available published literature. For example, the expression vector can be transferred into a host cell by physical, chemical or biological means. See Brown T, "Gene Cloning" (Chapman & Hall, London, GB, 1995); Watson R, et al., "Recombinant DNA", 2nd Ed. (Scientific American Books, New York, N.Y., US, 1992); Alberts B, et al., "Molecular Biology of the Cell" (Garland Publishing Inc., New York, N.Y., US, 2008); Innis M, et al., Eds., "PCR Protocols. A Guide to Methods and Applications" (Academic Press Inc., San Diego, Calif., US, 1990); Erlich H, Ed., "PCR Technology. Principles and Applications for DNA Amplification" (Stockton Press, New York, N.Y., US, 1989); Sambrook J, et al., "Molecular Cloning. A Laboratory Manual" (Cold Spring Harbor Laboratory Press, Cold Spring Harbor, N.Y., US, 1989); Bishop T, et al., "Nucleic Acid and Protein Sequence. A Practical Approach" (IRL Press, Oxford, GB, 1987); Reznikoff W, Ed., "Maximizing Gene Expression" (Butterworths Publishers, Stoneham, Mass., US, 1987); Davis L, et al., "Basic Methods in Molecular Biology" (Elsevier Science Publishing Co., New York, N.Y., US, 1986), Schleef M, Ed., "Plasmid for Therapy and Vaccination" (Wiley-VCH Verlag GmbH, Weinheim, Del., 2001).

It is readily understood that the introduction of the expression vector comprising a polynucleotide encoding an antigen yields a pulsed cell. The present invention includes various methods for pulsing dendritic cells including, but not limited to, loading dendritic cells with whole antigen in the form of a protein, cDNA or mRNA. However, the invention should not be construed to be limited to the specific form of the antigen used for pulsing the dendritic cell. Rather, the invention encompasses other methods known in the art for generating an antigen loaded dendritic cell. Preferably, the dendritic cell is transfected with mRNA encoding a defined antigen. mRNA corresponding to a gene product whose sequence is known can be rapidly generated in vitro using appropriate primers and reverse transcriptase-polymerase chain reaction (RT-PCR) coupled with transcription reactions. Transfection of a dendritic cell with mRNA provides an advantage over other antigen-loading techniques for generating a pulsed APC. For example, the ability to amplify RNA from a microscopic amount of tissue (i.e. tumor tissue), extends the use of the APC for vaccination to a large number of patients.

Once the dendritic cells have been pulsed with the antigen of interest, the immunogen-pulsed dendritic cells are recovered. Different strategies can be used to recover the immunogen-pulsed dendritic such as immunoisolation using any marker expressed by mature cells such as, for example CD80.

Once the antigen of interest is loaded into immature dendritic cells, said cells can be submitted to in vitro maturation with cytokines, TLR (toll-like receptor) ligands and other agents. For example, the skilled in the art knows that a cocktail of pro-inflammatory cytokines, IL-1β, IL-6 and TNFα in combination with prostaglandin $E_2$ may be employed to mature DC for immunotherapy of HIV. Another alternative is to mature DC with a combination of inflammatory cytokines, TNFα, IL-2, IFNγ and IFNα, and dsRNA poly I:C (termed αDCI). The product obtained is suitable for being used as a therapeutic or prophylactic vaccine.

The expression of cell surface markers can be determined, for example, by means of flow cytometry using conventional methods and apparatuses. For example, the Calibur FACS (fluorescent-activated cell sorting, Becton Dickinson Co., Franklin Lakes, N.J., US) system using commercially available antibodies and usual protocols known in the art can be used. Thus, the cells presenting a signal for a specific cell surface marker in the flow cytometry above the background signal can be selected. The background signal is defined as the signal intensity given by a non-specific antibody of the same isotype as the specific antibody used to detect each surface marker in the conventional FACS analysis. In order for a marker to be considered positive, the observed specific signal has to be more than 20%, preferably, 30%, 40%, 50%, 60%, 70%, 80%, 90%, 500%, 1000%, 5000%, 10000% or above, intense in relation to the intensity of the background signal using conventional methods and apparatuses.

Said dendritic cell vaccine is preferably autologous to the subject. The most effective immunotherapeutic vaccines utilize antigen based on autologous HIV (i.e. the quasi-species of virus unique to each host). The most impressive results in anti-HIV immunotherapy trials to date have used dendritic cells (DCs) loaded with whole, inactivated HIV virions derived from the patients' autologous virus. The dendritic cells are also obtained from the same patient. In a preferred embodiment the dendritic cell preparation is autologous to the subject from which the CD4+ T cells and the CD14+ monocytes have been isolated.

The term "inhibitor of the interaction between sialoadhesin and sialyllactose" has been defined above. In a preferred embodiment, the inhibitor is selected from the group consisting of sialyllactose, a molecule comprising a sialyllactose moiety and an anti-sialoadhesin antibody. In another preferred embodiment, the molecule comprising a sialyllactose moiety is a ganglioside having less than four sialic acids. In another preferred embodiment, the ganglio side containing sialyllactose and having less than four sialic acids is selected from any ganglioside shown in Table 1 or any combination gangliosides shown in Table 1. In a preferred embodiment, the compositions of the invention comprise at least 2, at least 3, at least 4, at least 5, at least 6, at least 7, at least 8, at least 9, at least 10 or more gangliosides wherein said gangliosides are selected from the gangliosides in Table 1 or correspond to any other gangliosides carrying sialyllactose.

The composition and kit-of-parts according to the invention can be used for generating an immune response in a subject against the antigen which is loaded in the antigen-presenting cell. The antigen-presenting cells will act a vaccine inducing priming of CD4+ and CD8+ cells in the subject while the presence of the inhibitor of the interaction between sialoadhesin and sialyllactose will prevent that, if the subject is infected with HIV, the antigen-presenting cells will not take up any virus and re-infect CD4+ T cells in the patient. Thus, while the compositions and kits-of-parts are particularly useful for the treatment of a disease associated with HIV infection (using antigen-presenting cells loaded with HIB antigen or mixtures of antigens), they are also useful for the treatment of diseases concomitant with HIV infection by promoting the stimulation of an immune response against an antigen which forms part of the cells causing the disease while minimizing further spreading of HIV by preventing uptake of HIV by antigen-presenting cells forming part of the immunogen/vaccine composition.

Thus, in another aspect, the invention relates to a composition or kit-of-parts according to the invention for use in medicine.

In another aspect, the invention relates to an immunogen or vaccine comprising composition or kit-of-parts according to the invention.

In another aspect, the invention relates to a composition or kit-of-parts according to the invention for use in the treatment or prevention of a disease which requires an immune response against the antigen which is loaded in the antigen-presenting cell.

In another aspect, the invention relates to the composition or kit-of-parts according to the invention for the preparation of a medicament for the treatment in a subject of a disease associated which requires an immune response against the antigen which is loaded in the antigen-presenting cell.

In a preferred embodiment, the subject to which the composition or kit-of-parts is administered is a HIV-infected patient.

In another aspect, the invention relates to a method of treatment of a subject afflicted with a disease which requires an immune response against an antigen or antigens which comprises the administration to said subject of a composition or kit-of-parts according to the invention wherein the antigen-presenting cells in said composition or kit-of-parts is loaded with said antigen or antigens against which an immune response is required.

The dendritic cell vaccine of the invention can be a therapeutic vaccine, that is, a material given to already HIV infected subjects that have developed AIDS to help fight the disease by modulating their immune responses. Therapeutic HIV vaccines represent promising strategy as an adjunct or alternative to current antiretroviral treatment options for HIV.

The dendritic cell vaccine of the invention can be a prophylactic AIDS vaccine designed to be administered to an already HIV infected subject that has not developed AIDS.

The generation of an immune response to HIV may be evaluated by measuring, for instance, viral load, T-cell proliferation, T-cell survival, cytokine secretion by T-cells, or an increase in the production of antigen-specific antibodies (e.g. antibody concentration).

Methods for the detection of stimulated T cells are known to the skilled person. However, the person skilled in the art can easily construe that any method suitable for assessing the stimulation of T cells in response to an Ag can be used. The procedures described below provide a few examples of suitable methods:

1) Enzyme-linked immunospot (ELISpot): non-adherent cells from pre-culture wells are transferred to a plate which has been coated with the desired anti-cytokine capture antibodies (Abs; e.g. anti-IFN, -IL-10, -IL-2, -IL-4). Revelation is carried out with biotinylated secondary Abs and standard colorimetric or fluorimetric detection methods such as streptavidin-alkaline phosphatase and NBT-BCIP and the spots counted. ELISpot readouts are then expressed as spot-forming cells (SFC)/$10^6$ PBMCs.
2) Supernatant cytokine assay: cytokines released in the culture supernatant are measured by different techniques, such as enzyme-linked immunosorbent assays (ELISA), BD cytometric bead array, Biorad Bio-Plex assay and others.
3) HLA Class II tetramers: with this procedure, Ag-reactive T cells recognizing specific peptide epitopes are detected, using either commercially available reagents (e.g. MHC Class II Ultimers™, ProImmune Ltd, Oxford, GB) or in-house generated ones (e.g. Novak E, et al., J. Clin. Invest. 1999; 104:R63-R67).
4) Upregulation of activation markers (e.g. CD69, CD25, CD137): with this procedure, Ag-specific T cell responses are detected by their differential expression of activation markers exposed on the membrane following Ag-recognition.
5) Cytokine capture assays: this system is a valid alternative to the ELISpot to visualize Ag-specific T cells according to their cytokine response (Miltenyi Biotec GmbH, Bergisch Gladbach, Del.). In addition, it allows the direct sorting and cloning of the T cells of interest.

6) CD154 assay: this procedure is limited to detection of Ag-specific CD4+ T cells. See Chattopadhyay P, et al., Nat. Med. 2005; 11:1113-11117 and Frentsch M, et al., Nat. Med. 2005; 11:1118-1124.
7) CD107 assay: this procedure allows the visualization of Ag-specific CD8+ T cells with cytotoxic potential. See Betts M, et al., J. Immunol. Methods 2003; 281:65-78.
8) CFSE dilution assay: this procedure detects Ag-specific T cells (CD4+ and CD8+) according to their proliferation following Ag recognition. See Mannering S, et al., J. Immunol. Methods 2003; 283:173-183.

5. Methods for the Detection and Isolation of Enveloped Viruses

The identification of the interaction between sialoadhesin and sialyllactose moieties present in certain gangliosides found in the envelope of enveloped viruses allows the detection of said virus by determining their ability for binding to sialoadhesin as well as the isolation of said virus by separating the virus bound to sialoadhesin from other components present in the sample. The detection and isolation method of the present invention can identify HIV virions by using a lipidic marker of the envelope rather than protein markers. This is significant, because viral protein markers mutate at a great rate during infection, such that no single viral detection system will be as effective for detecting viral infection in different patients, or for isolating virus from an individual patient. This method is useful, therefore, as a diagnostic assay for the detection or isolation of HIV from a sample as well as for the isolation of HIV. Thus, in another embodiment, the invention relates to a method for detecting an enveloped virus in a sample comprising:
(i) contacting said sample with sialoadhesin or a functionally equivalent variant thereof substantially preserving its ability to bind sialyllactose, and
(ii) detecting the virus bound to said sialoadhesin or functionally equivalent variant thereof.

The term "functionally equivalent variant", when referred to sialoadhesin, is understood as all those polypeptides derived from the sialoadhesin by means of modification, insertion or deletion of one or more amino acids, provided that the function of binding to siallylactose or molecules containing siallylactose within their backbone is substantially preserved.

Functionally equivalent variants of sialoadhesin which retain substantial binding activity for sialyllactose are those wherein the affinity towards sialyllactose is of at least $10^{15}$ $M^{-1}$, $10^{14}$ $M^{-1}$, $10^{13}$ $M^{-1}$, $10^{12}$ $M^{-1}$, $10^{10}$ $M^{-1}$ or $10^{9}$ $M^{-1}$. In another embodiment, functionally equivalent variants of sialoadhesin suitable for use in the present invention include those which show at least a 99%, 98%, 97%, 96%, 95%, 94%, 93%, 92%, 91%, 90%, 85%, 80%, 75%, 70%, 65%, 60%, 55%, 50%, 45%, 40%, 35%, 30% or less of the binding activity of the naturally occurring sialoadhesin to sialyllactose or to sialyllactose containing molecules.

Suitable functionally equivalent variants of sialoadhesin can be identified using standard assays for determining the binding affinity of sialoadhesin to siallylactose or to cells comprising gangliosides which contain siallylactose-containing gangliosides in the surface. For instance, suitable functionally equivalent variants of sialoadhesin can be identified by using a solid-phase assay based on the ability of immobilized sialoadhesin to bind to human erythrocytes which have been derivatized to contain sialic acid in different linkages (e.g. NeuAca2-3Galb1-3GalNAc, NeuAca2-3Galb1-3(4)GlcNAc, or NeuAca2-6Galb1-4GlcNAc). See Vinson M, et al., J. Biol. Chem. 1996; 271:9267-9272). As control for the assay, underivatized erythrocytes can be used. Alternatively, suitable functionally equivalent variants of sialoadhesin can be identified by utilizing a solid-phase assay based on the detection of the binding by immobilized fusion proteins comprising sialoadhesin of polyacrylamide-containing glycoconjugates (e.g. NeuAcα2,3Galβ1,4Glc or NeuAcα2,6Galβ1,4Glc). See Hartnell A, et al., Blood 2001; 97:288-296.

Functionally equivalent variants can also be those showing a degree of identity with respect to sialoadhesin higher than at least 25%, at least 40%, at least 60%, at least 70%, at least 80%, at least 90%, at least 95%, at least 96%, at least 97%, at least 98% or at least 99%.

In a first step, the diagnostic method according to the invention involves the contacting of a sample suspected to contain an enveloped virus with sialoadhesin.

The sample to be analyzed according to the method of the present invention includes biological samples that are fluids (e.g. sera, blood, urine, saliva, pancreatic juice, cerebrospinal fluid, semen) as well as any fluidic biological sample (e.g. tissue or biopsy extracts, extracts of feces, sputum) may likewise be employed in the assays of the present invention. Most preferably, the biological sample being assayed will be serum or plasma.

Detection assays based on binding typically involve the use of a solid phase material to which the detection reagent becomes bound, but may be adapted to involve the binding of non-immobilized antigens and antibodies (i.e. a solution-phase immunoassay). The reaction product is separated from excess sample, assay reagents, and other substances by removing the solid phase from the reaction mixture (e.g. by washing). Thus, in a preferred embodiment, the sialoadhesin or functionally equivalent variant thereof is immobilized.

Any of a wide variety of solid supports may be employed in the assays of the present invention. Suitable materials for the solid support are synthetics such as polystyrene, polyvinyl chloride, polyamide, or other synthetic polymers, natural polymers such as cellulose, as well as derivatized natural polymers such as cellulose acetate or nitrocellulose, and glass, especially glass fibers. The support can take the form of spheres, rods, tubes, and microassay or microtiter plates. Sheet-like structures such as paper strips, small plates, and membranes are likewise suitable. The surface of the carriers can be permeable and impermeable for aqueous solutions.

In a preferred embodiment, the enveloped virus is selected from the group consisting of HIV or Ebola virus. In a still more preferred embodiment, the HIV is HIV-1.

In a second step, the detection method according to the invention comprises the detection of the enveloped viruses bound to the said sialoadhesin or functionally equivalent variant thereof.

Detection of enveloped virions can be performed using a variety of techniques known in the art, and include detection of the enveloped virus genome and more preferably, detection of enveloped virus nucleic acids (i.e. RNA or DNA as the case may be) and detection of enveloped virus proteins. Methods of detecting RNA and protein expression are well known in the art and have been described in general above. In one aspect, the enveloped virus is HIV. In another embodiment, detection of HIV is carried out by the binding of an antibody against one or more HIV proteins. Suitable proteins of HIV that can be used for the detection include, without limitation, polypeptides present in the HIV envelope (env; e.g. NCBI Ref. Seq. NPJ357856), gag (e.g. p6, p'7, p17, p24, GenBank AAD39400J), the protease encoded by pol (e.g. UniProt P03366), nef (e.g. fenBank-CAA4I 585J, Shugars, 1993, supra).

In accordance with a preferred embodiment of the present invention, the sialoadhesin or functionally equivalent variant thereof is bound to a solid support (i.e. immobilized) and incubated in contact with the biological sample being tested for the presence of an anti-HIV antibody. A blocking agent may be added to reduce non-specific binding.

As will be appreciated, the sialoadhesin or functionally equivalent variant thereof may be incubated with the biological sample in an unbound state and then subsequently bound to the solid support (i.e. immobilizable). The supports are then preferably extensively treated (e.g. by washing) to substantially remove unspecifically bound components. In consequence of such treatment, complexes between sialoadhesin or a functionally equivalent variant thereof and the enveloped virus may form.

One type of solid phase assay that may be used in accordance with the present invention is a sandwich assay. In the sandwich assay, the label present on the solid phase is directly proportional to the amount of analyte present in the sample. This type of assay format is generally preferred, especially for the visualization of low analyte concentrations, because the appearance of label on the solid phase is more readily detected.

A detectably labeled antibody (capable of binding to a component of the enveloped virus) is then preferably added and the support is incubated under conditions sufficient to permit the antibody to bind to any enveloped virus that may be present. The support is then preferably extensively treated (e.g. by washing) to substantially remove any unbound antibody. If enveloped viruses are present in the test sample, then the antibody and the enveloped virus will form an immune complex. In such an assay, the detection of antibody bound to the support is indicative of the presence of enveloped virus in the sample being tested. See Schuurs A, et al., U.S. Pat. No. 4,016,043 and by Pankratz T, et al., U.S. Pat. No. 5,876,935. The antibody may be a natural immunoglobulin isolated from nonhuman species (e.g. anti-human IgG murine antibody, antihuman IgG goat antibody, antihuman IgM goat antibody), or it can be produced recombinantly or synthetically. It may be an intact immunoglobulin, or an immunoglobulin fragment (e.g. FAb, F(Ab)$_2$). As desired, other binding molecules (capable of binding to enveloped viruses) may be employed in concert with or in lieu of such antibodies. For example, the antibodies can be biotinylated and the second antibody can be replaced with labeled avidin or streptavidin.

To eliminate the bound-free separation step and reduce the time and equipment needed for a chemical binding assay, a homogeneous assay format may alternatively be employed. In such assays, one component of the binding pair may still be immobilized; however, the presence of the second component of the binding pair is detected without a bound-free separation. Examples of homogeneous optical methods are the EMIT method (Syva, Inc., Sunnyvale, Calif., US), which operates through detection of fluorescence quenching; the laser nephelometry latex particle agglutination method (Behringwerke GmbH, Marburg, Del.), which operates by detecting changes in light scatter; the LPIA latex particle agglutination method (Mitsubishi Chemical Industries Ltd., Tokyo, JP); the TDX fluorescence depolarization method (Abbott Laboratories, Inc., Abbott Park, Ill., US); and the fluorescence energy transfer method (CisBio International SA, Paris, FR). Any of such assays may be adapted for use in accordance with the objectives of the present invention.

The binding assay of the present invention may be configured as a competitive assay. In a competitive assay, the higher the concentration of enveloped virus present in the test sample, the lower the amount of label present on the solid phase.

In a manner similar to the sandwich assay, the competitive assay can be conducted by providing a defined amount of a labeled enveloped virus and determining whether the fluid being tested contains enveloped virus of the same type that would compete with the labeled antibody for binding to the support. In such a competitive assay, the amount of captured labeled enveloped virus is inversely proportional to the amount of analyte present in the test sample.

In all such assay formats, at least one component of the assay reagents will preferably be labeled or otherwise detectable by the evolution or quenching of light. Such component may be a second antibody, anti-HIV antibody, or the peptide that binds to the anti-HIV antibody, depending on the immunoassay format employed. Radioisotopic-binding assay formats (e.g. a radioimmunoassay) employ a radioisotope as such label; the signal is detectable by the evolution of light in the presence of a fluorescent or fluorogenic moiety. See Lucas F, et al., U.S. Pat. No. 5,698,411 and Landrum E, et al., U.S. Pat. No. 5,976,822. Enzymatic-binding assay formats (e.g. ELISA) employ an enzyme as a label; the signal is detectable by the evolution of color or light in the presence of a chromogenic or fluorogenic moiety. Other labels, such as paramagnetic labels, materials used as colored particles, latex particles, colloidal metals such as selenium and gold, and dye particles may also be employed. See Leuvering J, U.S. Pat. No. 4,313,734, Gribnau T, et al., U.S. Pat. No. 4,373,932, and Baugher B, et al., U.S. Pat. No. 5,501,985) The use of enzymes (especially alkaline phosphatase, β-galactosidase, horse radish peroxidase, or urease) as the detectable label (i.e. an enzyme immunoassay or EM) is preferred.

The presence of enzymatic labels may be detected through the use of chromogenic substrates (including those that evolve or adsorb fluorescent, UV, visible light) in response to catalysis by the enzyme label. When the enzyme is alkaline phosphatase, the substrate may include chemo luminescent substrates such as AMPPD® (3-(2'-spiroadamantane)-4-methoxy-4-(3"-phosphoryloxy)phenyl-1,2-dioxetane), CDP-Star® (disodium 4-chloro-3-(methoxyspiro{1,2-dioxetane-3,2'-(5'-chloro)tricyclo[3.3.1.1$^{3,7}$] decan}-4-yl)phenyl phosphate) and CSPD® (disodium 3-(4-methoxyspiro {1,2-dioxetane-3,2-(5'-chloro)tricyclo [3.3.1.1$^{3,7}$]decan}-4-yl)phenyl phosphate); chromogenic substrates such as p-nitrophenyl phosphate, 5-bromo-4-chloro-3-indolyl-phosphate (BCIP), 4-nitroblue tetrazolium chloride (NBT) and iodo nitro tetrazolium (INT).

More preferably, chemical labels may be employed (e.g. colloidal gold, latex bead labels). Detection of label can be accomplished using multiple detectors, multipass filters, gratings, or spectrally distinct fluors. See Ward D, et al., U.S. Pat. No. 5,759,781. It is particularly preferred to employ peroxidase as an enzyme label, especially in concert with the chromogenic substrate 3,3',5,5'-tetramethylbenzidine (TMB), OPD, or ABTS. In the case of labeling of the antibodies with peroxidase as enzyme, it is possible to use the periodate technique or a heterobifunctional reagent. See Nakane P, et al., J. Histochem. Cytochem. 1974; 22:1084-1090 and Ishikawa E, et al., J. Immunoassay. 1983; 49(3): 209-327.

Materials for use in the assay of the invention are ideally suited for the preparation of a kit. Such a kit may contain one or more container means, such vials or tubes; each of the container means comprising one of the separate elements to be used in the realization of the assay test. For example, one of the container means may comprise a sialoadhesin or functionally equivalent variant thereof, a second container may comprise soluble, detectably labeled anti-enveloped virus, preferably in lyophilized form, or in solution. In addition, the kit may also contain one or more containers, each of which comprises a (different) predetermined amount of an enveloped virus or lipid particles containing gangliosides which contain sialyllactose moieties. These latter containers can be used to prepare a standard curve into which can be interpolated the results obtained from the sample containing the unknown amount of enveloped virus.

In using the kit, the user just requires to add to a container a premeasured amount of a sample suspected of containing a measurable yet unknown amount of enveloped virus, a premeasured amount of the detectably labeled antibody present in the second container. After an appropriate time for incubation, an immune complex is formed (if the sample contained enveloped virus) and is separated from the supernatant fluid, and the immune complex or the supernatant fluid are detected, as by radioactive counting, addition of an enzyme substrate, and color development, or by inclusion of a chemical label (e.g. colloidal gold, latex beads).

In another embodiment, the invention provides a method for the isolation of enveloped viruses from a sample comprising:
(i) contacting said sample with sialoadhesin or a functionally equivalent variant thereof substantially preserving its ability to bind sialyllactose, and
(ii) isolating the virus bound to said sialoadhesin or functionally equivalent variant thereof.

In a preferred embodiment, the sialoadhesin or the functionally equivalent variant thereof may be bound to matrices and used for the affinity purification of enveloped viruses from, for example, cell cultures, or biological tissues such as blood and liver. The sialoadhesin or functionally equivalent variant thereof, for example, may be attached to or immobilized on a substrate or support. The solution containing the enveloped viruses' determinants is then contacted with the immobilized sialoadhesin for a time and under conditions suitable for the formation of complexes between the sialoadhesin and the enveloped viruses. The conditions used during the contacting step are controlled (e.g. by pH or salt concentration, i.e. ionic strength in the solution). Care should be taken not to exceed the capacity of the amount of sialoadhesin or variant thereof (i.e. the flow should be sufficiently slow to allow a satisfactory adsorption). In this step, other components of the solution will pass through in principle unimpeded. Optionally, the matrix is then washed (e.g. with an aqueous solution), in order to remove retained or loosely bound substances.

In a next step unbound material is separated from the bound complexes. The enveloped viruses are then separated from the support. The separation (aka elution) is usually carried out using a second solution denoted an eluent which is passed over the matrix under conditions that provide desorption (i.e. release of HIV from the sialoadhesin or variant thereof). Such conditions are commonly provided by a change of pH or salt concentration (e.g. ionic strength, hydrophobicity). Various elution schemes are known, such as gradient elution and step-wise elution. Elution can also be provided by a second solution comprising a competitive substance, which will replace the HIV on the matrix.

In a preferred embodiment, the enveloped virus is selected from the group consisting of HIV or Ebola virus. In a still more preferred embodiment, the HIV is HIV-1.

In another embodiment, the invention provides a kit comprising immobilized sialoadhesin or a functionally equivalent variant thereof substantially preserving its ability to bind sialyllactose. The immobilized sialoadhesin or functionally equivalent variant thereof is useful for the detection of enveloped virus in a sample as well as for the isolation of enveloped virus.

The support to which the sialoadhesin is bound can, for example, in the form of separate particles, preferably porous and essentially spherical particles; a monolith; or a membrane. Also encompassed by the invention is a system suitable for performing affinity chromatography, which comprises the use of a separation matrix column as defined above. The column may be of a size suitable for analytical scale or for large scale chromatography.

Suitable support materials are well known. In one embodiment, the support is a natural polymer (e.g. agarose, alginate, carrageenan, gelatine). Such natural polymers are known to form physically cross-linked networks spontaneously on cooling or on addition of divalent metal ions, and chemical cross-linkers can be added if desired. These supports are easily prepared according to standard methods, such as inverse suspension gelation. See Hjerten S, Biochim. Biophys. Acta 1964; 79(2):393-398. In another embodiment, the support is comprised of cross-linked synthetic polymers (e.g. styrene or styrene derivatives, divinylbenzene, acrylamides, acrylate esters, methacrylate esters, vinyl esters, vinyl amides). Such polymers are also easily produced according to standard methods. See Arshady R, Chimica e L' Industria 1988; 70(9):70-75. Thus, in summary, the support material can in principle be any material that allows the covalent coupling of the gp120 binding compounds of the invention (e.g. the above-discussed polymers, inorganic materials, such as silica, ceramics).

Many well-known methods are available for immobilizing ligands to a support through suitable functional groups. The exact choice of coupling method will depend on the structure of the ligand to be immobilized. In one embodiment, the support has hydrophilic surfaces, and if porous, the surfaces of the pores are also hydrophilic. This is advantageous in order to avoid or at least reduce any non-specific protein interactions. It is also advantageous if the surfaces have a high density of groups available for coupling of ligands. Such coupling groups are commonly hydroxyl groups, but may also include other radicals such as groups with double bonds available for grafting, amines, thiols or epoxides. If the support material has undesirable surface properties, it is possible to coat it with a hydrophilic polyhydroxy-functional material before coupling the ligand. The techniques and considerations for coupling affinity ligands to a suitable support to prepare a separation matrix are known in the art. See Berg H, et al., WO1998033572.

6. Conjugates of the Invention

The identification of sialoadhesin as specific ligand for sialyllactose residues present in the gangliosides found in the envelope of enveloped virus allows the use of this molecule for the targeting to enveloped viruses of compounds of interest by coupling said compounds to sialoadhesin. The sialoadhesin or functionally equivalent variant thereof can furthermore be linked (i.e. directly or through a spacer molecule) to a therapeutic drug or to a dye, a fluorescent molecule, a diagnostic enzyme, or a radiolabeled entity to enable identification of enveloped viruses or to therapeutically target enveloped viruses.

Thus, in another embodiment, the invention relates to a conjugate comprising sialoadhesin or a functionally equivalent variant thereof substantially preserving its ability to bind sialyllactose and a therapeutic agent.

In a preferred embodiment, the therapeutic agent is an anti-HIV agent. In another preferred embodiment, the anti-HIV agent is selected from the group consisting of an entry and fusion inhibitor, an integrase inhibitor, a reverse transcriptase inhibitor and a protease inhibitor.

The conjugate of the invention can be obtained using any method known for a person skilled in the art. It is thus possible to obtain sialoadhesin or the variant of said protein by any standard method. For example, sialoadhesin can be obtained by purification from cells wherein the polypeptide occurs in nature (e.g. macrophages) or by recombinant means from cDNA by means of expression in a heterologous organism such as, for example, Escherichia coli, Saccharomyces cerevisiae, or Pichia pastoris. Once a sufficient amount of the purified sialoadhesin or functionally equivalent variant thereof is available, the latter must be conjugated to the compound of interest. The conjugation can be carried out in different ways. One possibility is the direct conjugation of a functional group to the agent of interest in a position which does not interfere with the activity of said component. As understood in the present invention functional groups refer to a group of specific atoms in a molecule which are responsible for a characteristic chemical reaction of said molecule. Examples of functional groups include, without limitation, hydroxy, aldehyde, alkyl, alkenyl, alkynyl, amide, carboxamide, primary, secondary, tertiary and quaternary amines, aminoxy, azide, azo (diimide), benzyl, carbonate, ester, ether, glyoxylyl, haloalkyl, haloformyl, imine, imide, ketone, maleimide, isocyanide, isocyanate, carbonyl, nitrate, nitrite, nitro, nitroso, peroxide, phenyl, phosphine, phosphate, phosphono, pyridyl, sulfide, sulfonyl, sulfinyl, thioester, thiol and oxidized 3,4-dihydroxyphenylalanine (DOPA) groups. Examples of said groups are maleimide or glyoxylyl groups, which react specifically with thiol groups in the Apo A molecule and oxidized 3,4-dihydroxyphenylalanine (DOPA) groups which react with primary amino groups in the EDA molecule.

Another possibility is to conjugate therapeutic agent to sialoadhesin or functionally equivalent variant thereof by means of the use of homo- or heterobifunctional groups. The bifunctional group can first be conjugated to the therapeutically active compound and, then, conjugated to the sialoadhesin or, alternatively, it is possible to conjugate the bifunctional group to the sialoadhesin and, then, conjugate the latter to the therapeutic agent. Illustrative examples of this type of conjugates include the conjugates known as ketone-oxime in which the first component of the conjugate comprises an aminoxy group which is bound to a ketone group present in a heterobifunctional group which, in turn, is bound to an amino group in the second component of the conjugate. See Lam K, et al., US20050255042.

In another embodiment, the agent used to conjugate the sialoadhesin and the therapeutic agent can be photolytically, chemically, thermically or enzymatically processed. In particular, the use of linking agents which can be hydrolyzed by enzymes that are in the target cell, such that the therapeutically active compound is only released into the cell, is of interest. See McCall J, et al., WO2004054622, Chien H, et al., WO2006107617, Chan C, et al., WO2007046893 and Govindan S, WO2007112193.

In a preferred embodiment, wherein the therapeutically active compound is a compound of a peptide nature including both oligopeptides, peptides and proteins, it is possible to chemically modify a polypeptide chain using widely known methods to the person skilled in the art so that the protein can be covalently coupled to a second polypeptide. Thus, suitable methods for the covalent coupling of two polypeptides include methods based on the conjugation through the thiol groups present in the cysteine moieties, methods based on the conjugation through the primary amino groups present in the lysine moieties, methods based on the conjugation through the N- and C-terminal moieties can be used. See Morseman J, et al., U.S. Pat. No. 6,809,186. Reagents suitable for the modification of polypeptides to allow their coupling to other compounds include: glutaraldehyde (i.e. allows binding compounds to the N-terminal end of polypeptides), carbodiimide (i.e. allows binding the compound to the C-terminal end of a polypeptide), succinimide esters (e.g. MBS, SMCC) which allow activating the N-terminal end and cysteine moieties, benzidine (BDB), which allows activating tyrosine moieties, and periodate, which allows activating carbohydrate moieties in those proteins which are glycosylated.

In the particular case in which the therapeutically active compound is of a peptide nature, it is possible to express the conjugate in a single step using a gene construct of the invention encoding said conjugate, for which said construct is introduced in a vector suitable for its expression in a heterologous organism together with transcription and, optionally, translation control elements. The transcription and, optionally, translation control elements present in the expression cassette of the invention include promoters, which direct the transcription of the nucleotide sequence to which they are operatively linked and other sequences which are necessary or suitable for the transcription and its suitable regulation in time and place, for example, initiation and termination signals, cleavage sites, polyadenylation signal, replication origin, transcriptional enhancers, or transcriptional silencers. Said elements, as well as the vectors used for constructing the expression cassettes and the recombinant vectors according to the invention are generally chosen according to the host cells to be used.

The compositions of the invention may be administered to the mammal (including a human) to be treated by any means well known in the art (e.g. orally, intranasally, subcutaneously, intramuscularly, intradermal, intravenously, intra-arterially, parenterally or by catheterization).

The invention further relates to the use of a composition comprising sialoadhesin or a functionally equivalent variant thereof as carrier for targeting one or more viral inhibitors to provide a synergistic effect against a viral infection, preferably a HIV/AIDS viral infection. Within the framework of this embodiment, the viral inhibitor is selected from the group consisting of an entry and fusion inhibitor, an integrase inhibitor, a reverse transcriptase inhibitor and a protease inhibitor.

More generally, the invention relates to the conjugates of sialoadhesin and a suitable detectable label as conventionally used, such as a fluorescent label, a luminescent label, a chemoluminiscent label, an enzyme label, a radioactive label, or an absorbance label.

The conjugates of the invention may be administered to a subject in need thereof for the treatment or prevention of diseases associated with an infection by an enveloped virus. Thus, in another aspect, the invention relates to a conjugate according to the invention for use in the treatment of a disease caused by an infection by an enveloped virus.

In another aspect, the invention relates to the use of a conjugate according to the invention for the manufacture of a medicament for the treatment of a disease caused by an infection by an enveloped virus.

In another aspect, the invention relates to a method for the treatment of a disease caused by an infection by an enveloped virus in a subject in need thereof comprising the administration to said subject of a conjugate according to the invention.

In a preferred embodiment, the disease caused by an infection by an enveloped virus is selected from the group consisting of a disease caused by a virus of the filoviridae family and a disease caused by a retrovirus.

In a preferred embodiment, the enveloped virus is HIV, in which case the conjugates are used for the treatment of a disease associated with an HIV infection.

7. Methods for Delivering a Compound of Interest to an Antigen Presenting Cell In another embodiment, the invention relates to a method for delivering a compound of interest to an antigen-presenting cell which comprises contacting said antigen-presenting cell with a lipid microvesicle comprising said compound and wherein said lipid particle comprises at least a molecule containing a sialyllactose moiety.

Compounds that can be delivered to antigen-presenting cells using the method of the invention include, without limitation:

1) Antigens. Suitable antigens include one or more of the viral antigens, bacterial antigens, fungal antigens, prootozoal antigens, allergen or environmental antigens or tumoral antigens defined above.
2) An antiretroviral agent as defined above. Preferably, the antiretroviral agent is selected from the group consisting of an entry and fusion inhibitor, an integrase inhibitor, a reverse transcriptase inhibitor and a protease inhibitor.
3) A nucleic acid (e.g. dsRNA, immune-stimulating oligonucleotides, plasmids, antisense and ribozymes)
4) Radioisotopes such as 125I, 131I, 111In, 123I, 99 mTc, and 32P. Such compositions are useful, for example, in treating subjects having autoimmune diseases with aberrant dendritic cell activity. Elimination of dendritic cells by toxins may ease autoimmune diseases (e.g. multiple sclerosis, rheumatoid arthritis, autoimmune diseases).
5) Enzymatically active toxins and fragments thereof such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. Such compositions are useful, for example, in treating subjects having autoimmune diseases with aberrant dendritic cell activity. Elimination of dendritic cells by toxins may ease autoimmune diseases (e.g. multiple sclerosis, rheumatoid arthritis).
6) Immunosuppressive drugs such as certain glucorticoids (e.g. dexamethasone, tacrolimus, Cyclosporin A) that inhibit the maturation and allostimulatory capacity of DCs by downregulating the expression of costimulatory molecules (i.e. CD80 and CD86) and the secretion of inflammatory cytokines (i.e. IL-6 and TNF-α).
7) A compound having a detectable group. The detectable group can be any material having a detectable physical or chemical property like a spectroscopic, photochemical, biochemical, immunochemical, electrical, optical or chemical means. Useful labels in the present invention include fluorescent dyes (e.g. fluorescein isothiocyanate, Alexa dyes, Texas red, rhodamine), radiolabels and calorimetric labels such as colloidal gold or colored glass or plastic (e.g. polystyrene, polypropylene, latex) beads.

In a preferred embodiment, the compound of interest is an antigen. In a second aspect, the compound is an antiretroviral agent. Preferably, the compound is an antigen.

Reagents suitable for producing liposomes include, but are not limited to, phospholipids. The liposomes may contain glycerophospholipids, sphingolipids or a combination thereof.

Glycerophospholipids suitable for preparing liposomes according to the invention include, without limitation:

1) glycerophospholipids containing unsaturated fatty acids such as distearoyl-phosphatidylglycerol (DSPG), 1,2-distearoyl-s/z-glycero-3-phosphocholine (DSPC), dioleoyl phosphatidyl choline (DOPC), dioleoyl phosphatidylglycerol (DOPG), phosphatidylglycerol (PC), phosphatidic acid (PA), and/or phosphatidylglycerol (PG),
2) glycerophospho lipids containing saturated fatty acids such as dimyristoylphosphatidylcho line (DMPC), dipalmitoyl phosphatidylcho line (DPPC), dipalmitoyl phosphatidic acid (DPPA), and dipalmitoyl phosphatidylglycerol (DMPG) can also be used in liposome production, and
3) glycerophospho lipids containing saturated and unsaturated lipids such as 1-palmitoyl-2-oleoyl-sn-glycero-3-phosphocholine (POPC) and 1,2-dipalmitoyl-sn-glycero-3-phosphocholine (DPPC).

Sphingolipids suitable for preparing liposomes according to the invention include, without limitation, shpingomyelin.

Stearylamine can be used when cationic liposomes are preferred, and natural acidic lipids, such as phosphatidylserine (PS), PG, phosphatidylinositol (PI), PA, and cardiolipin (CL) can be added when anionic liposomes are desired. In some embodiments, cholesterol can be included to stabilize a liposome bilayer. Small amounts of antioxidants, including but not limited to α-tocopherol or β-hydroxytoluidine (BHT), can be included when polyunsaturated neutral lipids are used.

Liposomes range in size from 20 nanometers to over 1000 nanometers. Accordingly, liposomes may be 20 nm, 25 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 950 nm, or 100 nm. In exemplary embodiments, the liposomes range from 100 nm to 200 nm. The size of the liposomes can be controlled by methods such as sonication and filtration. Liposomes are diverse and can be formed in different sizes and lipid compositions. See Basu S, Basu M, Liposome methods and protocols, methods in molecular biology, Vol. 199, "Liposome Technology", $3^{rd}$ Ed., Gregoriadis G, Ed. (Informa HealthCare Inc., New York, N.Y., US, 2006).

It will be appreciated that the ratio of the different components may be adjusted at will. In a preferred embodiment, the liposomes contain, in addition to the molecules containing a sialyllactose moiety, glycerolipids, cholesterol and sphigomyelin.

In a preferred embodiment, the ratio of glycerolipids to cholesterol is 41/45. In a preferred embodiment, the ratio of glycerolipids to sphingolipids (preferably sphingolmyelin is 41/10. In another embodiment, the ratio of cholesterol to sphingolipids is 9/2 (w/w).

In a preferred embodiment, the glycerolipids are 1-palmitoyl-2-oleoyl-sn-glycero-3-phosphocholine (POPC), 1,2-dipalmitoyl-sn-glycero-3-phosphocholine (DPPC) or a combination thereof. In a still more preferred embodiment, the liposomes contain a 25/16 ratio of POPC to DPPC. In another embodiment, the liposomes contain 25% mol of POPC, 16% mol of DPPC, 45% mol of cholesterol and sufficient sphingomyelin to arrive to 100% mol. In a preferred embodiment, the liposomes contain 4% gangliosides, in which case the content of sphingomyelin is 10%.

Gangliosides suitable for use in the present invention include any ganglioside containing a sialyllactose residue and less than 4 sialic acid residues. In a preferred embodiment, the molecule containing a sialyllactose moiety is a ganglioside that contains less than four sialic acid groups. In a more preferred embodiment, the gangliosides are as shown in Table 1. In a still more preferred embodiment, the ganglioside is selected from the group consisting of GM1, GM2, GM3, GD1b and GT1b.

The core of the liposome is aqueous and can be used to hold the compound which is to be delivered to the antigen-presenting cell. In a preferred embodiment, the compound is an antigenic polypeptide, such as an immunogenic fragment of a viral antigen, bacterial antigen, a fungal antigen, a protozoal antigen, an allergen or environmental antigen, a differentiation antigen or a tumor antigen. In a more preferred embodiment, the antigen is a viral antigen. In a still more preferred embodiment, the antigen is an HIV antigen.

In a preferred embodiment, the antigen-presenting cell is a sialoadhesin-expressing cell. In a more preferred embodiment, the antigen-presenting cell is a dendritic cell.

In one embodiment, the methods described herein are used in ex vivo therapy. For example, a lipid microvesicle comprising a compound of interest and wherein said lipid particle comprises at least a molecule containing a sialyllactose moiety can be contacted with an immune cell (e.g. a sialoadhesin-expressing cells and, more preferably, a dendritic cell) in vitro, such that that the compound is taken up by the cell. The cell is then transferred to a patient (e.g. by injection) to treat a disorder (e.g. a cancer or autoimmune disease). In one embodiment, immune cells (e.g. dendritic cells) are extracted from the patient, contacted with the lipid microvesicle comprising a compound of interest such that the agent is taken up into the cells.

Alternatively, the lipids microvesicles comprising a compound of interest can also be used for delivery of the compounds to cells in vivo, using methods which are known to those of skill in the art. For in vivo administration, the lipid microvesicles are typically administered parenterally (i.e. intraarticularly, intravenously, intraperitoneally, subcutaneously, intramuscularly, or subdermally, such as by an implanted device). In particular embodiments, the pharmaceutical compositions are administered intravenously or intraperitoneally by a bolus injection. See Stadler J, et al., U.S. Pat. No. 5,286,634. Methods of intracellular nucleic acid delivery are also known in the art. See Straubringer K, et al., "Methods in Enzymology" (Academic Press, New York, N.Y., US, 1983, pp. 512-527), Mannino R, et al., Biotechniques 1988; 6:682-690, Nicolau C, et al., Crit. Rev. Ther. Drug Carrier Syst. 1989; 6:239-271. Still other methods of administering lipid-based therapeutics have been previously described. See Rahman Y, et al., U.S. Pat. No. 3,993,754, Sears B, U.S. Pat. No. 4,145,410, Schneider S, U.S. Pat. No. 4,224,179, Papahadjopoulos D, et al., U.S. Pat. No. 4,235,871, Lenk R, et al., U.S. Pat. No. 4,522,803, and Fountain M, et al., U.S. Pat. No. 4,588,578.

In another embodiment, the lipids microvesicles comprising a compound of interest can also be used for delivery of the compounds to cells in vitro.

All publications mentioned hereinabove are hereby incorporated in their entirety by reference.

Having now generally described the invention, the same will be more readily understood through reference to the following examples, which are provided by way of illustration, and are not intended to be limiting of the present invention, unless specified.

General Procedures

1. Isolation of HIV-1 and Mass Spectrometry Analysis

MT-4 cells were infected with HIV-1$_{NL4-3}$ and co-cultured with uninfected cells. Virus was harvested before cytopathic effects were observed and purified. See Lorizate, 2009, supra. Briefly, the medium was cleared by filtration, and particles were concentrated by ultracentrifugation through a cushion of 20% (w/w) sucrose. Concentrated HIV-1 was further purified by velocity gradient centrifugation on an OptiPrep™ gradient (Axis-Shield PoC, Oslo, NO).

The visible virus fraction was collected and concentrated by centrifugation. The final pellet was resuspended in 10 mM Hepes, 150 mM NaCl (pH 7.4) buffer, rapidly frozen in liquid nitrogen and stored at −80° C. For lipid composition analysis, samples were resuspended in methanol upon thawing and then assessed in a UPLC coupled to an orthogonal acceleration time-of-flight mass spectrometer with an electrospray ionization interface (LCT Premier; Waters Corp., Milford, Mass., US). Data were acquired using positive ionization mode over a mass range of m/z 50-1500 in W-mode. A scan time of 0.15 s and interscan delay of 0.01 s were used at a nominal instrument resolution of 11500 (FWHM). Leucine-enkephalin was used as the lock spray calibrant.

2. Primary Cell Cultures

Peripheral blood mononuclear cells (PBMCs) were obtained from HIV-1-seronegative subjects and monocyte populations (>97% CD14$^+$) were isolated with CD14$^+$ positive selection magnetic beads (Miltenyi Biotec GmbH, Bergisch Gladbach, DE). DCs were obtained culturing these cells in the presence of 1,000 U/ml of granulocyte-macrophage colony-stimulating factor (GM-CSF) and IL-4 (R&D). The mDCs were differentiated by culturing iDCs at day five for two more days in the presence of 100 ng/ml of lipopolysaccharide (LPS; Sigma-Aldrich Co., Saint Louis, Mo., US). The DCs were immunophenotyped at day 7 as previously described. See Izquierdo-Useros, 2007, supra. Adequate differentiation from monocytes to iDCs was based on the loss of CD14 and the acquisition of DC-SIGN, while DC maturation upregulated the expression of CD83, CD86, and HLA-DR.

Peripheral blood mononuclear cells (PBMCs) were obtained from HIV-1-seronegative donors, and monocyte populations or myeloid DCs were isolated and cultured as described in Izquierdo-Useros N. et al. (J. Virol., 2007, 81: 7559-7570). Monocyte-derived mature DCs were differentiated for 48 h with 100 ng/ml of LPS (Sigma-Aldrich) or ITIP (300 IU/ml IL-1β, 1,000 IU/ml IL-6, 1,000 IU/ml TNF-alfa, all from CellGenix, and 1 µg/ml PGE2 from Sigma-Aldrich). LPS myeloid DCs were differentiated for 24 h with 100 ng/ml of LPS. Autologous and heterologous CD4⁺ T cells were enriched from PBMCs using the RosetteSep α-CD8⁺ cocktail (Stem cell) and maintained in RPM1 with 10% fetal bovine serum (FBS, Invitrogen) supplemented with 10 IU/ml of IL-2 (Roche).

3. Cell Lines, Plasmids and Viral Stocks

The HEK-293T cell line was maintained in a D-MEM medium (Invitrogen Corp., Carslbad, Calif., US), while the CHO and MT4 cell lines were maintained in α-MEM and RPMI media, respectively. All media contained 10% fetal bovine serum, 100 U/ml of penicillin and 10 μg/ml of streptomycin (Invitrogen Corp., Carslbad, Calif., US). $VLP_{HIV\text{-}Gag\text{-}eGFP}$ were obtained by transfecting the molecular clone pGag-eGFP (NIH AIDS Research and Reference Reagent Program, NIH, Bethesda, Md., US). The HEK-293T cells were transfected with calcium phosphate (CalPhos; BD Biosciences Corp., Franklin Lakes, N.J., US) in T75 flasks using 30 μg of plasmid DNA. The CHO cells were electroporated (0.24 Kv and 950 μF) using $7 \times 10^6$ cells and 40 μg of plasmid DNA. Supernatants containing VLPs were filtered (Millex HV, 0.45 μm; Millipore Corp., Billerica, Mass., US) and frozen at −80° C. until use. For studies with concentrated VLPs, medium was harvested, cleared by filtration, and particles were concentrated by ultracentrifugation (28,000 rpm 2 hour at 4° C. in SW32 rotor) through 20% (w/w) sucrose. The final pellet was resuspended in 150 mM NaCl, 10 mM Hepes pH 7.4 (Hepes-Sodium buffer), rapidly frozen in liquid nitrogen and stored at −80° C. The $p24^{Gag}$ content of the infectious viral stocks and $VLP_{HIV\text{-}Gag\text{-}eGFP}$ were determined by an ELISA (PerkinElmer Inc., Waltham, Mass., US) and by a quantitative western blot. Detection was carried out with aLiCoR Odyssey system employing an internally developed rabbit anticapsid pAb and purified Gag protein as a standard.

HEK-293T and TZM-bl (obtained through the U.S. National Institutes of Health [NIH] AIDS Research and Reference Reagent Program, from J C Kappes, X Wu, and Tranzyme Inc.) were maintained in D-MEM (Invitrogen). Raji B cell line (kindly provided by Y. van Kooyk) was cultured in RPMI (Invitrogen). Raji DC-SIGN B cell line (kindly provided by Y. van Kooyk) was maintained in RPMI with 1 mg/ml of G418 (Invitrogen). All media contained 10% FBS, 100 IU/ml of penicillin, and 100 μg/ml of streptomycin (all from Invitrogen). $VLP_{HIV\text{-}Gag\text{-}eGFP}$ and $VLP_{HIV\text{-}Gag\text{-}Cherry}$ were obtained as previously described (Izquierdo-Useros N. et al. Blood 113: 2732-2741). $HIV_{NL4\text{-}3}$ was obtained following transfection of the molecular clone pNL4-3 (NIH AIDS Research and Reference Reagent Program from M. Martin). $HIV_{NL4\text{-}3\text{-}Cherry}$ was obtained following cotransfection of pCHIV and pCHIV mCherry in a 1:1 ratio [Lampe M. et al. Virology 360: 92-104). $HIV_{NL4\text{-}3}$ lacking the envelope glycoprotein was obtained as described elsewhere [Izquierdo-Useros N. et al. supra). The p24Gag content of the viral stocks and VLP was determined by ELISA (Perkin-Elmer) or by a quantitative Western blot [Izquierdo-Useros N. et al. PLoS Biol 10: e1001315. doi: 10.1371/journal.pbio.1001315]. $HIV_{NL4\text{-}3}$ used in infectious assays was titrated employing the TZM-bl reporter cell line as described in [L1 M. et al., 2005, J. Viol. 79: 10108-10125.].

4. Production of Liposomes

Large unilamellar vesicles (LUVs) were prepared following an extrusion method described previously. See Mayer L, et al., Vesicles Biochim. Biophys. Acta 1986; 858:161-168. Lipids and gangliosides were acquired commercially (Avanti Polar Lipids, Inc., Alabaster, Ala., US; Santa Cruz Biotechnology, Inc., Santa Cruz, Calif., US). The $LUV_{HIV\text{-}tRed}$ lipid composition was: 1-palmitoyl-2-oleoyl-sn-glycero-3-phosphocholine (POPC) 25 mol %:1,2-dipalmitoyl-sn-glycero-3-phosphocholine (DPPC) 16 mol %:brain Sphingomyelin (SM) 14 mol %:Cholesterol (Chol) 45 mol % and when Cer, PS or Gangliosides were present (4 mol %) the SM amount was reduced to 10 mol %. The $LUV_{POPC\text{-}tRed}$ lipid composition was 96 mol % POPC containing or not 4 mol % of Cer, GM3, GM2 or GM 1. All the LUVs contained 2 mol % of 1,2-dihexadecanoyl-sn-glycero-3-phosphoethanolamine (DHPE)-Texas Red (Molecular Probes; Invitrogen Corp., Carslbad, Calif., US). Lipids were mixed in chloroform:methanol (2:1) and dried under nitrogen. Traces of organic solvent were removed by vacuum pumping for 1 to 2 h. Subsequently, the dried lipid film was dispersed in 10 mM Hepes, 150 mM NaCl (pH 7.4) and subjected to 10 freeze-thaw cycles prior to extruding 10 times through two stacked polycarbonate membranes with a 100 nm pore size (Nucleopore, Inc., Pleasanton, Calif., US) using the Thermo-barrel extruder (Lipex extruder; Northern Lipids, Inc., Burnaby, Calif.). In order to perform mDC pulse with equal concentrations of LUV displaying similar fluorescence intensities, Texas Red containing LUVs concentration was quantified following Bottcher's phosphate determination method and the fluorescence emission spectra was recorded setting the excitation at 580 nm in a SLM Aminco series 2 spectrofluorimeter (Spectronic Instruments Inc., Rochester, N.Y., US). See Bottcher C, et al., Anal. Chimica Acta 1961; 24:203-204.

5. Liposome and VLP Capture Assays

All capture experiments were performed pulsing mDCs in parallel at a constant rate of 100 μM of distinct $LUV_{tRed}$ formulations and 75 ng of $VLP_{HIV\text{-}Gag\text{-}eGFP}$Gag quantified by western blot (2,500 pg of $VLP_{HIV\text{-}Gag\text{-}eGFP}$ $p24^{Gag}$ estimated by ELISA) per $2 \times 10^5$ cells for 4 h at 37° C. After extensive washing, positive DCs were acquired by FACS with a FACSCalibur (Biosciences Corp., Franklin Lakes, N.J., US) using CellQuest software (Becton Dickinson Co., Franklin Lakes, N.J., US) to analyze the collected data. Forward-angle and side-scatter light gating were used to exclude dead cells and debris from all the analysis.

Competition experiments were done incubating $2 \times 10^5$ mDCs with 75 ng of $VLP_{HIV\text{-}Gag\text{-}eGFP}$Gag at a final concentration of $1 \times 10^6$ cells/ml for 4 h at 37° C. in the presence of decreasing amounts of GM2-containing $LUV_{HIV\text{-}tRed}$ or 100 μM of Cer- and PS-containing $LUV_{HIV\text{-}tRed}$. Alternatively, cells were incubated with 75 ng of $VLP_{HIV\text{-}Gag\text{-}eGFP}$ Gag and 100 μM of $LUV_{HIV\text{-}tRed}$ including or not GM1, GD1b, GT1b, GQ1b, Cer and PS. Cells were then analyzed by FACS as previously described.

6. Neuraminidase Treatment of VLPs and LUVs

A total of $2 \times 10^5$ DCs were pulsed for 2 h at 37° C. with 25 μM of GM3-containing $LUV_{HIV\text{-}tRed}$ and 75 ng of sucrose-pelleted $VLP_{HIV\text{-}Gag\text{-}eGFP}$ Gag treated or not during 12 h at 37° C. with 100 or 50 mU of neuraminidase from *Clostridium perfringens* Factor X Sigma-Aldrich Co., Saint Louis, Mo., US). The 12 h incubation was done in a glass-coated plate (SMI-LabHut Ltd., Churcham, Gloucestershire, GB) in Hepes-Sodium buffer, and the reaction was stopped adding RPMI media containing FCS. Cells were washed and assessed by FACS to obtain the percentage of tRed and eGFP positive cells.

7. Lactose and GM3 Polar Head Group Treatment of mDCs mDCs were preincubated with or without 5 or 10 mM of lactose (Sigma-Aldrich Co., Saint Louis, Mo., US) and soluble GM3 carbohydrate head group (Carbosynth Ltd., Compton, Berkshire, GB) for 30 min at RT. Cells were then pulsed with 50 μM of GM3-containing $LUV_{HIv\text{-}tRed}$ and 75 ng of sucrose-pelleted $VLP_{HIV\text{-}Gag\text{-}eGFP}$ Gag for 2 h at 37° C., at a final concentration of 5 or 10 mM for the compounds tested. Cells were analyzed by FACS as described previously.

8. Minimization of Ganglioside Energy Structures and Statistical Analysis

Minimal energy structures in vacuum were computed using Chem3D Ultra software (CambridgeSoft Corp., Cambridge, Mass., US) employing the MM2-force field and the steepest-descent-algorithm. Minimum root mean square gradient was set to 0.1; minimum and maximum move to 0.00001 and 1.0, respectively. Statistics were performed using GraphPad Prism v.5 software (GraphPad Software, Inc., La Jolla, Calif., US).

9. Transduction of DCs

VSV-G-Pseudotyped SIV3 lentivector (kindly provided by A. Cimarelli) was produced as in Goujon C. et al., Gene Ther., 2006, 13: 991-994). Isolated monocytes ($5 \times 10^5$) were infected with SIV3 particles and transduced with two different SIGLEC1-specific or one nontarget shRNA control MISSION Lentiviral Transduction Particles (Sigma-Aldrich) at an MOI=50. Transduced monocytes were differentiated into LPS mDCs and assessed for VLP capture and HIV-1 trans-infection as described above. Adequate phenotypic maturation of DCs was evaluated as in Izquierdo-Useros N. et al. supra. Lentiviral transduction particles carrying the GFP reporter gene cloned in the same pLKO.1-puro vector backbone (MISSION TurboGFP Control Transduction Particles) were used to evaluate transduction efficiency by FACS (estimated 75%-98% at day 7, when cells were employed).

10. Siglec-1 Surface Expression Analysis by FACS

DCs were blocked with 1 mg/ml of human IgG (Baxter, Hyland Immuno) and stained with anti-Siglec-1-PE 7-239 mAb (AbD Serotec) following the manufacturer's instructions at 4° C. for 20 min. Samples were analyzed with FACSCalibur (Becton-Dickinson) using CellQuest and FlowJo software to evaluate collected data.

11. Trans-Infection Assays

DCs were treated and pulsed with $HIV_{NL4-3}$ as described above. After extensive washing, cells were co-cultured with the TZM-bl CD4$^+$ target cell line to measure trans-infection. Pulsed monocyte derived DCs or myeloid DCs were co-cultured in quadruplicate or duplicate at a ratio of 1:1 or 5:1, respectively. Cells were assayed for luciferase activity 48 h later (BrightGlo Luciferase System; Promega) in a Fluoroskan Ascent FL luminometer (Thermo Labsystems). Background values consisting of non-HIV-1-pulsed co-cultures or reporter CD4' cells alone were subtracted for each sample. To detect possible productive infection of pulsed cells or re-infection events, some DCs were cocultured in the presence of 0.5 µM of the protease inhibitor Saquinavir.

12. Transfection of Siglec Constructs

Raji cells ($2 \times 10^6$) were transfected with vector backbone pCMV6-Entry (Origene) comprising the coding region of Siglec-1, Siglec-5, or Siglec-7 using Amaxa nucleofector as recommended by the manufacturer. At 36 h posttransfection, cells were assessed for VLP capture and HIV-1 trans-infection (at a ratio 2:1) as described above. When indicated, cells were pre-incubated with decreasing concentrations of 3'-Sialyllactose (Carbosynth) or Lactose (Sigma-Aldrich) 30 min prior to VLP pulse. In experiments with envelope-deficient viruses, $5 \times 10^5$ cells were pulsed with 100 ng of $p24^{Gag}$ estimated by ELISA for 4 h at 37° C. and assessed for capture and trans-infection (at a ratio 2:1) as aforementioned. HEK-293T cells were transfected using Fugene HD (Promega) and assessed 24 h posttransfection as described for Raji cells. Trans-infection of HEK-293T was tested in a different luminometer (Luminoskan Ascent, Thermo Labsystems), and collected data were normalized to 100%. Transfection efficiency in both cell types was assessed staining cells with anti-Siglec-1-PE 7-239 mAb, anti-Siglec-7-PE 5-386 mAb (AbD Serotec), and anti-Siglec-5/14-PE 1A5 mAb (Biolegend) and evaluated by FACS. Stable Raji DC-SIGN cells were labeled with anti-DC-SIGN-PE DCN46 mAb (BD Pharmigen).

13. Statistical Analysis

Statistics were performed using paired t test (considered significant at p<0.01) or Spearman correlation with GraphPad Prism v.5 software.

Example 1

Gangliosides in the Outer Leaflet of HIV-1 or Vesicular Membranes can Act as Viral Attachment Factors Yielding mDC Uptake Glycosphingolipids are enriched in raft-like plasma membrane domains from where HIV-1 is thought to bud. Based on this premise, the potential role of glycosphingolipids for HIV-1 capture of mDCs was investigated. The presence of GM3 in $HIV_{NL4.3}$ derived from the T-cell line MT-4 was confirmed by mass spectrometry. In addition, several other gangliosides including GM1, GM2 and GD1 were also detected in the HIV-1 membrane. See FIGS. 1A, 1B and 1C.

Figure 6:
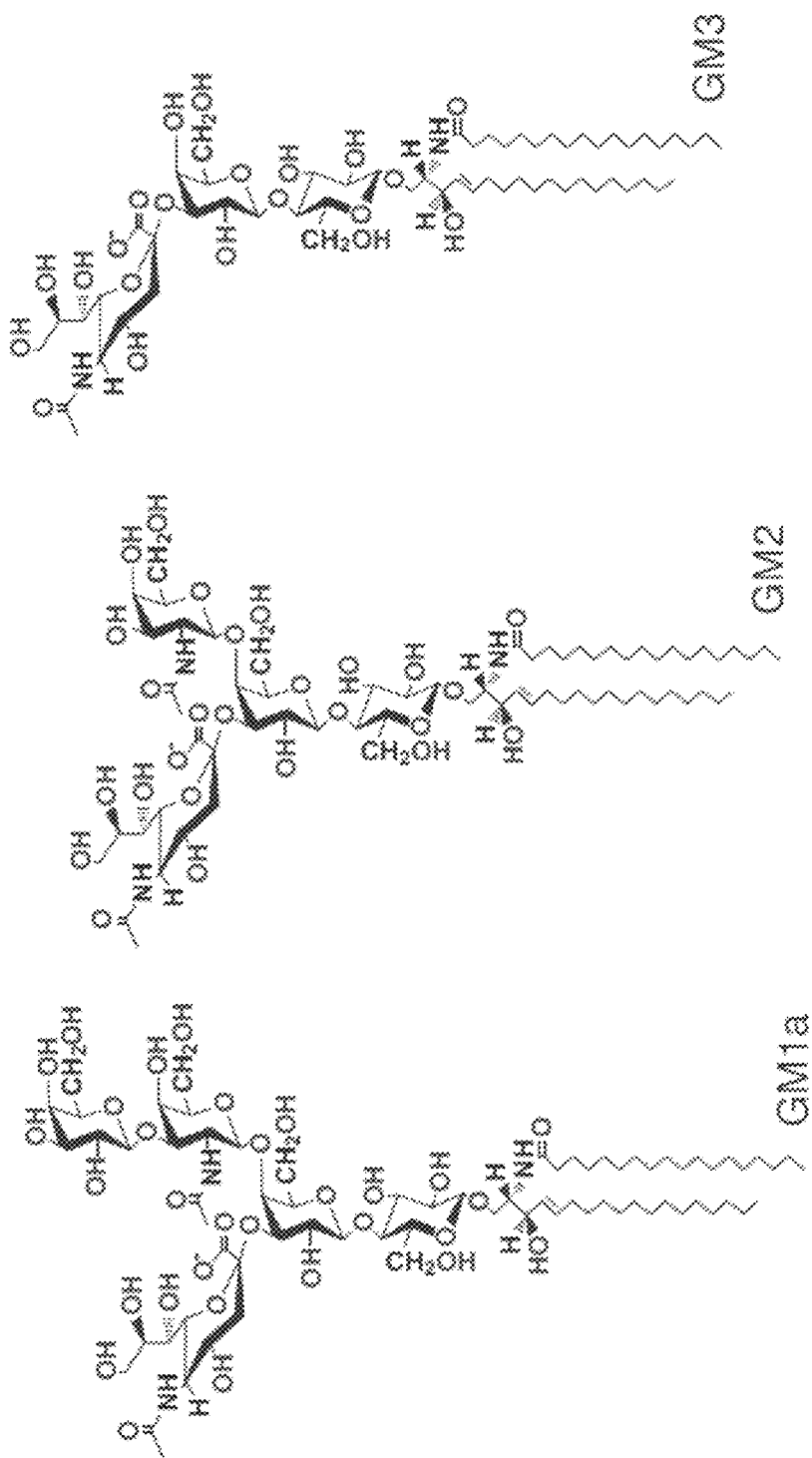
FIG. 6. Ganglioside structures. 2D model of asialo-, mono-, di-, tri- and tetrasialogangliosides used in this study.
Figure 6:
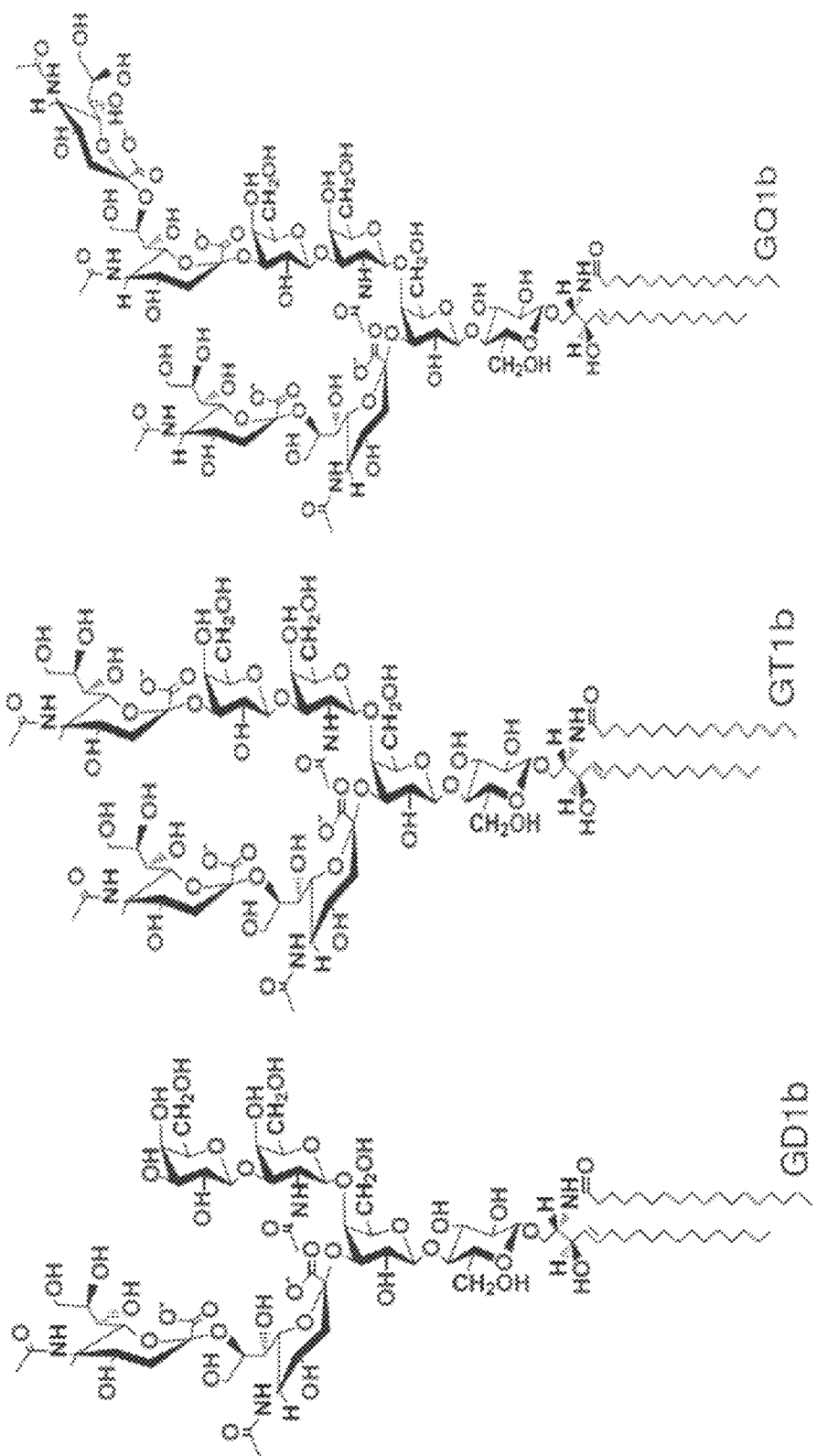
Figure 6:
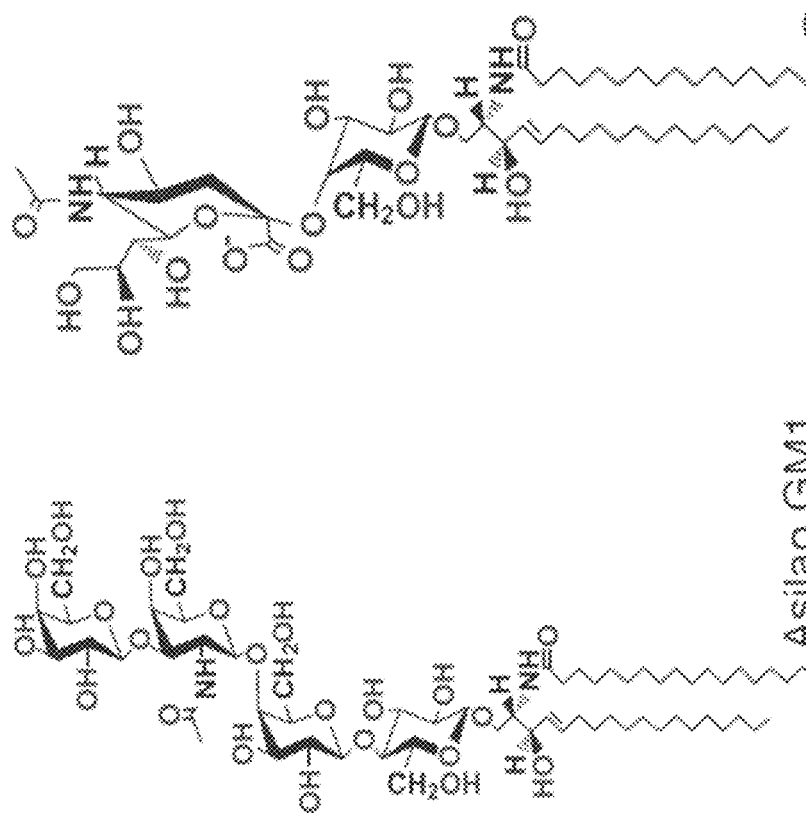
Figure 7:
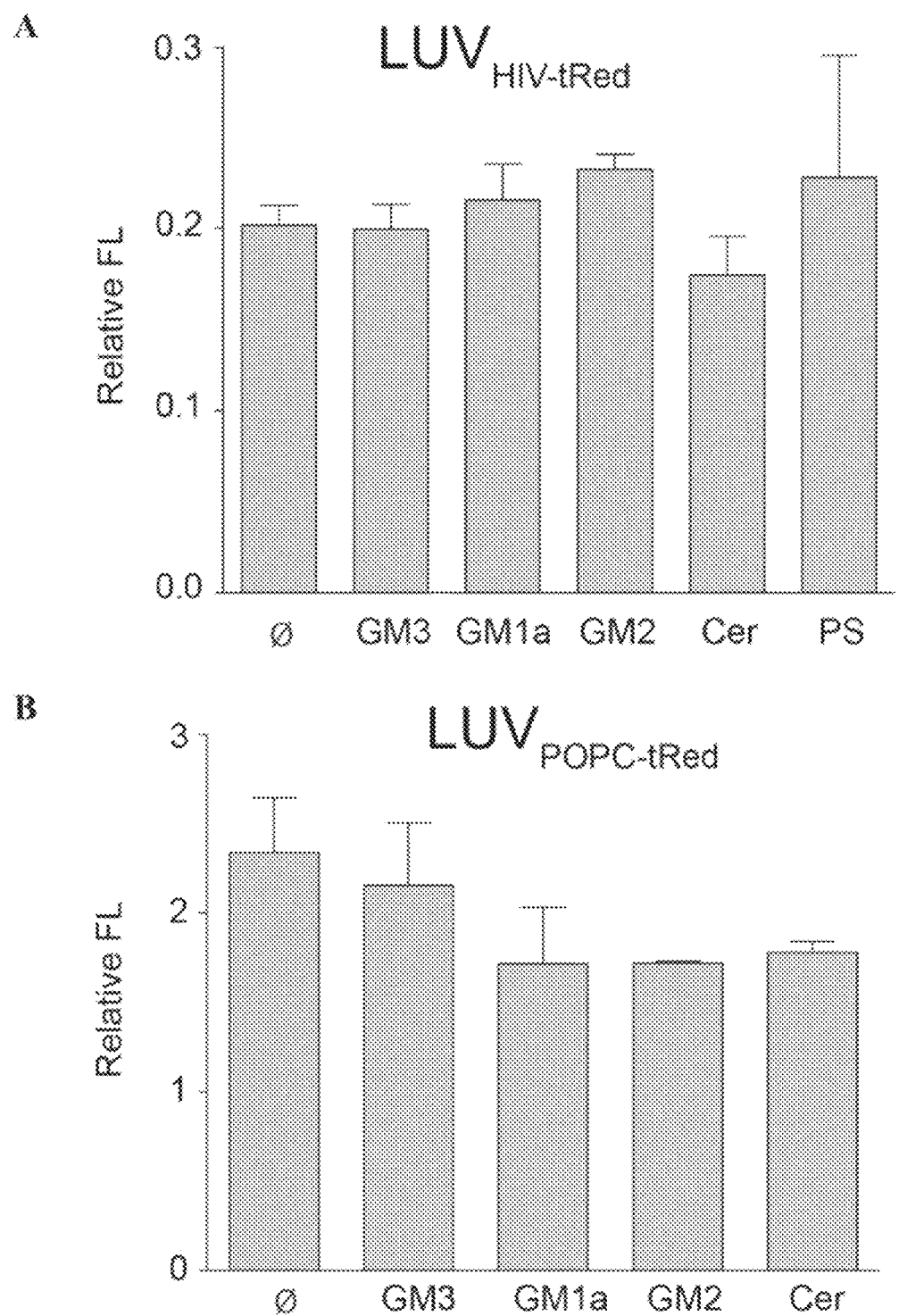
FIG. 7. Comparative fluorescence of Texas Red-containing LUVs. Maximum emission fluorescence at 608 nm of LUV$_{HIV-tRed}$ or LUV$_{POPC-tRed}$ containing the molecules indicated in the graphs. (A) Comparison of LUV$_{HIV-tRed}$ used in FIGS. 1 and 2, (B) Comparison of LUV$_{POPC-tRed}$ used in FIG. 3, (C) Comparison of LUV$_{HIV-tRed}$ used in FIG. 4, (D) Comparison of LUV$_{HIV-tRed}$ used in FIG. 5. Data show mean and SEM from independent measurements from at least two distinct LUV preparations.
Figure 7:
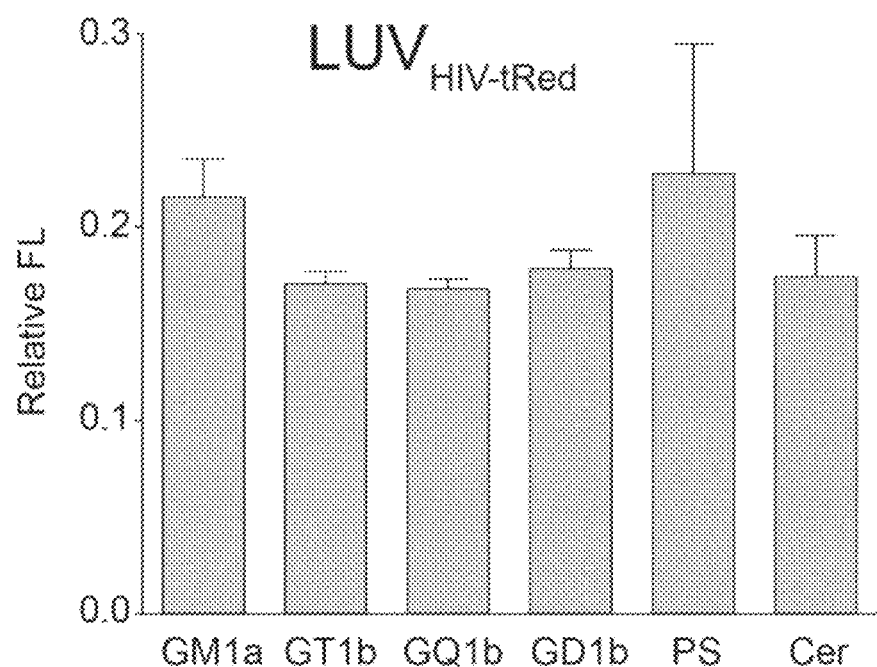
Figure 7:
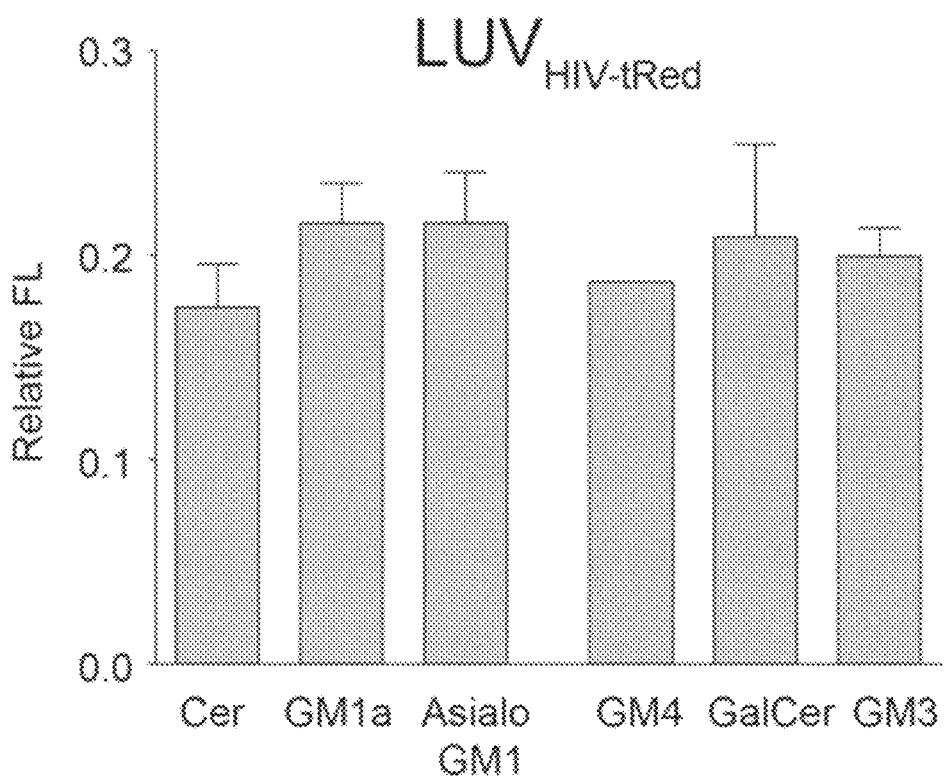
Figure 8:
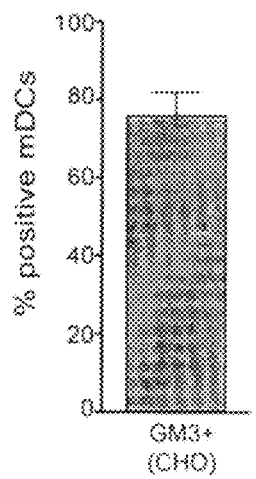
FIG. 8. Capture of VLPs produced in CHO cell line. Capture of VLP$_{HIV-Gag}$-eGFP produced in CHO cell line, which is only able to synthesize gangliosides up to GM3. A total of 2×10$^5$ mDCs were incubated for 4 hours at 37° C. with 75 ng of sucrose-pelleted VLP$_{HIV-Gag-eGFP}$ Gag, washed and analyzed by FACS to determine the percentage of eGFP positive cells. Data show mean values and SEM from one representative experiment out of two including cells from three donors.

To test whether gangliosides in the outer leaflet of HIV-1 or vesicular membranes can act as viral attachment factors yielding mDC uptake, Texas Red (tRed) labeled Large Unilamellar Vesicles (LUV) mimicking the size and lipid composition of HIV-1 ($LUV_{HIV\text{-}tRed}$) and containing different gangliosides were prepared. See FIG. 6, Lorizate M, et al., J. Biol. Chem. 2009; 284:22238-22247. All LUVs displayed equal fluorescence intensities. See FIG. 7. Mature DCs were pulsed with either $LUV_{HIV\text{-}tRed}$ or VLPs for four hours at 37° C. and the percentage of fluorescent cells was determined by Fluorescence Activated Cell Sorting (FACS). A high percentage of mDCs captured the fluorescent $VLP_{HIV\text{-}Gag\text{-}eGFP}$. See FIG. 1D. VLPs produced in the CHO cell line were also efficiently captured by mDCs. See FIG. 8. Uptake into mDCs was further observed for the murine retrovirus MuLV, which was previously shown to also contain gangliosides. See Chan R, et al., J. Virol. 2008; 82:11228-11238.

On the other hand, no significant uptake into mDCs was observed for $LUV_{HIV}$-tRed, which contained the main lipid constituents of HIV-1, but were devoid of gangliosides. See FIG. 1D. Uptake into mDCs remained negative for $LUV_{HIV\text{-}tRed}$ containing Ceramide (Cer) (P<0.0001, paired t test). See FIG. 1D. This was completely different when monosialogangliosides such as GM3, GM2 or GM1 were incorporated into the LUVs; mDCs were able to capture these liposomes with equal efficiency as $VLP_{HIV\text{-}Gag\text{-}eGFP}$. See FIG. 1D. To ensure that this capture was not merely due to electrostatic interactions between negatively charged gangliosides and surface charges on mDCs, $LUV_{HIV\text{-}tRed}$ containing negatively charged phosphatidylserine (PS) were analyzed in parallel and were found to be negative for mDC capture (P=0.0081, paired t test). See FIG. 1D. These results revealed that monosialogangliosides mediate vesicle capture by mDCs, and that the carbohydrate head group is essential for this process.

Example 2

Ganglioside-Containing Large Unilamellar Vesicles and VLPs Exploit a Common Entry Mechanism into mDCs and Reach the Same Compartment in mDCs To determine whether ganglioside-containing $LUV_{HIV-tRed}$ and $VLP_{HIV-Gag-eGFP}$ (and HIV-1) exploit a common entry mechanism into mDCs, several competition experiments were performed. Mature DCs were pulsed with decreasing amounts of GM2-containing $LUV_{HIV-tRed}$ and a constant amount of $VLP_{HIV-Gag-eGFP}$ for four hours at 37° C. After extensive washing, the percentage of eGFP- and tRed-positive cells was determined by FACS. GM2-containing $LUV_{HIV-tRed}$ efficiently competed for the uptake of $VLP_{HIV-Gag-eGFP}$ into mDCs in a dose-dependent manner (P<0.0001, paired t test). See FIG. 1E. No competition for VLP uptake was observed for $LUV_{HIV-tRed}$ containing Cer or lacking glycosphingolipids. See FIG. 1E. Hence, GM-containing $LUV_{HIV-tRed}$ and $VLP_{HIV-Gag-eGFP}$ use a common entry mechanism to gain access into mDCs, which is dependent on the carbohydrate head group.

Figure 2A:
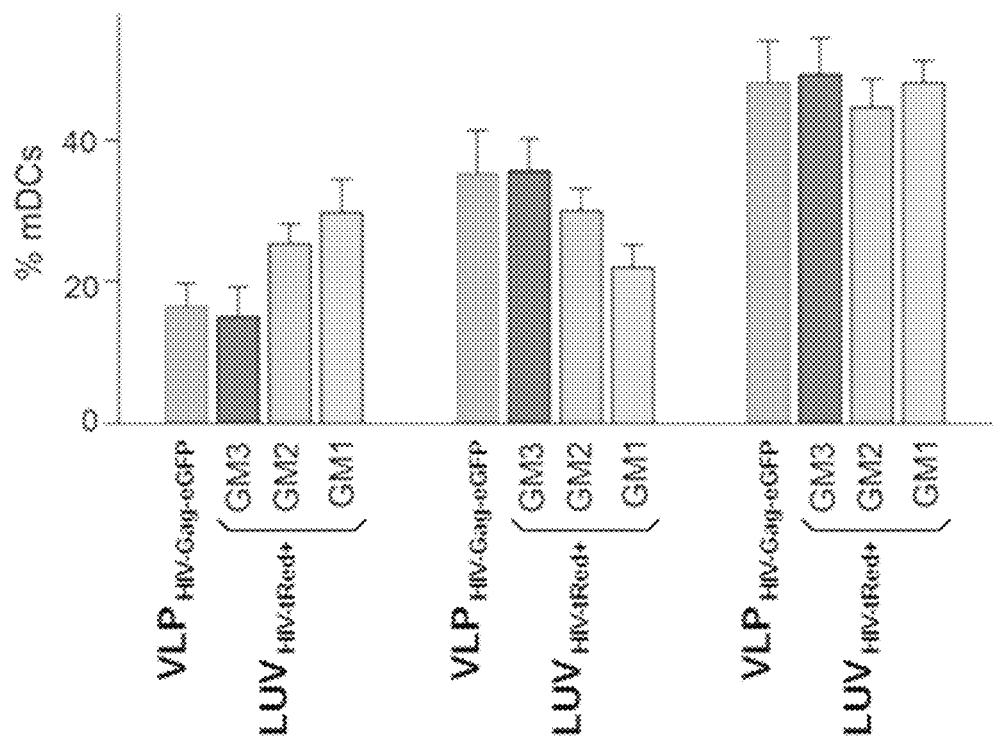
FIG. 2. Ganglioside-containing LUV$_{HIV-tRed}$ traffic to the same compartment as VLP$_{HIV-Gag-eGFP}$ in mDCs. (A) Percentage of mDCs with distinct capture patterns after 4 h of independent challenging with VLP$_{HIV-Gag-eGFP}$ or ganglioside-containing LUV$_{HIV-tRed}$. Data show mean values and SEM of more than 100 cells from 5 different donors. (B) Quantification of the percentage of VLP$_{HIv-Gag-eGFP}$ co-localizing with ganglioside-containing LUV$_{HIV-tRed}$ and vice versa, obtained analyzing at least 10 vesicles from mDCs of 3 different donors.
Figure 2B:
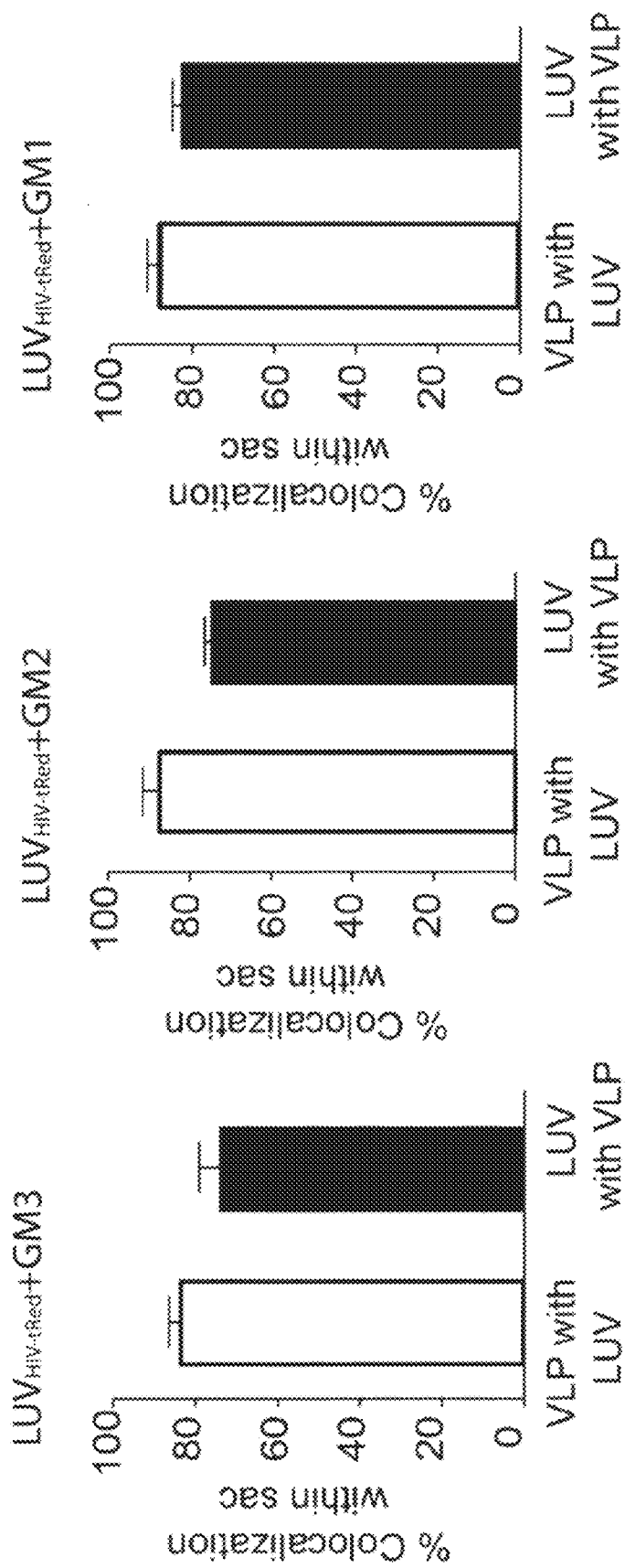

Next, whether GM-containing $LUV_{HIV-tRed}$ and $VLP_{HIV-Gag-eGFP}$ reach the same compartment in mDCs was investigated using spinning-disc confocal microscopy. Previously, three types of patterns for HIV-1 captured into mDC have been described: random, polarized, or sac-like compartments. See Izquierdo-Useros N, et al., J. Virol. 2007; 81: 7559-7570. The same patterns were also observed for GM-containing $LUV_{HIV-tRed}$ and the percentage of mDCs displaying the different patterns was similar regardless of the particle used. Thus, $VLP_{HIV-Gag-eGFP}$ and GM-containing $LUV_{HIV-tRed}$ not only compete for internalization, but also traffic to an analogous compartment within mDCs. To determine whether $VLP_{HIV-Gag-eGFP}$ and GM-containing $LUV_{HIV-tRed}$ are captured into the same compartment, mDCs were pre-incubated three hours at 37° C. with GM-containing $LUV_{HIV-tRed}$ and subsequently incubated with $VLP_{HIV-Gag-eGFP}$ for three additional hours. Confocal microscopy of fixed cells revealed that VLPs extensively co-localized with GM-containing $LUV_{HIV-tRed}$ (containing either GM1, GM2 or GM3) in the same intracellular compartment. See FIG. 2.

Example 3

Lateral Lipid Organization of the Vesicles does not Influence mDC Capture

Figure 3:
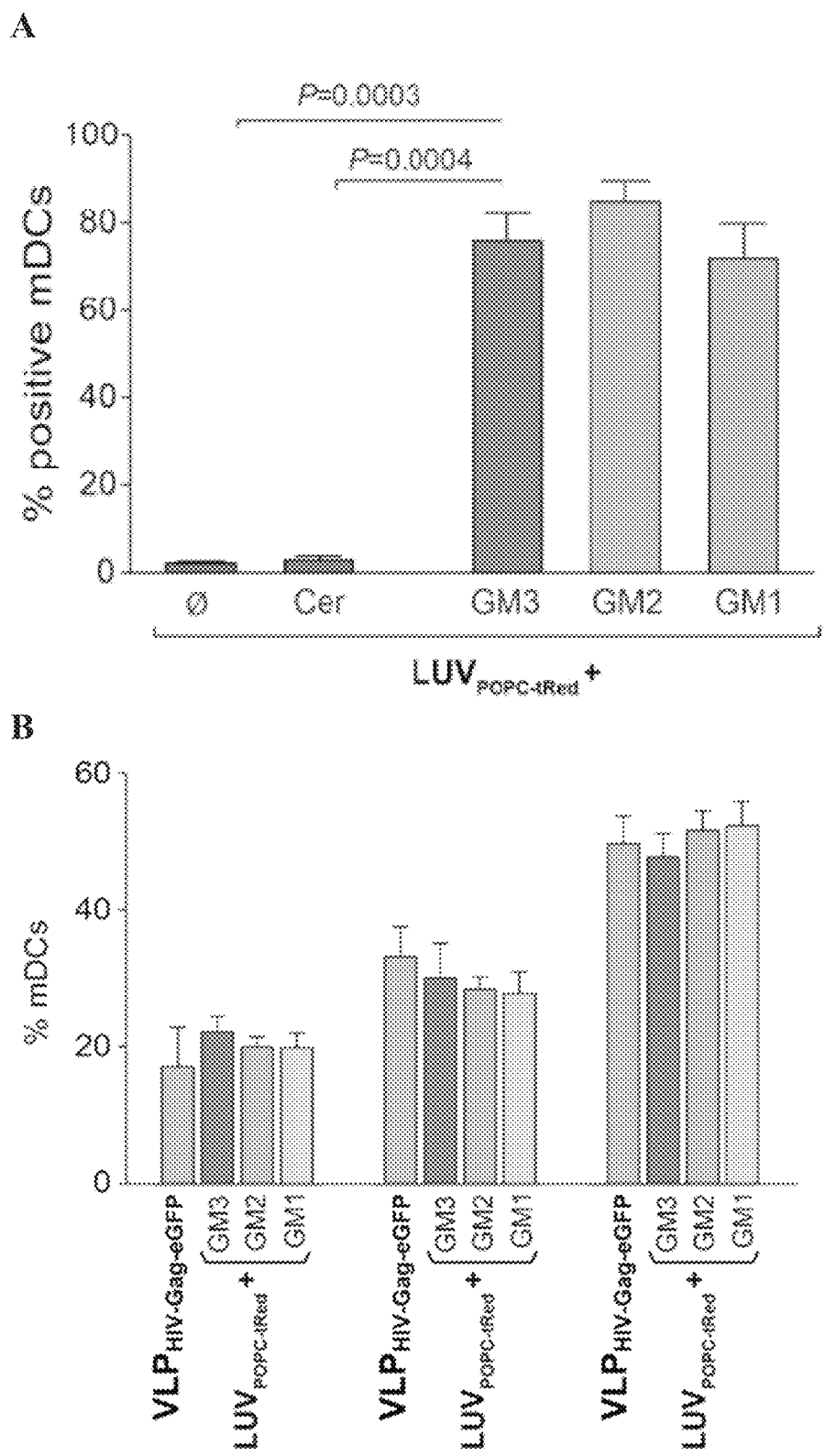
FIG. 3. Liquid ordered independence of ganglioside-containing LUV$_{HIV-tRed}$ capture by mDCs. (A) Comparative mDC capture of LUV$_{POPC-tRed}$ containing or not Cer, GM3, GM2 or GM 1. A total of 2×10$^5$ DCs were pulsed for 4 h at 37° C. with 100 μM of LUVs, washed with PBS and assessed by FACS to obtain the percentage of tRed positive cells. Data show mean values and SEM from three independent experiments including cells from at least six donors. Mature DCs capture significantly higher amounts of GM3-containing LUV$_{POPC-tRed}$ than Cer or LUV$_{POPC-tRed}$ (P values on the graph, paired t test). (B) Percentages of mDCs with distinct liposome capture pattern after 4 h of ganglioside-containing LUV$_{POPC-tRed}$ challenging.

Within the HIV-1 membrane, gangliosides are embedded in a liquid-ordered membrane. See Lorizate, 2009 and Chan, 2008, supra. Whether the liquid order or the specific lipid composition (other than gangliosides) of the particle membrane influence mDC capture was therefore assessed. Ganglioside interaction with cholesterol in lipid rafts is known to influence ganglioside conformation and alter its activity as a cellular receptor. See Lingwood D, et al., Nat. Chem. Biol. 2011; 7:260-262, Simons K, et al., Cold Spring Harb. Perspect. Biol. 2011, Simons, 2000 and Brown, 2000, supra. Mature DCs were incubated with $LUV_{POPC-tRed}$ composed of 1-palmitoyl-2-oleoyl-sn-glycero-3-phosphocholine (POPC) with or without different gangliosides. See FIG. 3A. In contrast to $LUV_{HIV-tRed}$, $LUV_{POPC-tRed}$ have a liquid-disordered membrane structure. Results for $LUV_{POPC-tRed}$ were very similar as for $LUV_{HIV-tRed}$ with efficient capture if either GM 1, GM2 or GM3 was present, while no uptake was observed for Cer containing $LUV_{POPC}$-tRed or $LUV_{POPC}$-tRed lacking gangliosides. See FIG. 3A. Furthermore, the percentage of mDCs displaying particles captured into random, polarized or sac-like compartments was again very similar for the different particles. See FIG. 3B. These results showed that ganglioside-containing LUVs use the same capture and trafficking pathway as $VLP_{HIV-Gag-eGFP}$ regardless of their lateral lipid organization, and suggested that gangliosides themselves were the key molecules responsible for mDC capture.

Example 4

Figure 4:
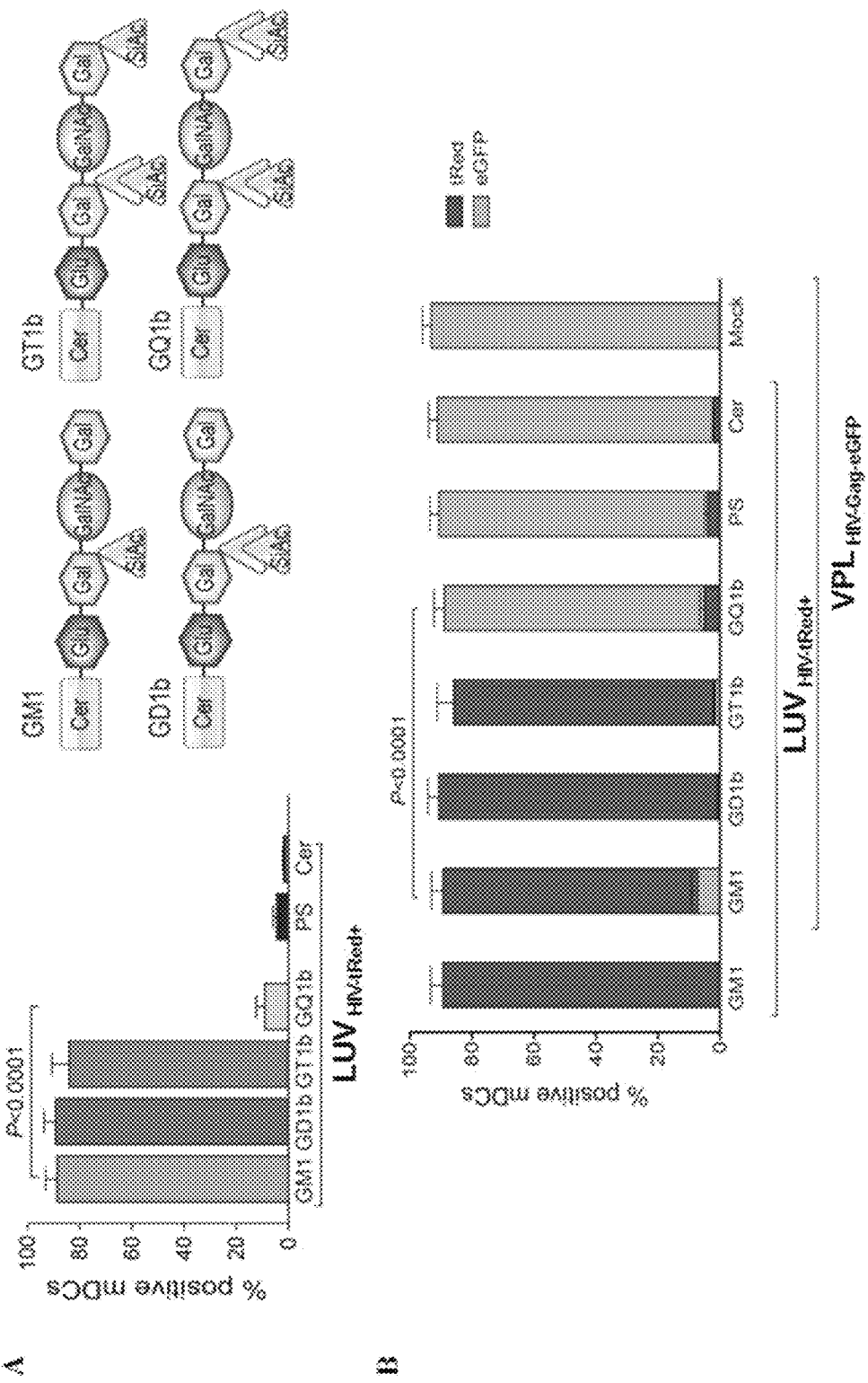
FIG. 4. mDC capture pattern of complex gangliosides. (A) Comparative mDC capture of distinct LUV$_{HIV-tRed}$ containing GM1, polysialoganglio sides such as GD1b, GT1b and GQ1b; PS and Cer. A total of 2×10$^5$ DCs were pulsed for 4 h at 37° C. with 100 μM of LUVs, washed with PBS and assessed by FACS to obtain the percentage of tRed positive cells. Data show mean values and SEM from two independent experiments including cells from six donors. Mature DCs capture significantly higher amounts of GM1-containing LUV$_{HIV-tRed}$ than GQ1b-containing LUV$_{HIV-tRed}$ (P<0.0001, paired t test). Schematic representation of the gangliosides in the LUVs employed for these experiments is shown next to the present illustration. (B) Capture competition between mDCs pulsed with 75 ng of VLP$_{HIV-Gag-eGFP}$ Gag and 100 μM of different polysialogangliosides LUV$_{HIv-tRed}$. Cells were incubated for 4 hours at 37° C., washed and analyzed by FACS to determine the percentage of eGFP- and tRed-positive cells. Data show mean values and SEM from two independent experiments including cells from six donors. mDCs capture fewer VLP$_{HIV-Gag-eGFP}$ in the presence of GM1-containing LUV$_{HIV-tRed}$ than in the presence of the same concentration of GQ1b containing LUV$_{HIV-tRed}$ (P<0.0001, paired t test).

Complex Gangliosides with Up to Three Sialic Acids Located in Distinct Positions of the Carbohydrate Head Group Share a Common Structure Determinant for mDC Uptake In order to gain further insight over the molecular structure required for efficient recognition by mDCs, $LUV_{HIV-TRed}$ carrying more complex gangliosides were produced. These LUVs included two, three and four sialic acid groups at diverse positions in the carbohydrate polar head group (di-, tri- and tetra-sialogangliosides). Mature DCs pulsed with an equal amount of $LUV_{HIV-tRed}$ containing gangliosides with two or three sialic acids (GD1b and GT1b, respectively) captured these particles with the same efficiency as GM1-$LUV_{HIV-tRed}$. Capture was almost completely lost for $LUV_{HIV-tRed}$ containing a ganglioside with four sialic acids (GQ1b). See FIG. 4A. Accordingly, $LUV_{HIV-tRed}$ carrying GD1b or GT1b efficiently competed for mDC uptake with $VLP_{HIV-Gag-eGFP}$, while no competition was observed for $LUV_{HIV-tRed}$ carrying GQ1b, PS or Cer. See FIG. 4B. These results indicated that complex gangliosides with up to three sialic acids located in distinct positions of the carbohydrate head group share a common structure determinant for mDC uptake.

The negative phenotype of Cer-containing LUVs indicated that the carbohydrate head group is specifically required for mDC capture. Sialic acid has been previously identified as cellular receptor for certain viruses. See Weis W, et al., Nature 1988; 333:426-431. Its importance for mDC capture was therefore tested. Incubation of mDCs with equal concentrations of $LUV_{HIV-tRed}$ containing Cer, GM1 or GM1 without the sialic acid group (Asialo GM1) revealed sialic acid-dependent capture. See FIG. 5A. In addition, in situ neuraminidase treatment of GM3-containing $LUV_{HIV-tRed}$ and $VLP_{HIV-Gag-eGFP}$, significantly reduced particle capture by mDCs. See FIG. 5B. Thus, the sialic acid moiety in gangliosides is necessary for specific recognition by mDCs. $LUV_{HIV-tRed}$ containing either GM4 (lacking the glucose moiety of GM3) or GalCer (lacking both the glucose and sialic acid moieties of GM3) was prepared to assess the contribution of other components of the carbohydrate head group. See FIG. 5C. Mature DCs incubated with GM4- or GalCer-containing $LUV_{HIV-tRed}$ showed only background levels of liposome capture, indicating that the glucose moiety of sphingolipids is also necessary for DC capture. See FIG. 5C.

Example 5

Soluble Carbohydrates Compete with Molecular Recognition of HIV-1 by mDCs

Figure 5:
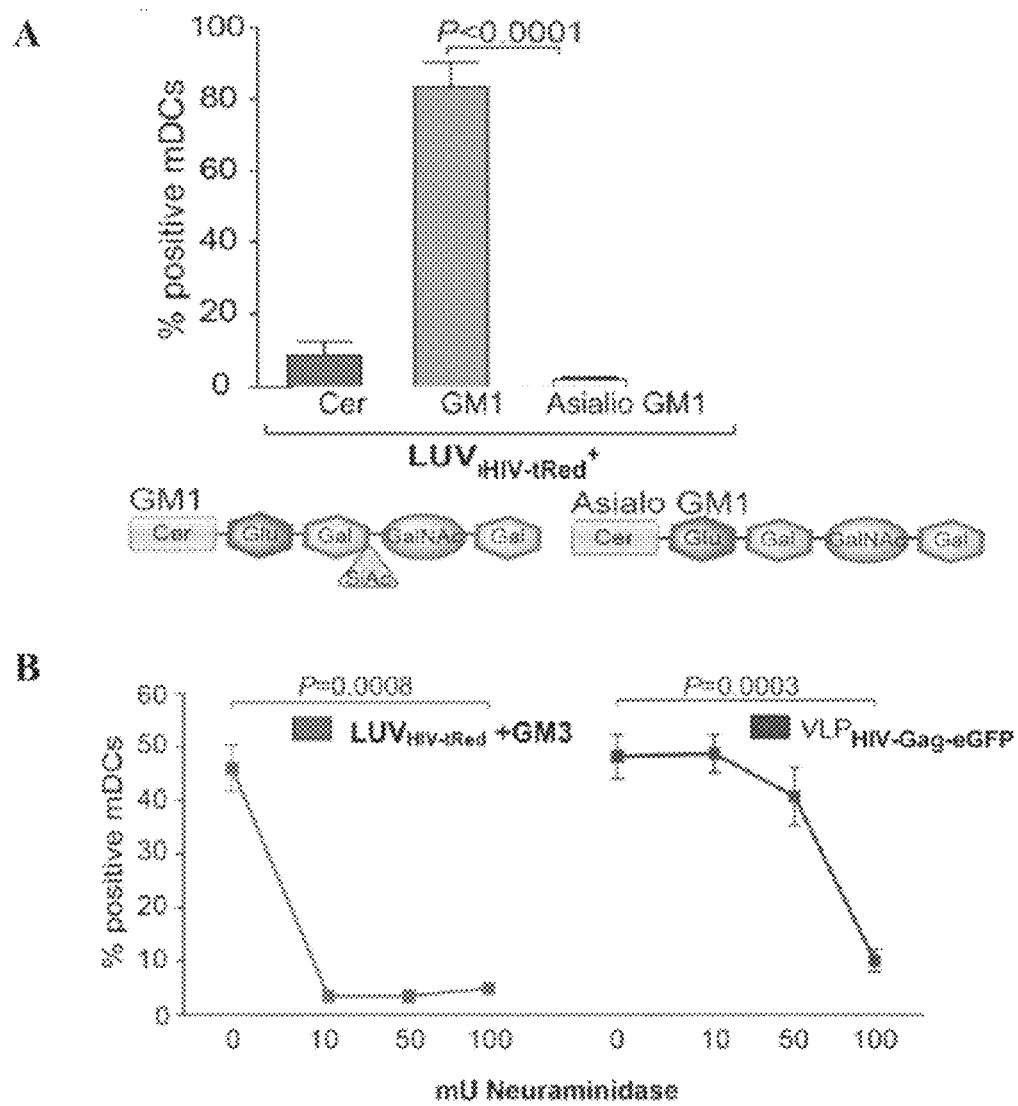
FIG. 5. Identification of the viral attachment domain present in gangliosides. (A) Comparative mDC capture of distinct LUV$_{HIV-tRed}$ containing Cer, GM1 or GM1 lacking sialic acid (Asialo GM1). A total of 2×10$^5$ DCs were pulsed for 4 h at 37° C. with 100 μM of LUVs, washed with PBS and assessed by FACS to obtain the percentage of tRed positive cells. Data show mean values and SEM from three independent experiments including cells from nine donors. Mature DCs capture significantly higher amounts of GM 1-containing LUV$_{HIV-tRed}$ than Asialo GM1-containing LUV$_{HIV-tRed}$ (P<0.0001, paired t test). (B) Comparative mDC capture of GM3-containing LUV$_{HIv-tRed}$ and VLP$_{HIv-Gag-eGFP}$ treated or not with neuraminidase to remove sialic acid. A total of 2×10$^5$ DCs were pulsed for 2 h at 37° C. with 25 μM of LUVs and 75 ng of VLP$_{HIV-Gag-eGFP}$ Gag treated or not with Clostridium perfringens neuraminidase ON, washed with PBS and assessed by FACS to obtain the percentage of tRed and eGFP positive cells. Data show mean values and SEM from two independent experiments including cells from five donors. Mature DCs capture significantly higher amounts of untreated particles than neuraminidase treated particles (P values on the graph, paired t test). (C) Comparative mDC capture of distinct LUV$_{HIV-tRed}$ containing GalCer, GM4, GM3 or GM1. A total of 2×10$^5$ DCs were pulsed for 4 h at 37° C. with 100 μM of LUVs, washed and assessed by FACS to obtain the percentage of tRed positive cells. Data show mean values and SEM from three independent experiments including cells from nine donors. Mature DCs capture significantly higher amounts of GM1-containing LUV$_{HIV-tRed}$ than GalCer or GM4-containing LUV$_{HIV-tRed}$ (P<0.0001, paired t test). Schematic representation of the molecules present in the LUVs for these experiments is shown in the bottom illustration. (D) Graph representing the relative capture of GM3-containing LUV$_{HIV-tRed}$ and VLP$_{HIV-Gag-eGFP}$ by mDCs that had been pre-incubated with 10 mM of soluble lactose or with 5 to 10 mM of GM3 carbohydrate polar head group, normalized to the level of LUV/VLP capture by mock-treated mDCs (set at 100%). mDCs captured less particles upon treatment with GM3 polar head group (P values on the graph, paired t test). Data show mean values and SEM from three independent experiments including cells from at least nine donors.
Figure 5:
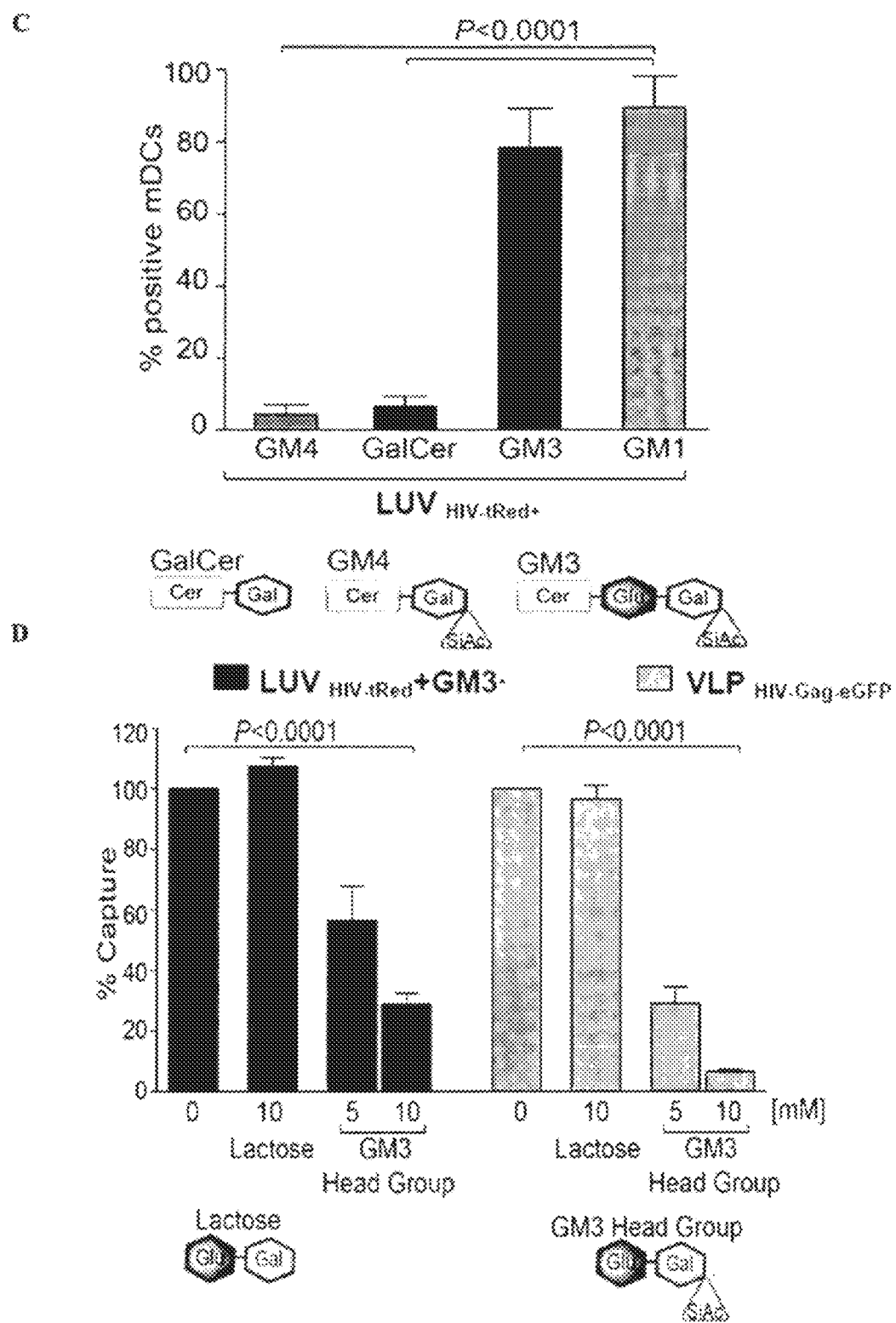

If the carbohydrate moiety constitutes the molecular recognition determinant for HIV-1 capture, soluble carbohydrates should compete for VLP and LUV uptake. Capture of GM3-containing LUV$_{HIV-tRed}$ or VLP$_{HIV-Gag-eGFP}$ by mDCs was completely blocked in the presence of soluble GM3, while equal concentrations of lactose (lacking the sialic acid group) had no effect. See FIG. 5D. Taken together, these data clearly showed that the sialyllactose moiety of gangliosides is the molecular determinant required for efficient HIV-1 recognition and capture by mDCs. The high concentrations of soluble GM3 required for competition in FIG. 5D compared to the low concentrations of gangliosides in LUVs (≈1000 fold less; FIG. 1C), suggested that the attachment of sialyllactose to Cer within membranes confers a higher binding affinity. In addition, the hydrophilic moiety of Cer itself could be part of the recognition domain, increasing directly the binding affinity to mDCs.

To further understand the structural determinants of the recognition domain, energy-minimized 3D models of the gangliosides tested were constructed. See FIG. 5e. These models indicated that sialyllactose is exposed in GM1, GM2, GM3, GD1b and GT1b, but absent in GM4 and Asialo GM1. See FIG. 6.

Example 6

Cells Expressing Siglec-1 can Efficiently Capture VLP$_{HIv-Gag-eGFP}$

Figure 9:
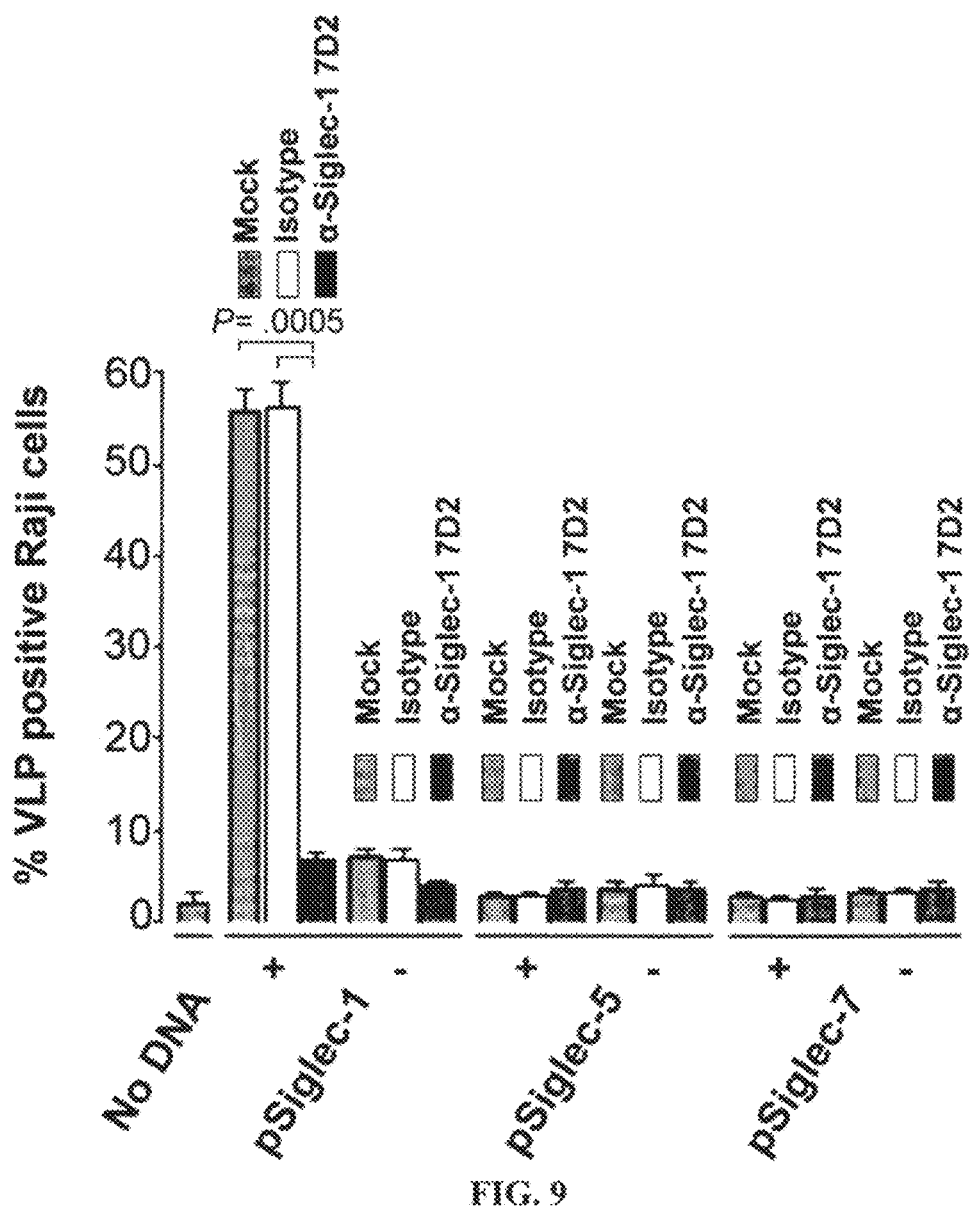
FIG. 9. Transfection of Siglecs in Raji B cells. Capture of VLP$_{HIV-Gag-eGFP}$ by Raji cells transfected with the indicated expression plasmids for Siglecs or mock transfected. Transfected Raji cells were preincubated with 10 μg/ml of the indicated mAbs and exposed to VLPs. Data show mean values and SEMs from two experiments including cells from four transfections.
Figure 10:
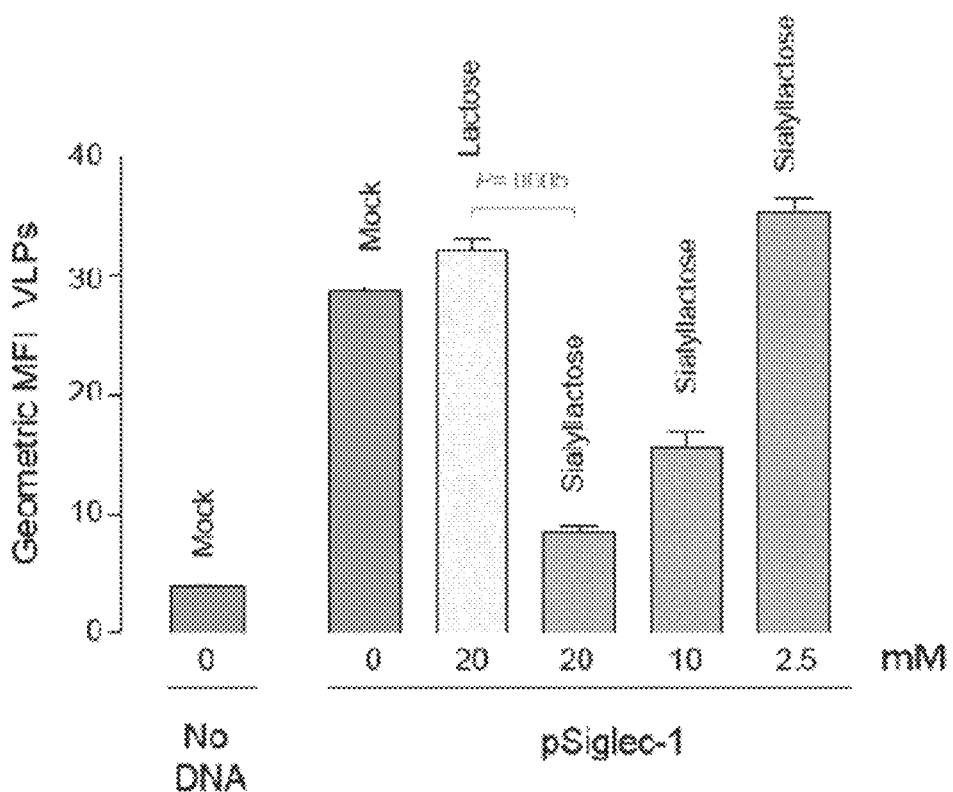
FIG. 10. Blocking effect of sialyllactose. Capture of VLP$_{HIVGag-eGFP}$ by Raji cells transfected with Siglec-1 expression plasmid or mock transfected. Cells were preincubated with the indicated concentrations of siallyllactose or soluble lactose and exposed to VLPs. Data show mean values and SEMs from triplicates of a transfection.
Figure 11:
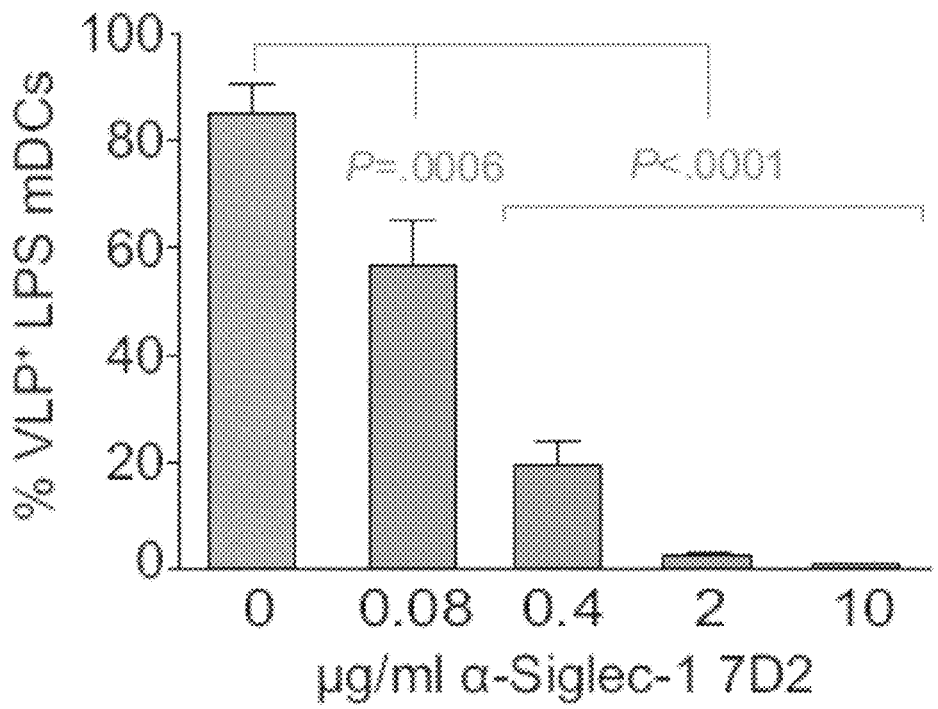
FIG. 11. Siglec-1 expressed in LPS mDCs capture distinct ganglioside containing vesicles, such as HIV-1 viral-like particles, liposomes, and exosomes. Capture of $VLP_{HIV-Gag-eGFP}$ by LPS mDCs that had been pre-incubated with decreasing concentrations of α-Siglec-1 mAb 7D2 before VLP exposure for 30 min at 37° C. Data show mean values and SEMs from three experiments including cells from six donors.
Figure 12:
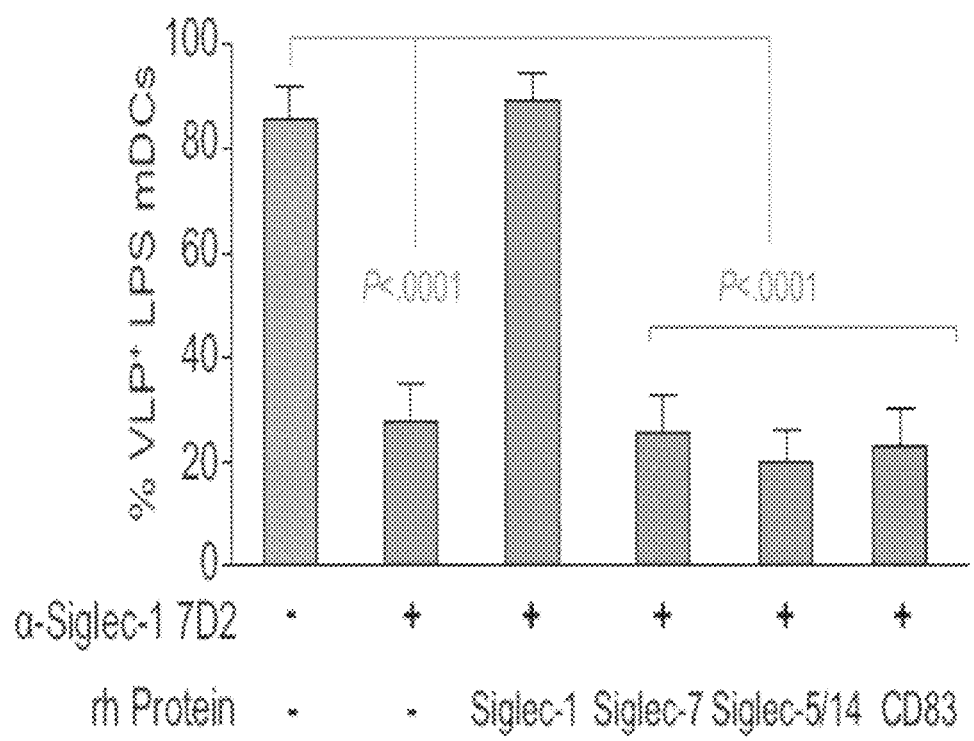
FIG. 12. Capture of $VLP_{HIV-Gag-eGFP}$ by LPS mDCs that had been pre-incubated with or without 2 μg/ml of α-Siglec-1 mAb 7D2 previously treated or not with at least a 100-fold molar excess of the indicated human recombinant proteins. Of note, Siglec-14 shares 100% of amino acid homology with Siglec-5 in the V-set domain. Data show mean values and SEMs from three experiments including cells from nine donors.
Figure 13:
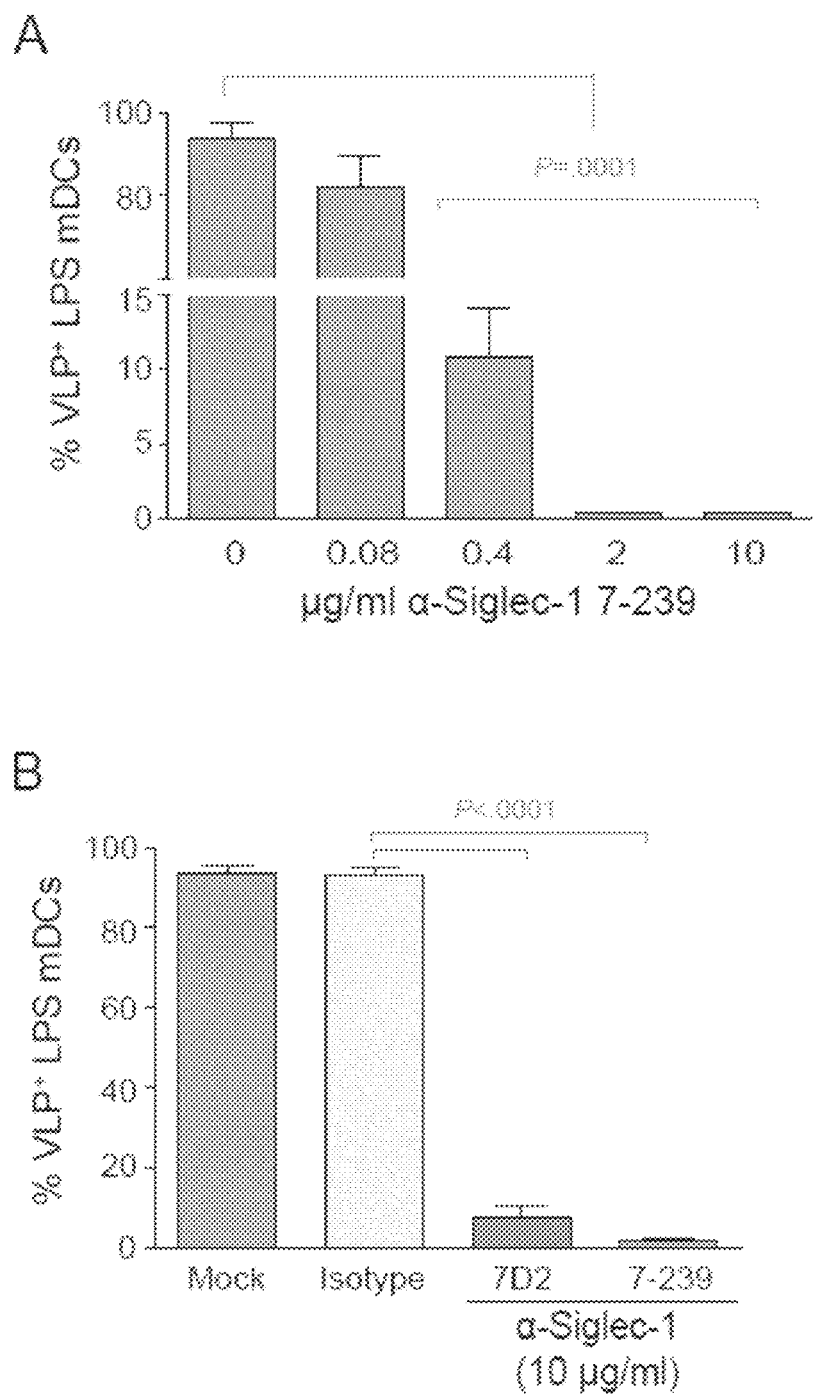
FIG. 13. Blocking effect of α-Siglec-1 mAb 7-239. (A) Capture of $VLP_{HIV-Gag-eGFP}$ by LPS mDCs that had been pre-incubated with decreasing concentrations of α-Siglec-1 mAb 7-239 before VLP exposure for 30 min at 37° C. Data show mean values and SEMs from four donors. (B) Capture of $VLP_{HIV-Gag-eGFP}$ by LPS mDCs that had been pre-incubated with 10 μg/ml of the indicated mAbs before VLP exposure for 3 h at 37° C. Data show mean values and SEMs from two experiments including cells from seven donors.

Raji B cell line, which lacks endogenous expression of Siglec-1 and could be efficiently transfected without unspecific up-regulation of Siglec-1, were used for transfection. Transfection of a Siglec-1 expression vector in Raji B cell line significantly enhanced VLP$_{HIV-Gag-eGFP}$ capture in the Siglec-1-positive cell population, and this effect was abolished by pretreatment with the anti-Siglec-1 mAb 7D2 (p=0.0005; FIG. 9). No increased capture was seen in the Siglec-1-negative population of Siglec-1 transfected cells or following transfection of Siglec-5 or Siglec-7 expression plasmids (FIG. 9). Pre-incubation with sialyllactose also blocked VLP capture in Siglec-1 transfected Raji cells (FIG. 10). Titration of the anti-Siglec-1 mAb 7D2 revealed a dose-dependent inhibition of VLP capture (FIG. 11). Specificity of the mAb 7D2-mediated inhibition was confirmed by pre-incubation of this mAb with different Siglec proteins. Pre-incubation with purified Siglec-1 completely restored VLP capture, while pre-incubation with purified Siglec-7, -5/14, or CD83 had no effect (FIG. 12). Although the epitope recognized by 7D2 mAb might not constitute the actual viral binding site, since 7D2 Fab fragments did not lead to a block in VLP capture, titration with 7-239, a different a-Siglec-1 mAb, confirmed a dose-dependent inhibition of VLP capture (FIG. 13A)

Example 7

Figure 14:
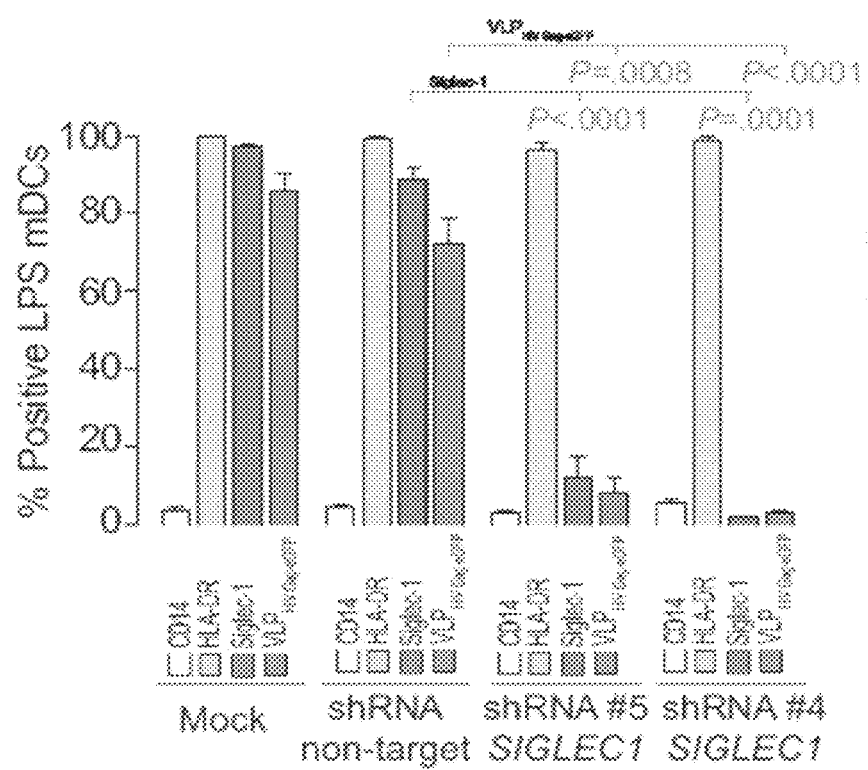
FIG. 14. Siglec-1 silencing blocks viral capture and trans-infection, while de novo expression of SIGLEC1 rescues it. Interference of Siglec-1. Percentage of LPS mDCs positive for CD14, HLA-DR, Siglec-1, or VLP capture following mock transduction or transduction with nontarget or two different Siglec-1-specific shRNAs. Data show mean values and SEMs from four experiments including cells from at least four donors.

Silencing Siglec-1 Leads to a Decrease in the Capture VLP$_{HIv-Gag-eGFP}$ by DCs To verify the essential role of Siglec-1 during HIV-1 capture and trans-infection, a complementary experimental strategy was applied: RNA interference to reduce Siglec-1 expression levels in LPS mDCs and transfection of Siglec-1 into cells devoid of this receptor. In this approach, DCs with lentiviral particles coding for different shRNAs were transduced by co-infection with vpx-expressing lentiviruses to counteract the restriction factor SAMHD1 and facilitate DC productive infection. Transduction of two different Siglec1-specific shRNAs, but not of a non-target shRNA control, led to a drastic decrease in Siglec-1 surface expression and a concurrent loss of VLP$_{HIV-Gag-eGFP}$ capture (FIG. 14).

The invention claimed is:
1. A method for blocking the entry of HIV into dendritic cells in a subject in need thereof, said method comprising administering to said subject an inhibitor of the interaction between sialoadhesin and sialyllactose, wherein said inhibitor is a vesicle comprising a molecule comprising a sialyllactose moiety, and wherein said molecule is a ganglioside having less than four sialic acids.
2. The method according to claim 1, wherein the HIV is HIV-1.

* * * * *

UNITED STATES PATENT AND TRADEMARK OFFICE
CERTIFICATE OF CORRECTION

PATENT NO. : 9,789,130 B2
APPLICATION NO. : 14/366839
DATED : October 17, 2017
INVENTOR(S) : Nuria Izquierdo Useros et al.

Page 1 of 1

It is certified that error appears in the above-identified patent and that said Letters Patent is hereby corrected as shown below:

In the Specification

Column 8, Line 36: "members of the poxyiridae" should be --members of the poxviridae--.

Column 37, Line 3: "EBA, GLURP, RAPT" should be --EBA, GLURP, RAP1--.

Column 37, Line 4: "PfEMP1, Pf332, LSAT" should be --PfEMP1, Pf332, LSA1--.

Column 41, Line 25: "embodiment, the ganglio side" should be --embodiment, the ganglioside--.

Column 44, Line 67: "gag (e.g. p6, p'7," should be --gag (e.g. p6, p7,--.

Column 46, Lines 44-45: "may include chemo luminescent" should be --may include chemoluminescent--.

Column 52, Lines 29-30: "dimyristoylphosphatidylcho line (DMPC), dipalmitoyl phosphatidylcho line (DPPC)" should be --dimyristoylphosphatidylcholine (DMPC), dipalmitoyl phosphatidylcholine (DPPC),--.

Column 55, Line 58: "L1 M. et al., 2005, J. Viol." should be --Li M. et al., 2005, J. Virol.--.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*